(12) United States Patent
Vennerstrom et al.

(10) Patent No.: US 6,486,199 B1
(45) Date of Patent: Nov. 26, 2002

(54) SPIRO AND DISPIRO 1,2,4-TRIOXOLANE ANTIMALARIALS

(75) Inventors: Jonathan L. Vennerstrom, Omaha, NE (US); Yuxiang Dong, Omaha, NE (US); Jacques Chollet, Basel (CH); Hugues Matile, Basel (CH)

(73) Assignee: Medicines for Malaria Venture MMV International Centre Cointrin (CH)

( * ) Notice: Subject to any disclaimer, the term of this patent is extended or adjusted under 35 U.S.C. 154(b) by 0 days.

(21) Appl. No.: 09/886,666

(22) Filed: Jun. 21, 2001

(51) Int. Cl.⁷ .................. A61K 31/335; A61K 31/357; C07D 323/02
(52) U.S. Cl. ........................ 514/462; 549/341
(58) Field of Search ............... 549/341; 514/462

(56) References Cited

U.S. PATENT DOCUMENTS

| | | |
|---|---|---|
| 3,621,062 A | 11/1971 | Archer et al. |
| 3,673,222 A | 6/1972 | Archer et al. |
| 3,682,991 A | 8/1972 | Tullar et al. |
| 4,816,478 A | 3/1989 | Thornfeldt |
| 4,978,676 A | 12/1990 | Thornfeldt |
| 5,053,342 A | 10/1991 | Lawrence |
| 5,171,676 A | 12/1992 | Ziffer et al. |
| 5,216,175 A | 6/1993 | Avery et al. |
| 5,219,880 A | 6/1993 | Thornfeldt |
| 5,264,879 A | 11/1993 | Shikama |
| 5,270,344 A | 12/1993 | Herman |
| 5,430,148 A | 7/1995 | Webber et al. |
| 5,510,356 A | 4/1996 | Vennerstrom |
| 5,559,145 A | 9/1996 | Jeffort |
| 5,578,637 A | 11/1996 | Lai et al. |
| 5,614,178 A | 3/1997 | Bloom et al. |
| 5,672,624 A | 9/1997 | Posner |
| 5,721,209 A | 2/1998 | Horwitz et al. |
| 5,780,675 A | 7/1998 | Royer et al. |
| 5,817,692 A | 10/1998 | Posner |
| 5,932,591 A | 8/1999 | Posner et al. |

OTHER PUBLICATIONS

Keul, Helmut, Chem. Berichte, 108(4), pp. 1207–1217, 1975.*

Posner, "Antimalarial peroxides in the qinghaosu (artemisinin) and yingzhaosu families", *Exp. Opin. Ther. Patents* 8(11) 1487–1493 (1998) Ashley Publications Ltd. ISSN 1354–3776.

Jefford, "Peroxidic Antimalarials", *Advances in Drug Research*, vol. 29:271–323 (ISBN 0–12–013329–6) copyright 1997 Academic Press Ltd.

de Almeida Barbosa, Luiz–Claudio, "The design, synthesis and biological evaluation of stable ozonides with antimalarial activity", *J. Chem. Soc., Perkin Trans. 1*, 1101–1105 (1996).

de Almeida Barbosa, Luiz–Claudio, "Synthesis of some Stable Ozonides with Anti–malarial Activity", *J. Chem. Soc., Perkin Trans. 1*, 3251 (1992).

Vennerstrom, et al., "Dispiro–1,2,4,5–tetraoxanes: A New Class of Antimalarial Peroxides", *J. Med. Chem.* 35(16):3023–3027 (1992).

* cited by examiner

Primary Examiner—Ba K. Trinh
(74) Attorney, Agent, or Firm—McKee, Voorhees & Sease, P.L.C.

(57) ABSTRACT

A means and method for treating malaria using a spiro or dispiro 1,2,4-trioxolane is described. The preferred 1,2,4-trioxolanes include a spiroadamantane group on one side of the trioxolane group, and a spirocyclohexyl or spiropiperidyl ring on the other side of the trioxolane group, whereby the spirocyclohexyl ring is preferably functionalized or substituted at the 4-position or a spiropiperidyl ring that is functionalized or substituted at the nitrogen atom. In comparison to artemisinin semisynthetic derivatives, the compounds of this invention are structurally simple, easy to synthesize, non-toxic, and potent against malarial parasites.

34 Claims, No Drawings

SPIRO AND DISPIRO 1,2,4-TRIOXOLANE ANTIMALARIALS

FIELD OF THE INVENTION

This invention relates to compositions and methods for treating malaria. Specifically, this invention relates to pharmaceutical compositions including spiro and dispiro trioxolanes, and methods of their use and manufacture.

BACKGROUND OF THE INVENTION

Malaria is an acute and often chronic infectious disease resulting from the presence of protozoan parasites within red blood cells. Caused by single-celled parasites of the genus Plasmodium, malaria is transmitted from person to person by the bite of female mosquitos.

Although once prevalent in North America and other temperate regions of the world, today malaria occurs mostly in tropical and subtropic countries. Each year, between 400 million and 600 million people contract the disease, and 1.5 million to 2.7 million die of the disease.

Four species of Plasmodium protozoan parasites are generally responsible for malaria, including *Plasmodium vivax, Plasmodium falciparum, Plasmodium malariae*, and *Plasmodium ovale*. Of the four, *Plasmodium falciparum* is the most dangerous, accounting for half of all clinical cases of malaria and 90% of deaths from the disease.

The transmission of malaria begins when a female mosquito bites a human already infected with the malaria parasite. When the infected mosquito bites another human, sporozoites in the mosquito's saliva are transferred into the blood, which then travel to the liver. In the liver, the sporozoites divide rapidly, then enter the bloodstream where they invade red blood cells. Inside these blood cells, the merozoites multiply rapidly until they cause the red blood cells to burst, releasing into the blood stream a new generation of merozoites that then infect other red blood cells.

The symptoms associated with malaria are generally associated with the bursting of the red blood cells. The destruction of the red blood cells spills wastes, toxin, and other debris into the blood. This in turn causes an intense fever that can leave the infected individual exhausted and bedridden. More severe symptoms associated with repeat infections and/or infection by *Plasmodium falciparum* include anemia, severe headaches, convulsions, delirium and, in some instances, death.

The treatment of malaria has been especially difficult due to the ability of malaria parasites to develop resistance to drugs. Quinine, an antimalarial compound that is extracted from the bark of the South American cinchona tree, is one of the oldest and most effective pharmaceuticals in existence. The downside to quinine is that it is short-acting, and fails to prevent disease relapses. Further, quinine is associated with side effects ranging from dizziness to deafness.

Chloroquine is a synthetic chemical similar to quinine. It became the drug of choice for malaria when it was developed in the 1940s due to its effectiveness, ease of manufacture, and general lack of side effects. However, in the last few decades, malaria parasites in many areas of the world have become resistant to chloroquine.

Mefloquine is another synthetic analog of quinine that has been used in the treatment of malaria. Malaria parasites have also developed resistance to mefloquine, however. Mefloquine is also associated with undesirable central nervous side effects in some patients, including hallucinations and vivid nightmares.

Antifolate drugs are effective against malaria parasites by inhibiting their reproduction. Although the parasites have also developed a resistance to antifolate drugs, the drugs can still be used effectively in combination with other types of antimalarials. The use of combination therapies in treating malaria has the drawbacks of being inconvenient and expensive, however.

More recent developments in the treatment of malaria have involved the use of the peroxide functional group, as exemplified by the drug artemisinin, which contains a unique 1,2,4-trioxane heterocyclic pharmacophore. The antimalarial action of artemisinin is due to its reaction with the iron in free heme molecules in the malaria parasite with the generation of free radicals leading to cellular destruction.

Although the clinically useful semisynthetic artemisinin derivatives are rapid acting and potent antimalarial drugs, they have several disadvantages including recrudescence, neurotoxicity, (Wesche et al., 1994) and metabolic instability. (White, 1994). Although many synthetic antimalarial 1,2,4-trioxanes have since been prepared (Cumming et al., 1996; Jefford, 1997), there exists a need in the art to identify new peroxide antimalarial agents, especially those which are easily synthesized, are devoid of neurotoxicity, and which possess improved pharmacokinetic properties, e.g. improved stability, oral absorption, etc.

Accordingly, it is a primary objective of the present invention to provide compositions and methods for prophylaxis and treatment of malaria using Spiro and dispiro 1,2,4-trioxolanes.

It is a further objective of the present invention to provide a composition and method for prophylaxis and treatment of malaria using Spiro and dispiro 1,2,4-trioxolanes that is nontoxic.

It is a further objective of the present invention to provide a composition and method for prophylaxis and treatment of malaria using Spiro and dispiro 1,2,4-trioxolanes that is metabolically stable and orally active.

It is yet a further objective of the present invention to provide a composition and method for prophylaxis and cost-effective treatment of malaria using Spiro and dispiro 1,2,4-trioxolanes.

It is a further objective of the present invention to provide compositions and methods for prophylaxis and treatment of malaria using Spiro and dispiro 1,2,4-trioxolanes that can be used either as stand-alone medicaments or in combination with other agents.

The method and means of accomplishing each of the above objectives as well as others will become apparent from the detailed description of the invention which follows hereafter.

SUMMARY OF THE INVENTION

The invention describes a method and composition for treating malaria with Spiro and dispiro 1,2,4-trioxolanes, their prodrugs and analogues. The trioxolanes of this invention are sterically hindered on one side of the trioxolane heterocycle in order to provide chemical and metabolic stability to the trioxolane ring for better in vivo activity. The spiro and dispiro trioxolanes are preferably sterically hindered with an unsubstituted, mono-, di-, or poly-substituted $C_5$–$C_{12}$ spiro cycloalkyl group, which is most preferably spiroadamantane. The spiro and dispiro trioxolanes also preferably include a spirocyclohexyl that is preferably functionalized or substituted at the 4-position or a spiropiperidyl ring that is functionalized or substituted at the nitrogen atom.

The invention embraces achiral, achiral diastereomers, racemic mixtures, as well as enantiomeric forms of the compounds.

The trioxolanes of this invention possess excellent potency and efficacy against Plasmodium parasites, and a low degree of neurotoxicity. In addition, several of the trioxolanes are suitable for both oral and non-oral administration. Moreover, in comparison to artemisinin semisynthetic derivatives, the compounds of this invention are structurally simple, easy and inexpensive to synthesize, and can be used effectively alone or in conjunction with other antimalarials.

DETAILED DESCRIPTION OF THE PREFERRED EMBODIMENT

The present invention relates to the development of spiro and dispiro 1,2,4-trioxolanes for use in the prophylaxis and treatment of malaria. The present invention is predicated upon the unexpected discovery that trioxolanes that are relatively sterically hindered on at least one side of the trioxolane heterocycle provide metabolic and chemical stability to the trioxolane ring, thereby providing better in vivo activity, especially with respect to oral administration.

As used herein the term "prophylaxis-effective amount" refers to a concentration of compound of this invention that is effective in inhibiting or preventing infection and subsequent disease by malarial parasites. Likewise, the term "treatment-effective amount" refers to a concentration of compound that is effective in treating malaria in terms of preventing an increase in the concentration of malarial parasites, decreasing the concentration of malarial parasites, and/or "curing" a malaria infection, i.e. survival for 30 days post-infection.

Trioxolanes are relatively stable peroxidic compounds based on literature precedent (Griesbaum et al., 1997a; 1997b). This may be due, in part, to the lack of α-hydrogen atoms. The present inventors have synthesized new compounds in the trioxolane class having both superior antimalarial potency and oral efficacy. Furthermore, the compounds of this invention have low toxicity, and half-lives conducive to treatment of malaria which are believed will permit short-term treatment regimens comparing favorably to other artemisinin-like drugs. These compounds may also be used in malaria prophylaxis.

The tetrasubstituted trioxolanes of this invention have the following general structural formula:

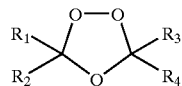

wherein $R_1$, $R_2$, $R_3$, and $R_4$ represent combinations of ring systems, acyclic systems, and functional groups that provide sufficient steric hindrance about the trioxolane ring in order to give the ring chemical and metabolic stability. $R_1$, $R_2$, $R_3$ and $R_4$ may be the same or different, and may be a linear or branched alkyl, aryl, or alkaryl group which is optionally substituted. In the alternative, $R_1$ and $R_2$ taken together and/or $R_3$ and $R_4$ taken together may form an alicyclic group which is optionally interrupted by one or more oxygen, sulfur or nitrogen atoms and which group is optionally substituted. In no event may any of $R_1$, $R_2$, $R_3$ or $R_4$ be hydrogen.

Preferably, $R_1$ and $R_2$ taken together and/or $R_3$ and $R_4$ taken together is a mono- or di-substituted $C_{5-C_{12}}$ spirocycloalkyl group which is optionally interrupted by one or more oxygen, sulfur, or nitrogen atoms, and which group is optionally substituted.

Most preferably, $R_1$ and $R_2$ taken together or $R_3$ and $R_4$ is spiroadamantane. It is hypothesized that the sterically demanding adamantane protects the trioxolane ring from premature chemical or metabolic decomposition in situ.

The inventors have further found that in the most preferred compounds of this invention, $R_1$ and $R_2$ taken together is adamantane, and $R_3$ and $R_4$ taken together is a spirocyclohexyl ring that is functionalized or substituted at the 4-position. The spirocyclohexyl ring may be optionally interrupted by one or more oxygen, sulfur or nitrogen atoms. The functional group may be a linear or branched alkyl, ketone, acid, alcohol, amine, amide, sulfonamide, ether, ester, oxime, urea, ether, sulfone, lactone, carbamate, semicarbazone, phenyl, heterocycle, or alicyclic group which is optionally substituted. Other substituents at the 4-position of the spirocyclohexyl ring are also possible that fall within the scope of this invention. The spirocyclohexyl ring may also be substituted at other positions besides the 4-position. For instance, the inventors have synthesized several compounds substituted at the 2-position of the spirocyclohexyl ring that provide excellent antimalarial potency.

Below are several dispiro 1,2,4-trioxolanes synthesized in accordance with the teachings of this invention. "OZ" is an internal designation for these compounds that will be used throughout the remainder of the application for convenience:

OZ Series 1 (OZ01–OZ9)

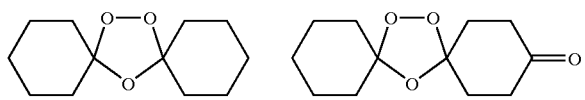

OZ01
MW 212.29

OZ02
MW 226.27

OZ03
MW 264.36

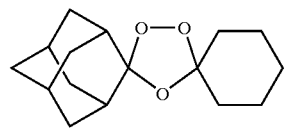

OZ04
MW 316.43

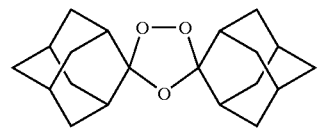

OZ05
MW 278.34

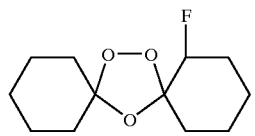
OZ06
MW 230.28
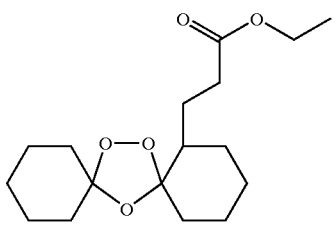
OZ07
MW 312.40
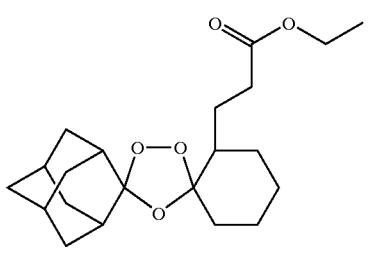
OZ08
MW 364.48
OZ09
MW 340.41
OZ Series 2 (OZ10–OZ18)
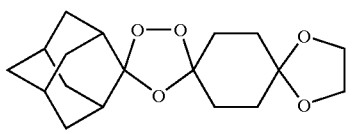
OZ10
MW 322.40
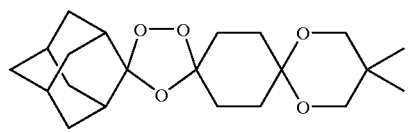
OZ11
MW 364.48
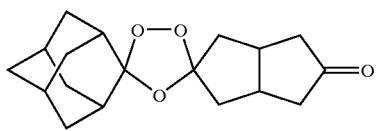
OZ12
MW 304.38
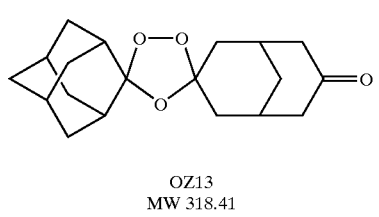
OZ13
MW 318.41
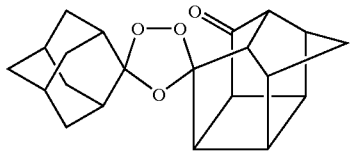
OZ14
MW 340.41
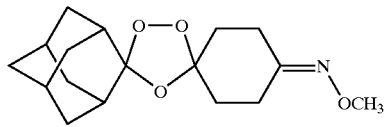
OZ15
MW 307.38
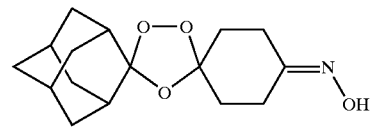
OZ16
MW 293.36
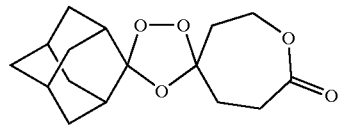
OZ17
MW 294.34
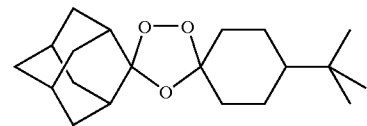
OZ18
MW 320.47

OZ Series 3 (OZ19–OZ27)
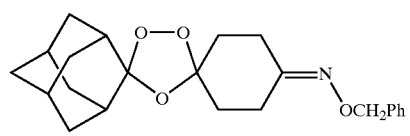
OZ19
MW 383.48
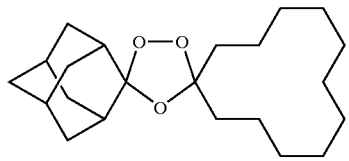
OZ20
MW 348.52
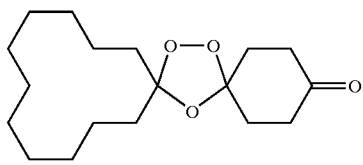
OZ21
MW 310.43
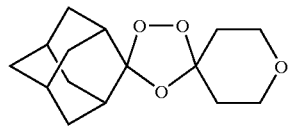
OZ22
MW 266.36
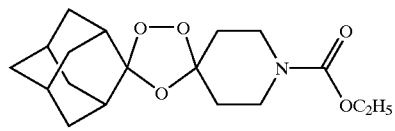
OZ23
MW 337.41
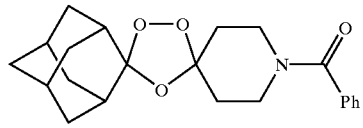
OZ24
MW 369.45
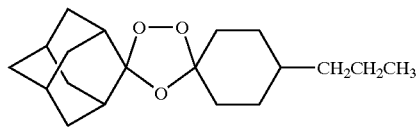
OZ25
MW 306.44
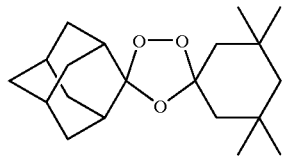
OZ26
MW 320.47
-continued
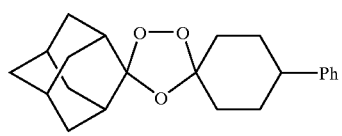
OZ27
MW 340.46
OZ Series 4 (OZ28–OZ36)
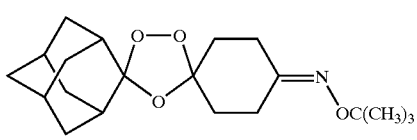
OZ28
MW 349.46
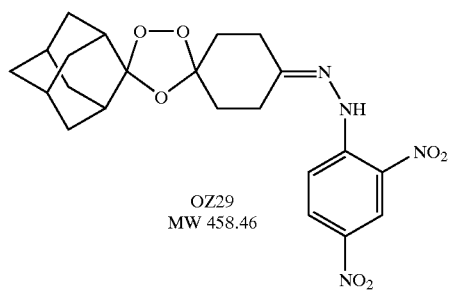
OZ29
MW 458.46
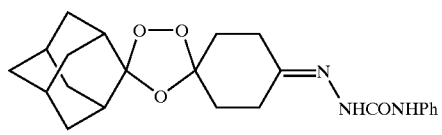
OZ30
MW 411.49
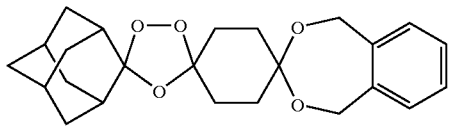
OZ31
MW 398.49
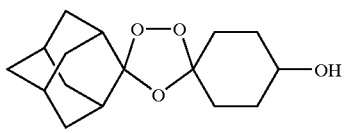
OZ32
280.36
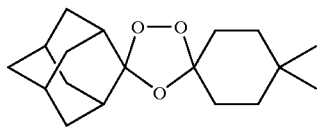
OZ33
292.41

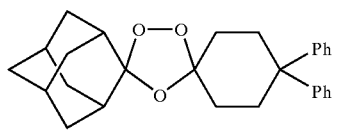
OZ34
MW 416.55
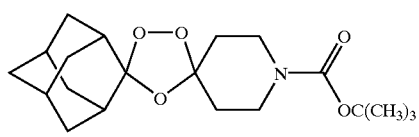
OZ35
MW 365.46
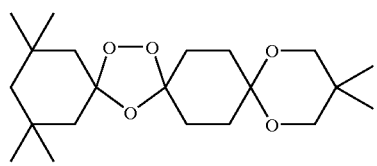
OZ36
MW 368.51
OZ Series 5 (OZ37–OZ45)
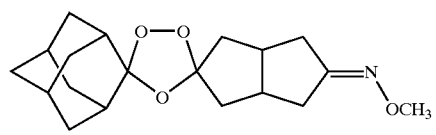
OZ37
MW 333.42
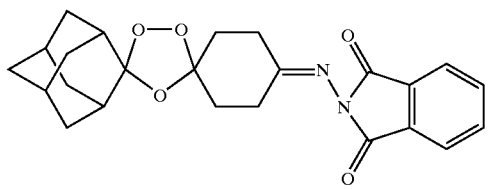
OZ38
MW 422.47
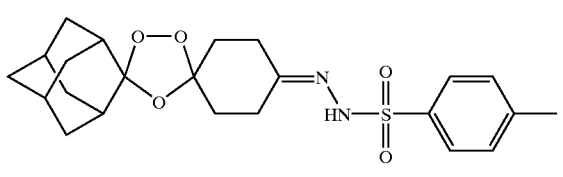
OZ39
MW 446.56
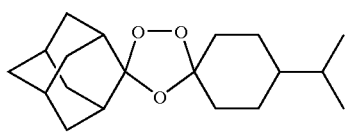
OZ40
MW 306.44
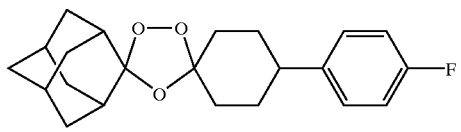
OZ41
MW 358.45
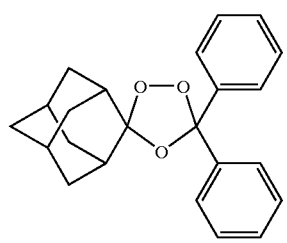
OZ42
MW 348.43
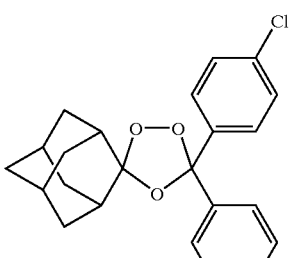
OZ43
MW 417.32
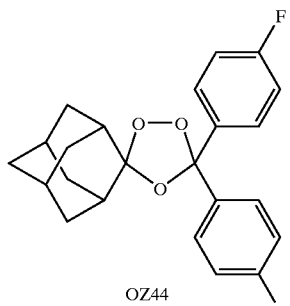
OZ44
MW 384.42
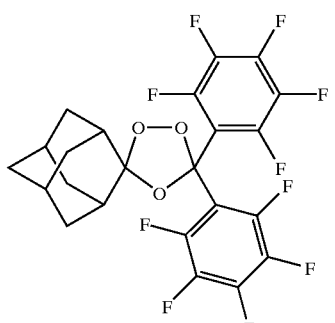
OZ45
MW 528.34

OZ Series 6 (OZ46–OZ54)
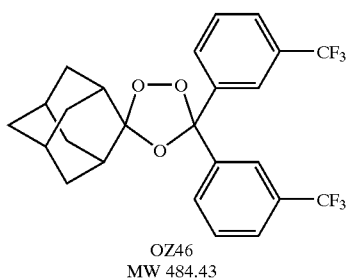
OZ46
MW 484.43
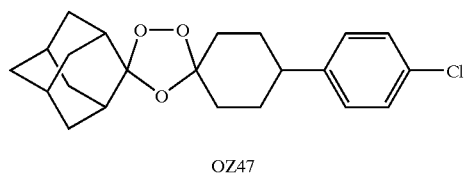
OZ47
MW 374.90
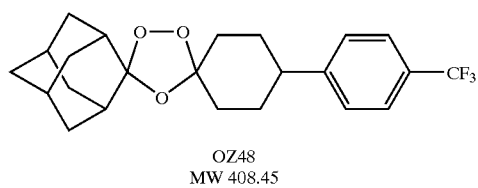
OZ48
MW 408.45
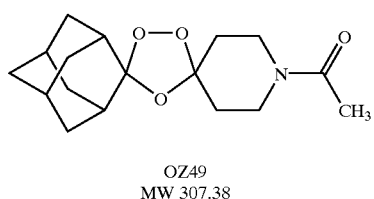
OZ49
MW 307.38
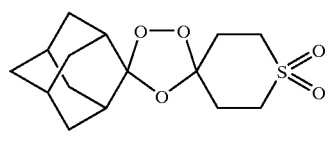
OZ50
MW 314.40
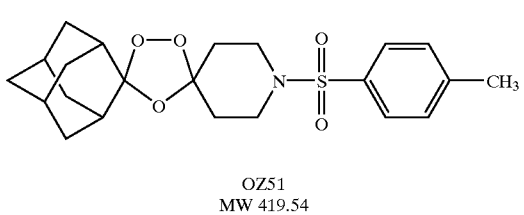
OZ51
MW 419.54
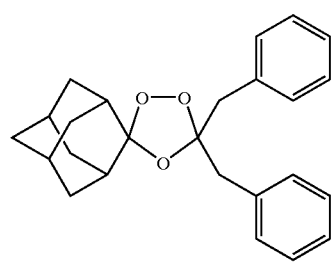
OZ52
MW 376.49
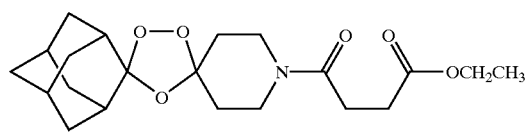
OZ53
MW 393.47
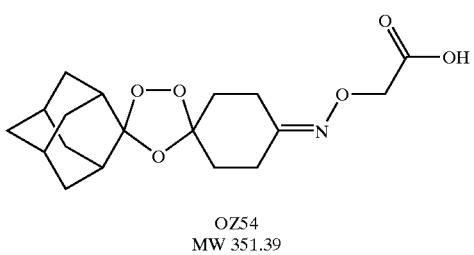
OZ54
MW 351.39
OZ Series 7 (OZ55–OZ63)
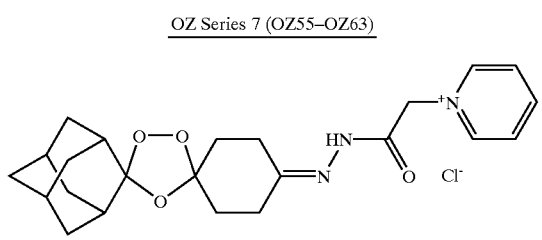
OZ55
MW 447.95
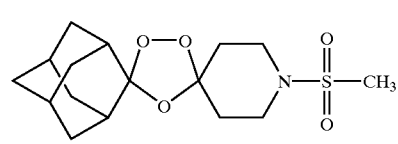
OZ56
MW 343.44
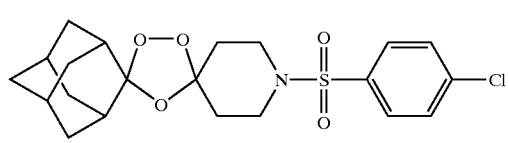
OZ57
MW 439.95
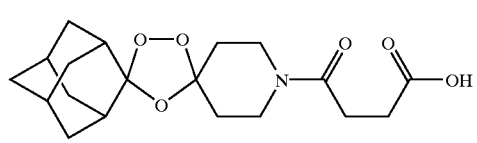
OZ58
MW 365.42
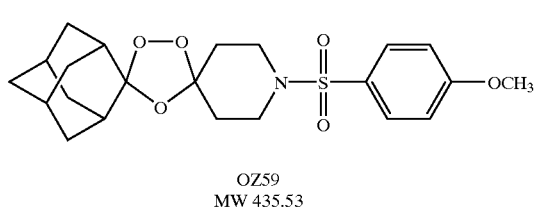
OZ59
MW 435.53

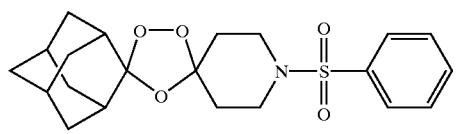
OZ60
MW 405.51
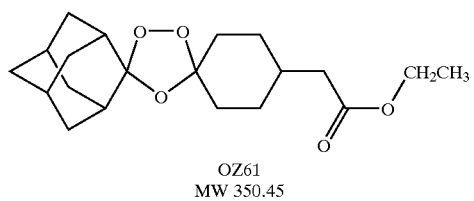
OZ61
MW 350.45
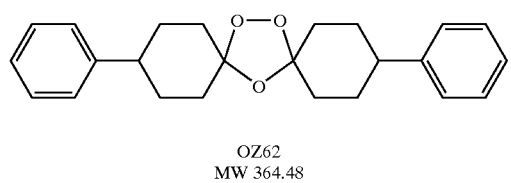
OZ62
MW 364.48
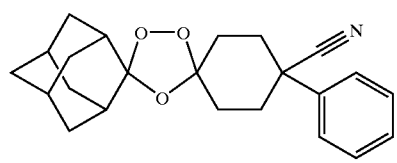
OZ63
MW 365.47
OZ Series 8 (OZ64–OZ72)
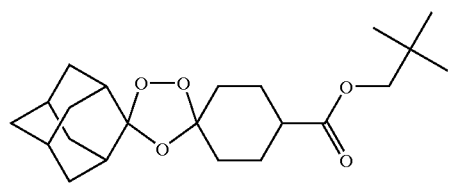
OZ64
MW 378.50
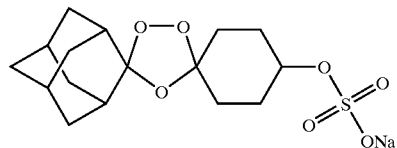
OZ65
MW 382.41
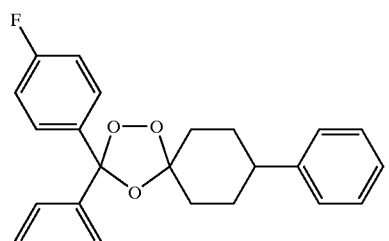
OZ66
MW 408.44
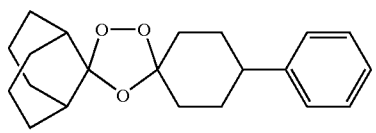
OZ67
MW 328.45
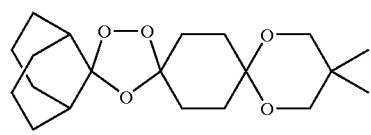
OZ68
MW 352.47
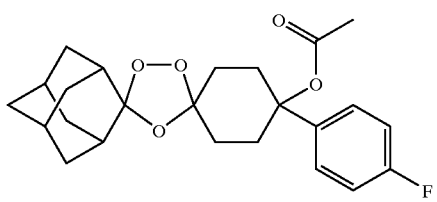
OZ69
MW 416.48
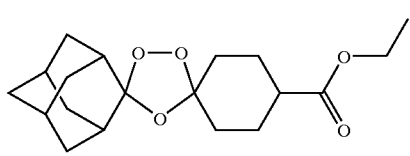
OZ70
MW 336.42
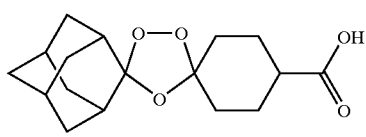
OZ71
MW 308.37
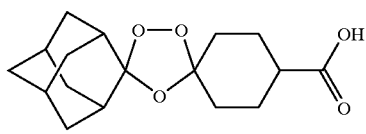
OZ72
MW 308.37

OZ Series 9 (OZ73–OZ81)
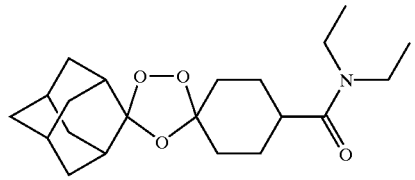
OZ73
MW 363.49
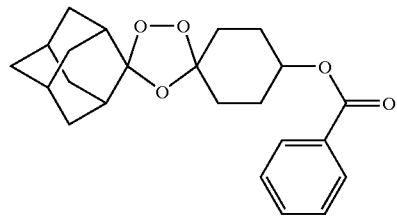
OZ74
MW 384.47
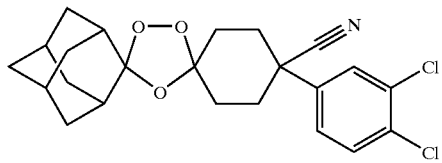
OZ75
MW 434.35
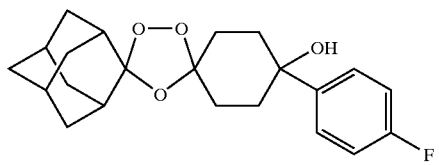
OZ76
MW 374.45
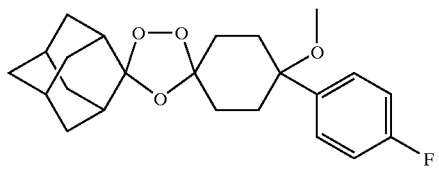
OZ77
MW 388.47
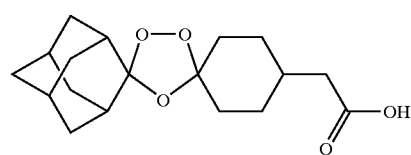
OZ78
MW 322.40
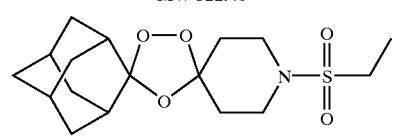
OZ79
MW 357.47
-continued
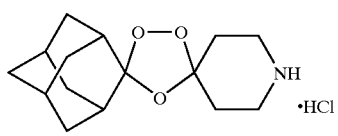
OZ80
MW 301.81
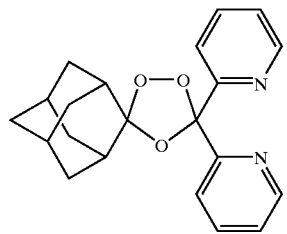
OZ81
MW 350.41
OZ Series 10 (OZ82–OZ90)
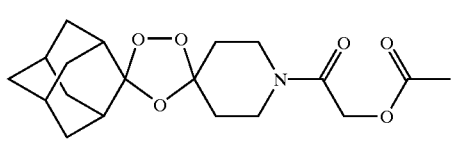
OZ82
MW 365.42
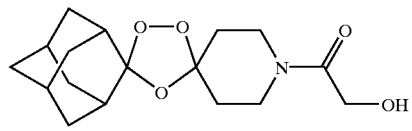
OZ83
MW 323.38
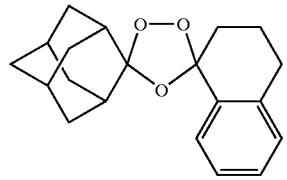
OZ84
MW 312.40
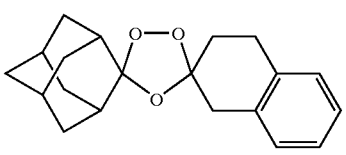
OZ85
MW 312.40
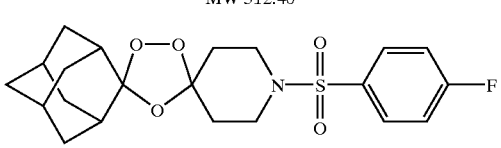
OZ86
MW 423.50

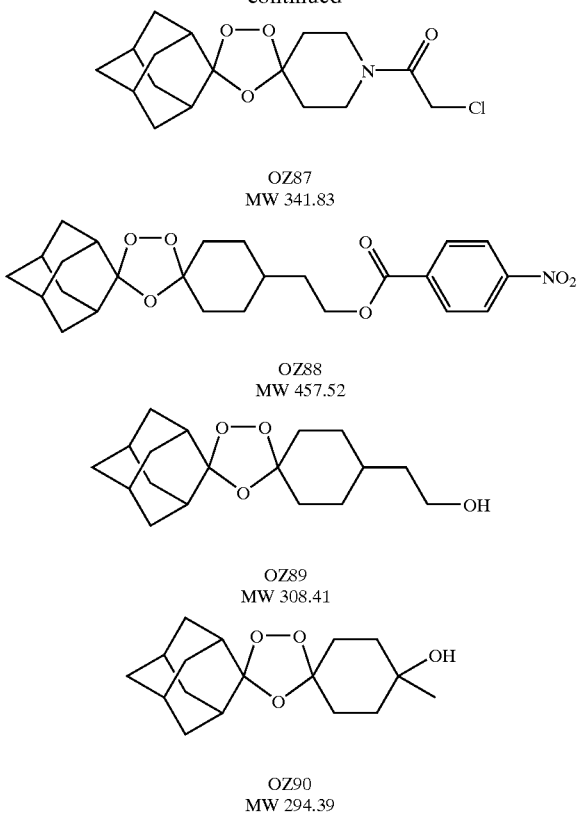

OZ87
MW 341.83

OZ88
MW 457.52

OZ89
MW 308.41

OZ90
MW 294.39

The prototype trioxolanes of this invention are OZ03 and OZ05. Preferred compounds identified thus far include OZ03, OZ05, OZ10, OZ11, OZ15, OZ19, OZ23, OZ24, OZ25, OZ27, OZ31, OZ32, OZ40, OZ41, OZ43, OZ44, OZ47, OZ48, OZ61, OZ63, OZ70, OZ71, OZ77, OZ78, OZ80, OZ83, OZ84, and OZ89. The most preferred compounds are OZ10, OZ11, OZ15, OZ23, OZ25, OZ27, OZ31, OZ41, OZ43, OZ47, OZ63, OZ71, OZ77, OZ78, and OZ89. In general, the highest in vitro potency against malarial parasites is obtained for trioxolanes functionalized or substituted at the 4-position of the spirocyclohexyl ring. As a general rule, non-symmetrical, achiral trioxolanes, such as OZ03, OZ05, OZ10 and OZ11, OZ12, OZ13, OZ18, are also preferred.

Notable features of these spiro and dispiro 1,2,4-trioxolanes in comparison to the artemisinin semisynthetic derivatives are their structural simplicity and ease of synthesis. For example, dispiro trioxolanes may be easily synthesized by the coozonolysis of the O-methyl oximes of cycloalkanones in the presence of the requisite cycloalkanone derivatives according to the method of Griesbaum et al. (1997a; 1997b) as illustrated below for the symmetrical dispiro cyclohexyl trioxolane:

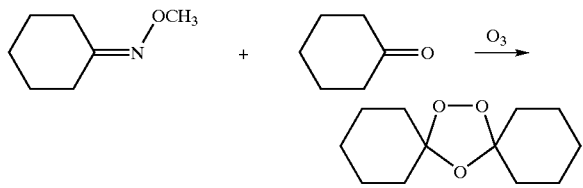

If yields are low in this coozonolysis reaction, yields can improve dramatically when the O-methyloxime and ketone are "reversed." This novel procedure provides a uniquely convenient method to synthesize spiro and dispiro trioxolanes. The trioxolanes may be purified by crystallization or by flash column chromatography. Their structures and purity may be confirmed by analytical HPLC, $^1$H and $^{13}$C NMR, IR, melting point and elemental analysis.

The following cycloalkanone and cycloalkanedione starting materials can be obtained from Aldrich Chemical Co. or from TCI American Organic Chemicals: cyclohexanone, cycloheptanone, cyclooctanone, cyclodecanone, cyclododecanone, 1,3-cyclohexanedione, 1,4-cyclohexanedione, 2,2-dimethylcyclohexanone, 2-adamantanone, bicyclo[3.3.1]nonan-9-one, tetrahydro-4H-pyran-4-one, 1-carboethoxy-4-piperidone, 1-benzoyl-4-piperidone, 1-indanone, 2-indanone, α-tetralone, β-tetralone, bicyclo[3.3.1]nonan-3,7-dione, 1,4-cyclohexanedione-mono-2,2-dimethyltrimethylene ketal, cis-bicyclo[3.3.0]octane-3,7-dione, and 4-carboethoxycyclohexanone.

The cycloalkanone starting materials may also be synthesized. For instance, the inventors have synthesized 4,4-dimethylcyclohexanone and 4,4-diphenylcyclohexanone by catalytic hydrogenation (Augustine, 1958) of the commercially available enones. Also, 2-carboethoxyethylcyclohexanone was synthesized by treatment of the pyrrolidine enamine of cyclohexanone with ethyl acrylate (Stork et al., 1963). Persons skilled in the art can readily ascertain other appropriate means of synthesizing the starting materials and compounds in accordance with this invention.

Differential scanning calorimetry (DSC) experiments for trioxolanes of this invention reveal that these compounds have good thermal stability, comparable to artemisinin.

The spiro and dispiro trioxolane compositions of the present invention may be generally used for the prophylaxis and treatment of malaria. The trioxolane compositions of the present invention are administered along with a pharmaceutically acceptable carrier. Any pharmaceutically acceptable carrier may be generally used for this purpose, provided that the carrier does not significantly interfere with the stability or bioavailability of the trioxolane compounds of this invention.

The trioxolanes of this invention can be administered in any effectively pharmaceutically acceptable form to warm blooded animals, including human and other animal subjects, e.g. in topical, lavage, oral, suppository, parenteral, or infusible dosage forms, as a topical, buccal, sublingual, or nasal spray or in any other manner effective to deliver the agents. The route of administration will preferably be designed to optimize delivery and/or localization of the agents to target cells.

In addition to the active compounds i.e. the trioxolanes, the pharmaceutical compositions of this invention may contain suitable excipients and auxiliaries which facilitate processing of the active compounds into preparations which can be used pharmaceutically. Oral dosage forms encompass tablets, capsules, and granules. Preparations which can be administered rectally include suppositories. Other dosage forms include suitable solutions for administration parenterally or orally, and compositions which can be administered buccally or sublingually.

The pharmaceutical preparations of the present invention are manufactured in a manner which is itself well known in the art. For example the pharmaceutical preparations may be made by means of conventional mixing, granulating, dragee-making, dissolving, lyophilizing processes. The processes to be used will depend ultimately on the physical properties of the active ingredient used.

Suitable excipients are, in particular, fillers such as sugars for example, lactose or sucrose mannitol or sorbitol, cellulose preparations and/or calcium phosphates, for example, tricalcium phosphate or calcium hydrogen phosphate, as well as binders such as starch, paste, using, for example, maize starch, wheat starch, rice starch, potato starch, gelatin, gum tragacanth, methyl cellulose, hydroxypropylmethylcellulose, sodium carboxymethylcellulose, and/or polyvinyl pyrrolidone. If desired, disintegrating agents may be added, such as the above-mentioned starches as well as carboxymethyl starch, cross-linked polyvinyl pyrrolidone, agar, or alginic acid or a salt thereof, such as sodium alginate. Auxiliaries are flow-regulating agents and lubricants, for example, such as silica, talc, stearic acid or salts thereof, such as magnesium stearate or calcium stearate and/or polyethylene glycol. Oral dosage forms may be provided with suitable coatings which, if desired, may be resistant to gastric juices.

For this purpose concentrated sugar solutions may be used, which may optionally contain gum arabic, talc, polyvinylpyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, dyestuffs and pigments may be added to the tablet coatings, for example, for identification or in order to characterize different combination of compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition stabilizers may be added. Possible pharmaceutical preparations which can be used rectally include, for example, suppositories, which consist of a combination of the active compounds with the suppository base. Suitable suppository bases are, for example, natural or synthetic triglycerides, paraffin hydrocarbons, polyethylene glycols, or higher alkanols. In addition, it is also possible to use gelatin rectal capsules which consist of a combination of the active compounds with a base. Possible base material include for example liquid triglycerides, polyethylene glycols, or paraffin hydrocarbons.

Suitable formulations for parenteral administration include aqueous solutions of active compounds in water-soluble or water-dispersible form. In addition, suspensions of the active compounds as appropriate oily injection suspensions may be administered. Suitable lipophilic solvents or vehicles include fatty oils for example, sesame oil, or synthetic fatty acid esters, for example, ethyl oleate or triglycerides. Aqueous injection suspensions may contain substances which increase the viscosity of the suspension, including for example, sodium carboxymethyl cellulose, sorbitol and/or dextran. Such compositions may also comprise adjuvants such as preserving, wetting, emulsifying, and dispensing agents. They may also be sterilized, for example, by filtration through a bacteria-retaining filter, or by incorporating sterilizing agents into the compositions. They can also be manufactured in the form of sterile solid compositions which can be dissolved or suspended in sterile water, saline, or other injectable medium prior to administration.

In addition to administration with conventional carriers, active ingredients may be administered by a variety of specialized delivery drug techniques which are known to those of skill in the art, such as portable infusion pumps.

The trioxolane compositions of the present invention are administered along with a pharmaceutically acceptable carrier in an amount sufficient to prevent malarial infection and/or treat an active infection. The trioxolane compounds of this invention have extremely low toxicity and a low degree of side effects even at high doses. The dosing range of the trioxolane compositions will vary depending on a number of factors, such as whether it is used for prophylaxis or treatment of an active infection, route of administration, dosing schedule, etc. In general, the therapeutic dose of trioxolane may range between about 0.1–1000 mg/kg/day, with between about 1–100 mg/kg/day being preferred. The foregoing doses may be administered as a single dose or may be divided into multiple doses for administration. The trioxolane compositions may be administered once to several times daily. For malaria prevention, a typical dosing schedule could be, for example, 2.0–1000 mg/kg weekly beginning 1–2 weeks prior to malaria exposure taken up until 1–2 weeks post-exposure.

The spiro and dispiro trioxolanes of this invention have been found to be effective in the treatment of schistosomiasis. Schistosomiasis ranks second behind malaria in terms of socioeconomic and public health importance in tropical and subtropical areas. The disease is endemic in 74 developing countries, infecting more than 200 million people in rural agricultural and peri-urban areas. An estimated 500–600 million people worldwide are at risk from the disease.

The major forms of human schistosomiasis are caused by five species of water-borne flatworm, or blood flukes, called schistosomes. One of these species is *Schistosoma mansoni*, which has been reported in 53 countries in Africa, the Eastern Mediterranean, the Caribbean, and South America. The parasites enter the body through contact with infested surface water, primarily among people engaged in agriculture and fishing. The parasites normally infect the host during the cercaria, or larval stage. Once inside the host, the cercaria develop into adults or schistosomes.

Current treatments for schistosomiasis have focused primarily on prophylaxis, i.e. prevention of host infection by cercaria. Currently, praziquantel is the most widely used drug for treatment of schistosomiasis. While artemether has demonstrated activity in the prophylaxis of schistosomiasis, it has not shown any activity against adult *S. mansoni*.

It has now been unexpectedly discovered that the spiro and dispiro trioxolanes of this invention are active against both cercaria and adult *S. mansoni* when administered in the dosages and manner outlined above with respect to treatment of malarial parasites. Preferred compounds identified for use in the treatment of schistosomiasis are the same as those already described, and include OZ03, OZ05, OZ10, OZ11, OZ15, OZ19, OZ23, OZ24, OZ25, OZ27, OZ31, OZ32, OZ40, OZ41, OZ43, OZ44, OZ47, OZ48, OZ61, OZ63, OZ70, OZ71, OZ77, OZ80, OZ83, OZ84, and OZ89. Most preferred compounds are OZ10, OZ11, OZ15, OZ23, OZ25, OZ27, OZ31, OZ41, OZ43, OZ47, OZ63, OZ71, OZ77, Z78, and OZ89. Preferred dosing levels of the spiro and dispiro trioxolanes are about 100–200 mg/kg/day orally.

The Spiro and dispiro trioxolanes of this invention may also have effectiveness in the treatment of cancer. Compounds having an endoperoxide moiety that is reactive with heme and iron have shown an ability to kill cancer cells. (See e.g. U.S. Pat. No. 5,578,637, the disclosure of which is hereby incorporated by reference). As noted with respect to artemisinin, trioxolanes' mechanism of action against malarial parasites is based on the ability of trioxolane compounds to react with the iron in free heme molecules in malaria parasites, with the generation of free radicals leading to cellular destruction. Similarly, trioxolanes are selective against cancer cells due to the higher concentration of transferrin receptors on cancer cell membranes that pick up iron at a higher rate than normal cells. In the presence of the trioxolanes of this invention, the cancer cells will accumulate high concentrations of free radicals, leading to cell death. For cancer treatment, the trioxolanes of this invention may be administered in the doses and manner outlined above.

Other drugs besides trioxolanes which are compatible with the carrier ingredients may also be incorporated into the carrier. Such drugs may be readily ascertained by those of ordinary skill in the art and may include, for instance, antibiotics, other antimalarials, antiinflammatory agents, etc.

It is understood that the present invention contemplates the use of not only the above-stated trioxolane compounds themselves, but their prodrugs which metabolize to the compound and the analogues and biologically active salt forms thereof, as well as optical isomers which provide the same pharmaceutical results.

The following examples are offered to illustrate but not limit the invention. Thus, they are presented with the understanding that various formulation modifications as well as method of delivery modifications may be made and still be within the spirit of the invention.

EXAMPLE 1

General Procedure for the Preparation of 1,2,4-Trioxolanes

Synthesis of O-methyl 2-adamantanone oxime (representative procedure)

To a solution of 2-adamantanone (4.51 g, 30 mmol) in methanol (30 ml) were added pyridine (4.5 ml) and methoxylamine hydrochloride (3.76 g, 45.0 mmol). The reaction mixture was stirred at room. temperature for 48 h, concentrated in vacuo, and diluted with $CH_2Cl_2$ (50 ml) and water (50 ml). The organic layer was separated, and the aqueous layer extracted with $CH_2Cl_2$ (30 ml). The combined organic extracts were washed with 1 M HCl (30 ml×2) and saturated aqueous NaCl (30 ml), and dried over $MgSO_4$. Evaporation in vacuo afforded O-methyl 2-adamantanone oxime (4.77 g, 89%) as a colorless solid. mp 70–71° C.; $^1$H NMR (300 MHz, $CDCl_3$) δ1.60–2.10 (m, 12H), 2.54 (s, 1H), 3.47 (s, 1H), 3.82 (s, 3H).

Ref: Corey, E. J.; Niimura, K.; Konishi, Y.; Hashimoto, S.; Hamada, Y. A New Synthetic Route to Prostaglandins. *Tetrahedron Lett.* 1986, 27, 2199–2202.

O-Methyl cyclohexanone oxime. Yield, 76%; colorless oil; $^1$H NMR (300 MHz, $CDCl_3$) δ1.40–1.80 (m, 6H), 2.20 (t, J=6.0 Hz, 2H), 2.45 (t, J=6.1 Hz, 2H), 3.81 (s, 3H).

O-Methyl cyclododecanone oxime. Yield, 98%; colorless oil; $^1$H NMR (500 MHz, $CDCl_3$) δ1.20–1.49 (m, 14H), 1.50–1.60 (m, 2H), 1.61–1.70 (m, 2H), 2.22 (t, J=6.8 Hz, 2H), 2.35 (t, J=6.6 Hz, 2H), 3.81 (s, 3H).

O-Methyl 3,3,5,5-tetramethylcyclohexanone oxime. Yield, 91%; colorless oil; $^1$H NMR (500 MHz, $CDCl_3$) δ0.96 (s, 6H), 0.97 (s, 6H), 1.33 (s, 2H), 1.95 (s, 2H), 2.20 (s, 2H), 3.80 (s, 3H).

O-Methyl 4-phenylcyclohexanone oxime. Yield, 92%; colorless solid; mp 45–47° C.; $^1$H NMR (500 MHz, $CDCl_3$) δ1.57–1.76 (m, 2H), 1.82–1.92 (m, 1H), 1.99–2.13 (m, 2H), 2.19–2.30 (m, 1H), 2.47–2.56 (m, 1H), 2.72–2.81 (m, 1H), 3.32–3.42 (m, 1H), 3.85 (s, 3H), 7.17–7.34 (m, 5H).

O-Methyl bicyclo[3.3.1]nonan-9-one oxime. Yield, 96%; colorless oil; $^1$H NMR (500 MHz, $CDCl_3$) δ1.46–1.62 (m, 2H), 1.72–2.11 (m, 10H), 2.47 (br s, 1H), 3.40 (br s, 1H, 3.82 (s, 3H).

1-(p-Toluenesulfonyl)-4-piperidone. To a solution of 4-piperidone monohydrate hydrochloride (7.68 g, 50 mmol) in methylene chloride (50 ml) were added sequentially p-toluenesulfonyl chloride (10.50 g, 55.07 mmol) and triethylamine (21 ml). The mixture was stirred at room temperature for 16 h before being quenched with water (100 ml). The organic layer was washed with 1 M HCl (100 ml) and brine (100 ml), and dried over sodium sulfate. Evaporation of the solvent gave the desired ketone (8.60 g, 68%) as a colorless solid. mp 130–132° C.; $^1$H NMR (500 MHz, $CDCl_3$) δ2.40 (s, 3H), 2.58 (t, J=6.4 Hz, 4H), 3.38 (t, J=6.4 Hz, 4H), 7.35 (d, J=7.8 Hz, 2H), 7.68 (d, J=8.3 Hz, 2H).

1-[3-(Ethoxycarbonyl)propionyl]-4-piperidone. To a solution of 4-piperidone monohydrate hydrochloride (7.68 g, 50 mmol) and triethylamine (21 ml) in methylene chloride (100 ml) was added 3-(ethoxycarbonyl)propionyl chloride (9.87 g, 60 mmol) at 0° C. over a period of 10 min. The mixture was stirred at room temperature for 16 h before being quenched with water (100 ml). The organic layer was separated and the aqueous layer was extracted with methylene chloride (100 ml). The combined organic layers were washed with 1M HCl (100 ml), saturated aqueous sodium bicarbonate (100 ml), and brine (100 ml), dried over sodium sulfate, and concentrated. Purification by flash chromatography (silica gel, 30% ether in hexanes) gave the desired ketone (3.80 g, 33%) as a light yellow oil. $^1$H NMR (500 MHz, $CDCl_3$) δ1.27 (t, J=7.3 Hz, 3H), 2.48 (t, J=6.4Hz, 2H), 2.53 (t, J=6.4 Hz, 2H), 2.68 (s, 4H), 3.82 (t, J=6.3 Hz, 2H), 3.82 (t, J=6.3 Hz, 2H), 4.16 (q, J=7.3 Hz, 2H).

1,1-Dioxotetrahydrothiopyran-4-one. To a solution of tetrahydrothiopyran-4-one (400 mg, 3.45 mmol) in acetonitrile (5 ml) was added aqueous $Na_2EDTA$ (3 ml, 0.0004 M). A mixture of oxone (6.30 g, 10.30 mmol) and sodium bicarbonate (2.70, 32 mmol) was added in small portions to the above solution over a period of 20 min. The slurry was stirred for another 1 h before being quenched with methylene chloride. The organic solvent was decanted and the solid residue was triturated with ethyl acetate (3×25 ml). The combined organic layers were dried over sodium sulfate and concentrated to give the desired ketone (0.37 g, 73%) as a colorless solid. mp 170–172° C. (lit. 168–170° C.); $^1$H NMR (500 MHz, $CDCl_3$) 2.99 (t, J=6.8 Hz, 4H), 3.39 (t, J=6.8 Hz, 4H). Ref: Yang, D.; Yip, Y.-C.; Jiao, G.-S.; Wong, M.-K. Design of Efficient Ketone Catalysts for Epoxidation by Using the Field Effect. *J. Org. Chem*, 1998, 63, 8952–8956.

Synthesis of 1-benzenesulfonyl-4-piperidone (Representative Procedure)

To a solution of 4-piperidone monohydrate hydrochloride (4.59 g, 30 mmol), triethylamine (12.5 ml, 90 mmol) in $CH_2Cl_2$ (50 ml) was added benzenesulfonyl chloride (5.30 g, 30 mmol). The mixture was stirred at 25° C. for 16 h. After evaporation of solvents, the residue was triturated with water (100 ml), filtered, and further purified by recrystallization from hexanes/$CH_2Cl_2$ (3:1) to afford the desired ketone (5.97 g, 83%) as a colorless solid. mp 116–118° C.; $^1$H NMR (500 MHz, $CDCl_3$) δ2.54 (t, J=6.4Hz, 4H), 3.41(t, J=6.4Hz, 4H), 7.58 (d, J =7.8 Hz, 2H), 7.63 (t, J=7.0 Hz, 1H), 7.81 (d, J=7.8 Hz, 2H).

1-(4-Methoxybenzenesulfonyl)-4-piperidone. Yield, 77%; colorless solid; mp 130–132° C.; $^1$H NMR (500 MHz, CDCl$_3$) δ2.56 (t, J=6.4 Hz, 4H), 3.38 (t, J=6.3 Hz, 4H), 3.95 (s, 3H), 7.00 (d, J=8.2 Hz, 2H), 7.75 (d, J=8.2 Hz, 2H).

1-(4-Chlorobenzenesulfonyl)-4-piperidone. Yield, 73%; colorless solid; mp 166–168° C.; $^1$H NMR (500 MHz, CDCl$_3$) δ2.55 (t, J=6.4 Hz, 4H), 3.41 (t, J=6.4 Hz, 4H), 7.54 (d, J=8.3 Hz, 2H), 7.81 (d, J=8.4 Hz, 2H).

1-Methanesulfonyl-4-piperidone. To a suspension of 4-piperidone monohydrate hydrochloride (2.0 g, 13 mmol) and K$_2$CO$_3$ (9.0 g, 65.2 mmol) in acetone (40 ml) was added methanesulfonyl chloride (5.96 g, 52.1 mmol) at 0–5° C. The mixture was stirred at 25° C. for 24 h. The solid material was removed by filtration, and the filtrate was concentrated to dryness. The residue was purified by flash chromatography (silica gel, 80% ether in hexanes) to afford the desired ketone (1.20 g, 52%) as a colorless solid. mp 102–104° C.; $^1$H NMR (500 MHz, CDCl$_3$) δ2.58 (t, J=6.4 Hz, 4H), 2.90 (s, 3H), 3.60 (t, J=6.4 Hz, 4H).

Ethoxycarbonylmethylene triphenylphosphorane. To a solution of triphenylphosphine (26.20 g, 100 mmol) in benzene (150 ml) was added ethyl bromoacetate (16.70 g, 100 mmol) at 0–5° C. The mixture was kept at room temperature for 16 h. The resulting phosphonium salt was filtered, washed with benzene (100 ml), and dried. To a solution of the solid in water (200 ml) was added benzene (200 ml), followed by 10% NaOH solution (100 ml). The organic layer was separated, and the aqueous layer was extracted with benzene (200 ml). The combined organic layers were washed with water (100 ml) and brine (100 ml), concentrated to 50 ml in vacuo, and poured onto hexane (200 ml). The precipitate was filtered and dried to afford the desired phosphorane (28.00 g, 80%) as a colorless solid. mp 128–130° C. 4-Oxocyclohexylideneacetic acid ethyl ester. To a solution of 1,4-cyclohexanedione (5.00 g, 44.64 mmol) in benzene (100 ml) was added the ylide (15.55 g, 44.68 mole). The mixture was heated under reflux for 12 h. After removal of the solvent by evaporation, the residue was purified by flash chromatography (silica gel, 5% ethyl acetate in hexanes) to afford the ketone ester (5.80 g, 71%) as a colorless oil. $^1$H NMR (500 MHz, CDCl$_3$) δ1.26 (t, J=6.4 Hz, 3H), 2.42–2.50 (m, 4H,), 2.60–2.66 (m, 2H), 3.12–3.20 (m, 2H), 4.16 (q, J=6.4 Hz, 2H), 5.86 (s, 1H).

4-Oxocyclohexaneacetic acid ethyl ester. To a solution of the unsaturated ester (2.50 g, 13.74 mmol) in ethanol (25 ml) was added Raney nickel (1.0 g). The mixture was stirred at room temperature under H$_2$ (balloon) for 24 h. After the catalyst was removed by filtration, the filtrate was concentrated to give the alcohol ester, which was used for the Jones' oxidation without further purification. To a solution of the above residue in acetone (20 ml) at 0° C. was added Jones' reagent (6 ml), prepared by dissolving CrO$_3$ (27.20 g) in concentrated sulfuric acid (25 ml) and further diluting the solution to 100 ml with water. The reaction was stirred at 0° C. for 2 h before being quenched with isopropanol (3 ml). The organic solvent was removed in vacuo and the residue was diluted with ether (100 ml) and washed with water (50 ml) and brine (50 ml). The organic layer was dried over MgSO$_4$ and concentrated to afford the ketone ester (1.80 g, 71%) as a colorless oil. $^1$H NMR (500 MHz, CDCl$_3$) δ1.26 (t, J=6.4 Hz, 3H), 1.44–1.48 (m, 3H), 2.08–2.10 (m, 2H), 2.29–2.31 (d, J=8.3 Hz, 2H), 2.39–2.40 (m, 4H), 4.18 (q, J=6.4 Hz, 2H).

4-Oxocyclohexanecarboxylic acid. A mixture of ethyl 4-oxocyclohexanecarboxylate (1.74 g, 10 mmol), methanol (25 ml), and 17% aq. KOH (5 ml) was heated at 50° C. for 1.5 h. After being cooled to room temperature, the reaction mixture was acidified to pH 3 with conc. HCl, concentrated to 10 ml under reduced pressure, and extracted with chloroform (3×15 ml). The combined organic layers were dried over MgSO$_4$, filtered, and concentrated to afford the desired ketone acid (1.30 g, 91%) as a colorless solid. mp 62–64° C.; $^1$H NMR (500 MHz, CDCl$_3$) δ2.05–2.10 (m, 2H), 2.23–2.27 (m, 2H), 2.35–2.41 (m, 2H), 2.49–2.54 (m, 2H), 2.80–2.84 (m, 1H).

Neopentyl 4-oxocyclohexanecarboxylate. To a solution of 4-oxocyclohexanecarboxylic acid (852 mg, 6 mmol), triphenylphosphine (1.59 g, 6 mmol), and neopentyl alcohol (635 mg, 7.2 mmol) in dry THF (18 ml) at 0° C. was added dropwise a solution of diethyl azodicarboxylate (0.96 ml, 6 mmol) in dry THF (7.5 ml). The reaction was stirred at rt overnight before being quenched by addition of saturated aqueous NaHCO$_3$ (50 ml). The aqueous phase was separated and extracted with CH$_2$Cl$_2$ (2×30 ml). The organic extracts were combined, dried over MgSO$_4$, and concentrated in vacuo. The residue was diluted with ether (10 ml) and petroleum ether (20 ml) and filtered to remove triphenylphosphine oxide. The solvent was removed in vacuo and the residue was purified by chromatography (20% ether in petroleum ether) to afford the desired ketone ester (820 mg, 65%) as a colorless oil. $^1$H NMR (500 MHz, CDCl$_3$) δ0.96 (s, 9H), 2.04–2.07 (m, 2H), 2.22–2.25 (m, 2H), 2.34–2.40 (m, 2H), 2.46–2.50 (m, 2H), 2.80 (m, 1H), 3.82 (s, 2H).

4-Hydroxy-4-(4-fluorophenyl)cyclohexanone ethylene ketal. To a 500 ml round-bottom flask equipped with a mechanical stirrer, condenser and addition funnel were added magnesium turnings (3.50 g, 140 mmol) and enough THF to cover the Mg. A solution of 1-bromo-4-fluorobenzene (12.45 g, 70.43 mmol) in THF (90 ml) was added dropwise at such a rate that the reaction maintained a gentle reflux following reaction-initiation (the initiation may be accomplished by warming the flask). After the mixture was refluxed for an additional 2.5 h, a solution of 1,4-cylohexanedione monoethylene ketal (10.00 g, 64.03 mmol) in THF (75 ml) was added dropwise. The mixture was kept at refluxing for an additional 2 h before being quenched with saturated ammonium chloride solution (7 ml). After removal of the magnesium salts by filtration, the filtrate was concentrated to dryness. The residue was dissolved in CHCl$_3$ and washed with water and brine. The organic layer was separated, dried over MgSO$_3$, and concentrated. The residue was purified by flash chromatography (30% ether in petroleum ether) to afford the desired alcohol (13.50 g, 87%) as a colorless solid. mp 133–134° C. $^1$H NMR (500 MHz, CDCl$_3$) δ1.69 (d, J=11.7 Hz, 2H), 1.79 (d, J=12.2 Hz, 2H), 2.05–2.18 (m, 4H), (m, 4H), 7.02 (t, J=8.3, 2H), 7.47–7.50 (m, 2H).

4-Hydroxy-4-(4-fluorophenyl)cyclohexanone. A mixture of 4-hydroxy-4-(4-fluorophenyl)cyclohexanone ethylene ketal (7.20 g, 28.6 mmol), THF (125 ml) and 5% aq. HCl (65 ml) was refluxed for 14 h. The reaction mixture was cooled to rt, concentrated to 60 ml, and extracted with CH$_2$Cl$_2$ (3×60 ml). The combined organic layers were dried over MgSO$_4$ and concentrated in vacuo. The residue was purified by crystallization from hexanes to afford the desired alcohol ketone (5.30 g, 89%) as a colorless solid. mp 111–114° C. (lit. 115–117° C.). $^1$H NMR (500 MHz, CDCl$_3$) δ2.17–2.20 (m, 2H), 2.23–2.29 (m, 2H), 2.32–2.37 (m, 2H), 2.87–2.94 (m, 2H), 7.04–7.07 (m, 2H), 7.48–7.51 (m, 2H).

4-Acetoxy-4-(4-fluorophenyl)cyclohexanone. To a solution of 4-hydroxy-4-(4-fluorophenyl)cyclohexanone (520 mg, 2.5 mmol), pyridine (2 ml) and 4-dimethylaminopyridine (46 mg) in CH$_2$Cl$_2$ (25 ml) at 0° C. was added dropwise a solution of acetic anhydride (1 ml) in CH$_2$Cl$_2$ (5 ml). The mixture was warmed to room temperature and stirred for 28 h before being quenched with water (30 ml). The organic phase was washed with 1 M HCl (2×30 ml) and brine (30 ml), dried over $MgSO_3$, and concentrated in vacuo. The residue was purified by flash chromatography (25% ether in petroleum ether) to afford the desired ketone (510 mg, 82%) as a colorless solid. mp 113–115° C. $^1$H NMR (500 MHz, $CDCl_3$) δ2.11 (s, 3H), 2.20 (m, 2H), 2.43 (m, 2H), 2.68 (m, 2H), 2.86 (m, 2H), 7.05 (t, J=8.3, 2H), 7.35–7.38 (m, 2H).

General Procedure for the Preparation of 1,2,4-trioxolanes

Ozone was produced with an OREC ozone generator (0.6 L/min $O_2$, 60 V), passed through an empty gas washing bottle that was cooled to −78° C., and bubbled through a solution of an O-methyl ketone oxime and a ketone in pentane/$CH_2Cl2$ at 0° C. O-methyl oximes of cyclohexanone, 2-adamantanone, and 3,3,5,5-tetramethylcyclohexanone (1 mmol) were consumed within 3 min while O-methyl cyclododecanone oxime (1 mmol) required 6 min to disappear. After completion, the solution was flushed with oxygen for 5 min before being concentrated in vacuo at room temperature to give a residue that was purified by flash chromatography.

7,14,15-Trioxadispiro[5.1.5.2]pentadecane (OZ01). A solution of O-methyl cyclohexanone oxime (1.27 g, 10 mmol) and cyclohexanone (1.96 g, 20 mmol) in pentane (100 ml) was treated with ozone according to the general procedure. The crude product was purified by flash chromatography (silica gel, 2% ether in petroleum ether) to afford trioxolane OZ01 (1.23 g, 58%) as a colorless oil. $^1$H NMR (300 MHz, $CDCl_3$) δ1.20–2.00 (m, 20H); $^{13}$C NMR (75 MHz, $CDCl_3$) δ23.80, 24.91, 34.65, 108.84.

3-Oxo-7,14,15-trioxadispiro[5.1.5.2]pentadecane (OZ02). A solution of O-methyl cyclohexanone oxime (1.27 g, 10 mmol) and 1,4-cyclohexanedione (2.24 g, 20 mmol) in pentane (60 ml) and $CH_2Cl_2$ (40 ml) was treated with ozone according to the general procedure. The crude product was purified by flash chromatography (silica gel, 10% ether in petroleum ether) to afford trioxolane OZ02 (0.88 g, 39%) as a colorless solid. mp 52–54° C. (lit. 53° C.); $^1$H NMR (300 MHz, $CDCl_3$) δ1.30–1.90 (m, 10H), 2.16 (t, J=7.0 Hz, 4H), 2.53 (t, J=7.0 Hz, 4H); $^{13}$C NMR (75 MHz, $CDCl_3$) δ23.77, 24.81, 32.97, 34.41, 37.78, 106.89, 110.03, 203.07. Ref: Griesbaum, K.; Liu, X.; Kassiaris, A.; Scherer, M. Ozonolyses of O-Alkylated Ketoximes in the Presence of Carbonyl Groups: A Facile Access to Ozonides. *Libigs Ann./Recueil* 1997, 1381–1390.

Adamantane-2-spiro-3'-1',2',4'-trioxaspiro[4.5]decane (OZ03). A solution of O-methyl cyclohexanone oxime (1.27 g, 10 mmol) and 2-adamantanone (3.00 g, 20 mmol) in pentane (200 ml) was treated with ozone according to the general procedure. The crude product was purified by flash chromatography (silica gel, 2% ether in petroleum ether) to afford trioxolane OZ03 (1.55 g, 46%) as a colorless oil. $^1$H NMR (300 MHz, $CDCl_3$) δ1.30–2.10 (m, 24H); $^{13}$C NMR (75 MHz, $CDCl_3$) δ23.84, 24.97, 26.48, 26.89, 34.73, 34.77, 34.81, 36.40, 36.79, 108.85, 111.15. Ref: Keul, H. Über Konstitution und Entstehung der Ozonide von Bis-adamantyliden und von Bis-bicyclo[3.3.1]non-9-yliden. *Chem. Ber.* 1975, 108, 1207–1217.

Adamantane-2-spiro-3'-1',2',4'-trioxolane-5'-spiro-2''-adamantane (OZ04). A solution of O-methyl 2-adamantanone oxime (1.80 g, 10 mmol) and 2-adamantanone (3.00 g, 20 mmol) in pentane (200 ml) was treated with ozone according to the general procedure. The crude product was purified by flash chromatography (silica gel, 2% ether in petroleum ether) to afford trioxolane OZ04 (1.38 g, 40%) as a colorless solid. mp 150° C. dec (lit. 140–144° C. dec); $^1$H NMR (300 MHz, $CDCl_3$) δ1.50–2.20 (m, 28H); $^{13}$C NMR (75 MHz, $CDCl_3$) δ26.52, 26.97, 34.70, 34.95, 36.58, 36.81, 111.19. Ref: Keul, H. Über Konstitution und Entstehung der Ozonide von Bis-adamantyliden und von Bis-bicyclo[3.3.1]non-9-yliden. *Chem. Ber.* 1975, 108, 1207–1217.

Adamantane-2-spiro-3'-8'-oxo-1',2',4'-trioxaspiro[4.5] decane (OZ05). A solution of O-methyl 2-adamantanone oxime (1.80 g, 10 mmol) and 1,4-cyclohexanedione (2.24 g, 20 mmol) in pentane (60 ml) and $CH_2Cl_2$ (40 ml) was treated with ozone according to the general procedure. The crude product was purified by flash chromatography (silica gel, 10% ether in petroleum ether) to afford trioxolane OZ05 (1.23 g, 44%) as a colorless solid. mp 126–128° C. (ethanol/$H_2O$ 1:1); $^1$H NMR (300 MHz, $CDCl_3$) δ1.70–2.05 (m, 14H), 2.16 (t, J=7.2 Hz, 4H), 2.53 (t, J=7.2 Hz, 4H); $^{13}$C NMR: (75 MHz, $CDCl_3$) δ26.38, 26.79, 33.08, 34.74, 34.84, 36.26, 36.67, 37.84, 106.94, 112.43, 209.36. Anal. Calcd for $C_{16}H_{22}O_4$: C, 69.04; H, 7.97. Found: C, 69.25; H, 7.79.

1-Fluoro-7,14,15-trioxadispiro[5.1.5.2]pentadecane (OZ06). A solution of O-methyl cyclohexanone oxime (0.64 g, 5 mmol) and 2-fluorocyclohexanone (0.58 g, 5 mmol) in pentane (50 ml) was treated with ozone according to the general procedure. The crude product was purified by flash chromatography (silica gel, 4% ether in petroleum ether) to afford trioxolane OZ06 (0.68 g, 59%, 2.4:1 mixture of two diastereomers) as a colorless oil. $^1$H NMR (300 MHz, $CDCl_3$) δ1.30–2.20 (m, 18H), 4.54 (ddd, J=48.9, 5.6, 2.9 Hz, 1H); $^{13}$C NMR (75 MHz, $CDCl_3$) δ19,48 (d, J=3.9 Hz), 22.67, 23.55, 23.82, 24.78, 29.36 (d, J=20.4 Hz), 30.97, 33.76, 34.75, 89.86 (d, J=179.8 Hz), 106.38 (d, J=20.3 Hz), 110.24 assigned to the major isomer; 19.12 (d, J=3.3 Hz), 22.73, 23.44, 23.93, 24.80, 28.31 (d, J=20.2 Hz), 29.13, 33.47, 34.91, 88.06 (d, J=180.0 Hz), 106.45 (d, J=23.0 Hz), 109.68 assigned to the minor isomer; $^{19}$F NMR (282 MHz, $CDCl_3$) δ−19.2 (bs, 2.4F) assigned to the major isomer; −13.2 (t, J=43.5 Hz, 1F) assigned to the minor isomer. Anal. Calcd for $C_{12}H_{19}FO_3$: C, 62.59; H, 8.32. Found: C, 62.59; H, 8.21.

1-[2-(Ethoxycarbonyl)ethyl]-7,14,15-trioxadispiro [5.1.5.2]pentadecane (OZ07). A solution of O-methyl cyclohexanone oxime (1.27 g, 10 mmol) and 2-[2-(ethoxycarbonyl)ethyl]cyclohexanone (3.96 g, 20 mmol) in pentane (100 ml) was treated with ozone according to the general procedure. The crude product was purified by flash chromatography (silica gel, 6% ether in petroleum ether) to afford trioxolane OZ07 (1.77 g, 57%, 1:1 mixture of two diastereomers) as a colorless oil. $^1$H NMR (300 MHz, $CDCl_3$) δ1.27 (t, J=7.2 Hz, 3H), 1.20–1.89 (m, 19H), 1.90–2.20 (m, 2H), 2.21–2.50 (m, 2H), 4.14 (q, J=7.1 Hz, 2H); $^{13}$C NMR (75 MHz, $CDCl_3$) δ14.16, 22.74, 23.35, 23.48, 23.56, 23.63, 23.92, 23.95, 24.80, 24.84, 28.52, 28.81, 32.59, 32.65, 33.85, 34.14, 34.62, 34.68, 34.74, 41.14, 42.00, 60.14, 108.84, 108.95, 110.38, 110.53, 173.63, 173.67. Anal. Calcd for $C_{17}H_{28}O_5$: C, 65.36; H, 9.03. Found: C, 65.60; H, 8.94.

Adamantane-2-spiro-3'-6'-[2'-(ethoxycarbonyl)ethyl]-1',2',4'-trioxaspiro[4.5]decane (OZ08). A solution of O-methyl 2-adamantanone oxime (1.80 g, 10 mmol) and 2-[2-(ethoxycarbonyl)ethyl]cyclohexanone (3.96 g, 20 mmol) in pentane (100 ml) was treated with ozone according to the general procedure. The crude product was purified by flash chromatography (silica gel, 6% ether in petroleum ether) to afford trioxolane OZ08 (2.10 g, 58%, 4:3 mixture of two diastereomers) as a colorless oil. $^1$H NMR (300 MHz, CDCl$_3$) δ1.26 (t, J=7.2 Hz, 3H), 1.20–2.19 (m, 25H), 2.21–2.49 (m, 2H), 4.13 (q, J=7.2 Hz, 2H); $^{13}$C NMR (75 MHz, CDCl$_3$) δ14.08, 22.93, 23.37, 23.46, 23.48, 23.65, 23.89, 26.29, 26.34, 26.71, 28.42, 28.89, 32.46, 32.52, 34.06, 34.20, 34.31, 34.60, 34.67, 35.18, 35.25, 35.74, 35.99, 36.63, 36.80, 41.15, 42.00, 60.01, 110.34, 110.47, 111.07, 111.13, 173.49, 173.56. Anal. Calcd for C$_{21}$H$_{32}$O$_5$: C, 69.20; H, 8.85. Found: C, 69.09; H, 8.63.

7,12,19,20,23,24-Hexaoxatetraspiro[5.1.2.1.5.2.2.2]tetracosane (OZ09). A solution of O-methyl cyclohexanone oxime (1.27 g, 10 mmol) and 1,4-cyclohexanedione (0.37 g, 3.3 mmol) in pentane (40 ml) and CH$_2$Cl$_2$ (20 ml) was treated with ozone according to the general procedure. The crude product was purified by flash chromatography (silica gel, 4% ether in petroleum ether) to afford trioxolane OZ09 (0.56 g, 50%, 1:1 mixture of two diastereomers) as a colorless solid. mp 83–84° C. (lit. 83.5° C.); $^1$H NMR (300 MHz, CDCl$_3$) δ1.25–1.83 (m, 20H), 1.92 (s, 8H); $^{13}$C NMR (75 MHz, CDCl$_3$) δ23.75, 24.83, 24.86, 31.38, 34.46, 107.50, 107.57, 109.34. Ref: Griesbaum, K.; Liu, X.; Dong, Y. Diozonides from Coozonolyses of Suitable O-Methyl Oximes and Ketoses. *Tetrahedron* 1997, 53, 5463–5470.

Adamantane-2-spiro-3'-1',2',4',9',12'-pentaoxadispiro[4.2.4.2]tetradecane (OZ10). A solution of O-methyl 2-adamantanone oxime (1.80 g, 10 mmol) and 1,4-dioxaspiro[4.5]decan-8-one (1.56 g, 10 mmol) in pentane (90 ml) and CH$_2$Cl$_2$ (10 ml) was treated with ozone according to the general procedure. The crude product was purified by flash chromatography (silica gel, 4% ether in petroleum ether) to afford trioxolane OZ10 (1.06 g, 33%) as a colorless solid. mp 84–85° C. (ethanol); $^1$H NMR (300 MHz, CDCl$_3$) δ1.64–2.13 (m, 22H), 3.97 (s, 4H); 13C NMR (75 MHz, CDCl$_3$) δ26.39, 26.80, 31.66, 32.01, 34.68, 34.77, 36.26, 36.70, 64.30, 107.78, 107.97, 111.49. Anal. Calcd for C$_{18}$H$_{26}$O$_5$: C, 67.06; H, 8.13. Found: C, 67.28; H, 8.35.

Adamantane-2-spiro-3'-11',11'-dimethyl-1',2',4',9',13'-pentaoxadispiro[4.2.5.2]pentadecane (OZ11). A solution of O-methyl 2-adamantanone oxime (1.80 g, 10 mmol) and 3,3-dimethyl-1,5-dioxaspiro[5.5]undecan-9-one (1.98 g, 10 mmol) in pentane (100 ml) was treated with ozone according to the general procedure. The crude product was purified by flash chromatography (silica gel, 4% ether in petroleum ether) to afford trioxolane OZ11 (1.43 g, 39%) as a colorless solid. mp 123–125° C. (ethanol); $^1$H NMR (300 MHz, CDCl$_3$) δ0.99 (s, 6H), 1.61–2.14 (m, 22H), 3.51 (s, 4H); $^{13}$C NMR (75 MHz, CDCl$_3$) δ22.66, 26.43, 26.84, 29.41, 30.16, 30.46, 34.73, 34.82, 36.30, 36.75, 70.24, 70.19, 96.67, 108.47, 111.51. Anal. Calcd for C$_{21}$H$_{32}$O$_5$: C, 69.20; H, 8.85. Found: C, 69.17; H, 8.97.

Adamantane-2-spiro-3'-1',2',4'-trioxolane-5'-spiro-3''-7''-oxo-cis-bicyclo[3.3.0]octane (OZ12). A solution of O-methyl 2-adamantanone oxime (1.80 g, 10 mmol) and cis-bicyclo[3.3.0]octane-3,7-dione (2.76 g, 20 mmol) in pentane (60 ml) and CH$_2$Cl$_2$ (40 ml) was treated with ozone according to the general procedure. The crude product was purified by flash chromatography (silica gel, 15% ether in petroleum ether) to afford trioxolane OZ12 (0.51 g, 17%) as a colorless solid. mp 122–124° C. (ethanol/H$_2$O 4:1); $^1$H NMR (300 MHz, CDCl$_3$) δ1.60–2.05 (m, 16H), 2.13–2.41 (m, 4H), 2.43–2.62 (m, 2H), 2.70–2.93 (m, 2H); $^{13}$C NMR (75 MHz, CDCl$_3$) δ26.43, 26.79, 34.71, 34.84, 35.96, 36.72, 36.97, 41.42, 44.15, 111.82, 117.66, 219.55. Anal. Calcd for C$_{18}$H$_{24}$O$_4$: C, 71.03; H, 7.95. Found: C, 71.18; H, 7.80.

Adamantane-2-spiro-3'-1',2',4'-trioxolane-5'-spiro-3''-7''-oxobicyclo[3.3.1]nonane (OZ13). A solution of O-methyl 2-adamantanone oxime (0.64 g, 3.55 mmol) and bicyclo[3.3.1]nonane-3,7-dione (1.08 g, 7.10 mmol) in pentane (45 ml) and CH$_2$Cl$_2$ (45 ml) was treated with ozone according to the general procedure. The crude product was purified by flash chromatography (silica gel, 30% ether in petroleum ether) to afford trioxolane OZ13 (0.10 g, 9%) as a colorless solid. mp 153–155° C. (ethanol/H$_2$O 1:1); $^1$H NMR (300 MHz, CDCl$_3$) δ1.55–2.10 (m, 20H), 2.32–2.70 (m, 6H); $^{13}$C NMR (75 MHz, CDCl$_3$) δ26.45, 26.66, 28.87, 31.30, 34.32, 34.80, 36.15, 36.79, 39.94, 45.89, 107.15, 113.66, 208.12. Anal. Calcd for C$_{19}$H$_{26}$O$_4$: C, 71.67; H, 8.23. Found: C, 71.68; H, 8.19.

Adamantane-2-spiro-3'-1',2',4'-trioxolane-5'-spiro-8''-11''-oxopentacyclo[5.4.0.0$^{2'',6''}$.0$^{3'',10''}$.0$^{5'',9''}$]undecane (OZ14). A solution of O-methyl 2-adamantanone oxime (1.80 g, 10 mmol) and pentacyclo[5.4.0.0$^{2,6}$.0$^{3,10}$.0$^{5,9}$]undecane-8,11-dione (3.48 g, 20 mm (100 ml) was treated with ozone according to the general procedure. The crude product was purified by flash chromatography (silica gel, 20% ether in petroleum ether) to afford trioxolane OZ14 (0.77 g, 23%) as a colorless solid. mp 106° C. dec (ethanol); $^1$H NMR (300 MHz, CDCl$_3$) δ1.45–2.15 (m, 16H), 2.45–3.05 (m, 8H); $^{13}$C NMR (75 MHz, CDCl$_3$) δ26.36, 26.63, 34.53, 34.56, 35.10, 36.05, 36.33, 36.54, 38.94, 41.07, 41.16, 41.98, 42.52, 45.14, 50.81, 51.80, 112.91, 113.01, 213.36. Anal. Calcd for C$_{21}$H$_{24}$O$_4$: C, 74.09; H, 7.11. Found: C, 74.00; H, 7.29.

Adamantane-2-spiro-3'-8'-methoxyimino-1',2',4'-trioxaspiro[4.5]decane (OZ15). To a solution of OZ05 (0.557 g, 2.0 mmol) in CH$_2$Cl$_2$ (5 ml) and methanol (5 ml) were added pyridine (0.30 ml) and methoxyamine hydrochloride (0.250 g, 3.0 mmol), and the reaction was stirred at room temperature for 24 h. The reaction mixture was concentrated in vacuo to provide a crude residue that was purified by recrystallizations from ethanol/H$_2$O (20 ml, 1:1) and from ethanol/H$_2$O (15 ml, 2:1) to give trioxolane OZ15 (0.51 g, 83%) as a colorless solid. mp 97–99° C. (ethanol/H20 2:1); $^1$H NMR (300 MHz, CDCl$_3$) δ1.60–2.10 (m, 18H), 2.30–2.81 (m, 4H), 3.84 (s, 3H); $^{13}$C NMR (75 MHz, CDCl$_3$) δ21.54, 26.40, 26.81, 28.74, 32.59, 33.85, 34.72, 34.77, 34.84, 36.28, 36.70, 61.15, 107.92, 112.00, 156.93. Anal. Calcd for C$_{17}$H$_{25}$NO$_4$: C, 66.43; H, 8.20; N, 4.56. Found: C, 66.58; H, 8.29; N, 4.41.

Adamantane-2-spiro-3'-8'-hydroxyimino-1',2',4'-trioxaspiro[4.5]decane (OZ16). To a solution of OZ05 (0.557 g, 2.0 mmol) in CH$_2$Cl$_2$ (5 ml) and methanol (5 ml) were added pyridine (0.30 ml) and hydroxylamine hydrochloride (0.210 g, 3.0 mmol), and the reaction was stirred at room temperature for 24 h. The reaction mixture was concentrated in vacuo to provide a crude residue that was purified by recrystallization from ethanol/H$_2$O (20 ml, 1:1) to give trioxolane OZ16 (0.43 g, 73%) as a colorless solid. mp 137–139° C. (ethanol/H$_2$O 1:1); $^1$H NMR (300 MHz, CDCl$_3$) δ1.62–2.10 (m, 18H), 2.32–2.88 (m, 4H), 8.60–8.95 (br s, 1H); $^{13}$C NMR (75 MHz, CDCl$_3$) δ20.97, 26.41, 26.81, 28.72, 32.48, 33.74, 34.74, 34.80, 34.84, 36.29, 36.70, 107.91, 112.06, 157.94. Anal. Calcd for C$_{16}$H$_{23}$NO$_4$: C, 65.51; H, 7.90; N, 4.77. Found: C, 65.65; H, 7.96; N, 4.75.

Adamantane-2-spiro-3'-9'-oxo-1',2',4',8'-tetraoxaspiro[4.6]undecane (OZ17). To a solution of OZ05 (0.84 g, 3.0 mmol) in CH$_2$Cl$_2$ (70 ml) were added NaHCO$_3$ (0.51 g, 6.0 mmol) and 3-chloroperoxybenzoic acid (1.20 g). The reaction was stirred at room temperature for 46 h before being quenched with H$_2$O (60 ml). The aqueous layer was extracted with CH$_2$Cl$_2$ (10 ml×2), and the combined extracts were washed with H$_2$O, dried over MgSO$_4$, and concentrated to give a crude residue that was purified by flash chromatography (silica gel, 40% ether in petroleum ether) to afford trioxolane OZ17 (0.31 g, 35%) as a colorless solid. mp 116–118° C. (ethanol); $^1$H NMR (300 MHz, CDCl$_3$) δ1.62–2.10 (m, 18H), 2.32–2.88 (m, 4H), 8.60–8.95 (br s, 1H); $^{13}$C NMR (75 MHz, CDCl$_3$) δ26.25, 26.65, 28.54, 31.87, 34.62, 34.64, 34.67, 34.71, 36.19, 36.50, 38.35, 63.86, 107.60, 112.89, 25 174.63. Anal. Calcd for C$_{16}$H$_{22}$O$_5$: C, 65.29; H, 7.53. Found: C, 65.48; H, 7.80.

Adamantane-2-spiro-3'-8'-t-butyl-1',2',4'-trioxaspiro[4.5]decane (OZ18). A solution of O-methyl 2-adamantanone oxime (1.80 g, 10 mmol) and 4-tert-butylcyclohexanone (3.09 g, 20 mmol) in pentane (100 ml) was treated with ozone according to the general procedure. The crude product was purified by flash chromatography (silica gel, 2% ether in petroleum ether) to afford trioxolane OZ18 (1.68 g, 52%) as a colorless solid. mp 123–124° C. (ethanol); $^1$H NMR (300 MHz, CDCl$_3$) δ0.84 (s, 9H), 0.89–1.10 (m, 1H), 1.14–1.35 (m, 2H), 1.55–1.85 (m, 12H), 1.86–2.10 (m, 8H); $^{13}$C NMR (75 MHz, CDCl$_3$) δ24.71, 26.49, 26.89, 27.57, 32.27, 34.79, 36.38, 36.82, 46.66, 108.95, 111.12. Anal. Calcd for C$_{20}$H$_{32}$O$_3$: C, 74.96; H, 10.06. Found: C, 75.25; H, 10.06.

Adamantane-2-spiro-3'-8'-benzyloxyimino-1',2',4'-trioxaspiro[4.5]decane (OZ19). To a solution of OZ05 (0.56 g, 2.0 mmol) in CH$_2$Cl$_2$ (5 ml) and methanol (5 ml) were added pyridine (0.30 ml) and O-benzylhydroxylamine hydrochloride (0.48 g, 3.0 mmol), and the reaction was stirred at room temperature for 24 h. The reaction mixture was concentrated in vacuo to provide a crude residue that was purified by recrystallizations from ethanol/H$_2$O (20 ml, 1:1) and from ethanol/H$_2$O (15 ml, 2:1) to give trioxolane OZ19 (0.66 g, 86%) as a colorless solid. mp 62–64° C. (ethanol/H$_2$O 2:1); $^1$H NMR (300 MHz, CDCl$_3$) δ1.60–2.10 (m, 18H), 2.32–2.50 (m, 2H), 2.53–2.67 (m, 1H), 2.72–2.86 (m, 1H), 5.08 (s, 2H), 7.25–7.42 (m, 5H); $^{13}$C NMR (75 MHz, CDCl$_3$) δ21.87, 26.41, 26.81, 28.76, 32.61, 33.87, 34.72, 34.74, 34.79, 34.85, 36.29, 36.70, 75.36, 107.94, 111.99, 127.67, 127.90, 128.31, 137.99, 157.57. Anal. Calcd for C$_{23}$H$_{29}$NO$_4$: C, 72.04; H, 7.62; N, 3.65. Found: C, 72.30; H, 7.49; N, 3.77.

Adamantane-2-spiro-3'-1',2',4'-trioxaspiro[4.11]hexadecane (OZ20). A solution of O-methyl cyclododecanone oxime (2.11 g, 10 mmol) and 2-adamantanone (3.0 g, 20 mmol) in pentane (90 ml) and CH$_2$Cl$_2$ (10 ml) was treated with ozone according to the general procedure. The crude product was purified by flash chromatography (silica gel, 2% ether in petroleum ether) to afford trioxolane OZ20 (1.88 g, 54%) as a colorless solid. mp 73–75° C. (ethanol/H$_2$O 3:1); $^1$H NMR (300 MHz, CDCl$_3$) δ1.18–1.60 (m, 18H), 1.62–2.10 (m, 18H); $^{13}$C NMR (75 MHz, CDCl$_3$) δ20.07, 22.05, 22.37, 25.81, 26.07, 26.49, 26.88, 31.37, 34.76, 34.86, 36.38, 36.79, 111.33, 112.59. Anal. Calcd for C$_{22}$H$_{36}$O$_3$: C, 75.82; H, 10.41. Found: C, 75.65; H, 10.69.

3-Oxo-7,20,21-trioxadispiro[5.1.11.2]heneicosane (OZ21). A solution of O-methyl cyclododecanone oxime (2.11 g, 10 mmol) and 1,4-cyclohexanedione (2.24 g, 20 mmol) in pentane (60 ml) and CH$_2$Cl$_2$ (40 ml) was treated with ozone according to the general procedure. The crude product was purified by flash chromatography (silica gel, 10% ether in petroleum ether) to afford trioxolane OZ21 (1.29 g, 42%) as a colorless solid. mp 78–80° C.; $^1$H NMR (300 MHz, CDCl$_3$) δ1.10–1.65 (m, 18H), 1.70–1.90 (m, 4H), 2.15 (t, J=7.0 Hz, 4H), 2.52 (t, J=7.1 Hz, 4H); $^{13}$C NMR (75 MHz, CDCl$_3$) δ20.03, 22.04, 22.39, 25.76, 26.03, 31.12, 32.92, 37.80, 107.00, 113.73, 209.29. Anal. Calcd for C$_{18}$H$_{30}$O$_4$: C, 69.64; H, 9.74. Found: C, 69.49; H, 9.81.

Adamantane-2-spiro-3'-1',2',4',8'-tetraoxaspiro[4.5]decane (OZ22). A solution of O-methyl 2-adamantanone oxime (0.90 g, 5 mmol) and tetrahydro-4H-pyran-4-one (1.00 g, 10 mmol) in pentane (100 ml) was treated with ozone according to the general procedure. The crude product was purified by flash chromatography (silica gel, 2 to 10% ether in petroleum ether) to afford trioxolane OZ22 (0.87 g, 65%) as a colorless oil. $^1$H NMR (300 MHz, CDCl$_3$) δ1.20–2.30 (m, 18H), 3.50–4.10 (m, 4H); $^{13}$C NMR (75 MHz, CDCl$_3$) δ26.33, 26.73, 34.60, 34.68, 35.43, 36.30, 36.60, 65.67, 105.91, 111.76. Anal. Calcd for C$_{15}$H$_{22}$O$_4$: C, 67.64; H, 8.33. Found: C, 67.83; H, 8.21.

Adamantane-2-spiro-3'-8'-ethoxycarbonyl-1',2',4'-trioxa-8'-azaspiro[4.5]decane (OZ23). A solution of O-methyl 2-adamantanone oxime (0.90 g, 5 mmol) and 1-ethoxycarbonyl-4-piperidone (1.71 g, 10 mmol) in pentane (80 ml) and CH$_2$Cl$_2$ (20 ml) was treated with ozone according to the general procedure. The crude product was purified by flash chromatography (silica gel, 10 to 20% ether in petroleum ether) to afford trioxolane OZ23 (0.43 g, 26%) as a colorless solid. mp 44–46° C. (ethanol/H$_2$O 5:2); 1H NMR (300 MHz, CDCl$_3$) δ1.27 (t, J=7.0 Hz, 3H), 1.60–2.10 (m, 18H), 3.40–3.75 (m, 4H), 4.14 (q, J=7.1 Hz, 2H); $^{13}$C NMR (75 MHz, CDCl$_3$) δ14.66, 26.40, 26.79, 34.35, 34.71, 34.79, 36.35, 36.68, 41.69, 61.42, 106.86, 112.06, 155.33. Anal. Calcd for C$_{18}$H$_{27}$NO$_5$: C, 64.07; H, 8.07; N, 4.15. Found: C, 63.96; H, 7.73; N, 4.15.

Adamantane-2-spiro-3'-8'-benzoyl-1',2',4'-trioxa-8'-azaspiro[4.5]decane (OZ24). A solution of O-methyl 2-adamantanone oxime (0.90 g, 5 mmol) and 1-benzoyl-4-piperidone (2.03 g, 10 mmol) in pentane (60 ml) and CH$_2$Cl$_2$ (40 ml) was treated with ozone according to the general procedure. The crude product was purified by flash chromatography (silica gel, 30 to 50% ether in petroleum ether) to afford trioxolane OZ24 (0.61 g, 33%) as a colorless solid. mp 130–132° C. (ethanol/H$_2$O 1:1); $^1$H NMR (300 MHz, CDCl$_3$) δ1.60–2.15 (m, 18H), 3.51 (br s, 2H), 3.77 (br s, 1H), 3.96 (br s, 1H), 7.30–7.50 (m, 5H); $^{13}$C NMR (75 MHz, CDCl$_3$) δ26.35, 26.75, 34.20 (br), 34.69, 34.77, 35.03 (br), 36.30, 36.62, 40.01 (br), 45.41 (br), 106.75, 112.25, 126.77, 128.49, 129.71, 135.74, 170.39. Anal. Calcd for C$_{22}$H$_{27}$NO$_4$: C, 71.52; H, 7.37; N, 3.79. Found: C, 71.63; H, 7.24; N, 3.95.

Adamantane-2-spiro-3'-8'-propyl-1',2',4'-trioxaspiro[4.5]decane (OZ25). A solution of O-methyl 2-adamantanone oxime (0.90 g, 5 mmol) and 4-propylcyclohexanone (1.40 g, 10 mmol) in pentane (100 ml) was treated with ozone according to the general procedure. The crude product was purified by flash chromatography (silica gel, 2% ether in petroleum ether) to afford trioxolane OZ25 (0.89 g, 58%) as a colorless solid. mp 49–51° C. (ethanol/H$_2$O 2:1); $^1$H NMR (300 MHz, CDCl$_3$) δ0.88 (t, J=7.2 Hz, 3H), 1.05–1.45 (m, 7H), 1.50–2.10 (m, 20H); $^{13}$C NMR (75 MHz, CDCl$_3$) δ14.31, 20.18, 26.49, 26.89, 30.12, 34.29, 34.78, 35.83, 36.39, 36.82, 38.52, 109.15, 111.07. Anal. Calcd for C$_{19}$H$_{30}$O$_3$: C, 74.47; H, 9.87. Found: C, 74.44; H, 10.02.

Adamantane-2-spiro-3'-7',9'-tetramethyl-1',2',4'-trioxaspiro[4.5]decane (OZ26). A solution of O-methyl 2-adamantanone oxime (0.90 g, 5 mmol) and 3,3,5,5-tetramethylcyclohexanone (1.54 g, 10 mmol) in pentane (100 ml) was treated with ozone according to the general procedure. The crude product was purified by flash chromatography (silica gel, 2% ether in petroleum ether) to afford trioxolane OZ26 (0.77 g, 48%) as a colorless solid. mp 71–72° C. (ethanol/H$_2$O 1:1); $^1$H NMR (300 MHz, CDCl$_3$) δ1.03 (s, 6H), 1.07 (s, 6H), 1.24 (s, 1H), 1.25 (s, 1H), 1.59 (s, 4H), 1.61–2.10 (m, 14H); $^{13}$C NMR 75 MHz, CDCl$_3$) δ26.50, 26.91, 31.47, 31.69, 32.36, 34.77, 34.92, 36.38, 36.83, 45.70, 51.46, 110.26, 110.96. Anal. Calcd for C$_{20}$H$_{32}$O$_3$: C, 74.96; H, 10.06. Found: C, 75.06; H, 9.96.

Adamantane-2-spiro-3'-8'-phenyl-1',2',4'-trioxaspiro[4.5] decane (OZ27). A solution of O-methyl 2-adamantanone oxime (0.90 g, 5 mmol) and 4-phenylcyclohexanone (1.74 g, 10 mmol) in pentane (80 ml) and $CH_2Cl_2$ (20 ml) was treated with ozone according to the general procedure. The crude product was purified by flash chromatography (silica gel, 5% ether in petroleum ether) to afford trioxolane OZ27 (0.83 g, 49%) as a colorless solid. mp 103–105° C. (ethanol/ $H_2O$ 2:1); $^1H$ NMR (300 MHz, $CDCl_3$) δ1.55–2.20 (m, 22H), 2.45–2.65 (m, 1H), 7.10–7.40 (m, 5H); $^{13}C$ NMR (75 MHz, $CDCl_3$) δ26.47, 26.87, 31.42, 34.58, 34.72, 34.79, 36.39, 36.79, 42.93, 108.39, 111.37, 126.14, 126.75, 128.37, 146.14. Anal. Calcd for $C_{22}H_{28}O_3$: C, 77.61; H, 8.29. Found: C, 77.81; H, 8.17.

Adamantane-2-spiro-3'-8'-t-butyloxyimino-1',2',4'-trioxaspiro[4.5]decane (OZ28). To a solution of OZ05 (0.557 g, 2.0 mmol) in $CH_2Cl_2$ (5 ml) and methanol (5 ml) were added pyridine (0.30 ml) and O-(tert-butyl) hydroxylamine hydrochloride (0.356 g, 3.0 mmol), and the reaction was stirred at room temperature for 24 h. The reaction mixture was concentrated in vacuo to provide a crude residue that was purified by recrystallizations from ethanol/$H_2O$ (20 ml, 1:1) and from ethanol/$H_2O$ (14 ml, 2.5:1) to give trioxolane OZ28 (0.63 g, 90%) as a colorless solid. mp 68–70° C. (ethanol/$H_2O$ 2.5:1); $^1H$ NMR (500 MHz, $CDCl_3$) δ1.26 (s, 9H), 1.60–2.10 (m, 18H), 2.32–2.45 (m, 2H), 2.50–2.60 (m, 1H), 2.65–2.76 (m, 1H); $^{13}C$ NMR (125.7 MHz, $CDCl_3$) δ21.54, 26.50, 26.91, 27.54, 28.97, 32.77, 34.13, 34.78, 34.80, 34.86, 34.91, 36.39, 36.80, 77.38, 108.31, 111.87, 155.29. Anal. Calcd for $C_{20}H_{31}NO_4$: C, 68.74; H, 8.94; N, 4.01. Found: C, 68.75; H, 8.74; N, 4.00.

Adamantane-2-spiro-3'-1',2',4'-trioxaspiro[4.5] decan-8'-one 2,4-dinitrophenylhydrazone (OZ29). A solution of OZ05 (0.28 g, 1.0 mmol) in ethanol (5 ml) and $CH_2Cl_2$ (1.5 ml) was added to a solution of 2,4-dinitrophenylhydrazine (0.30 g, 1.5 mmol), sulfuric acid (1.5 ml) and $H_2O$ (2.3 ml) in ethanol (7.5 ml), and the reaction was stirred at room temperature for 10 min before being quenched with ethanol (20 ml). The resulting precipitate was immediately filtered, washed with ethanol, and recrystallized from ethanol (20 ml) to afford trioxolane OZ29 (0.39 g, 85%) as a yellow solid. mp 142–144° C. dec (ethanol); 1H NMR (500 MHz, $CDCl_3$) δ1.60–2.20 (m, 18H), 2.45–2.85 (m, 4H), 7.94 (d, J=9.8 Hz, 1H), 8.27 (dd, J=9.8, 2.0 Hz, 1H), 9.0 (d, 2.9 Hz, 1H), 11.12 (s, 1H); $^{13}C$ NMR (125.7 MHz, $CDCl_3$) δ23.54, 26.44, 26.85, 31.89, 32.40, 33.59, 34.73, 34.80, 35.01, 36.34, 36.37, 36.70, 107.41, 112.50, 116.27, 123.45, 129.18, 129.98, 137.91, 145.22, 157.65. Anal. Calcd for $C_{22}H_{26}N_4O_7$: C, 57.63; H, 5.72; N, 12.22. Found: C, 57.74; H, 5.65; N, 12.02.

Adamantane-2-spiro-3'-1',2',4'-trioxaspiro[4.5]decan-8'-one 4-phenylsemicarbazone (OZ30). To a solution of OZ05 (0.28 g, 1.0 mmol) in ethanol (5 ml) and $CH_2Cl_2$ (1.5 ml) was added a solution of 4-phenylsemicarbazide (0.17 g, 1.1 mmol) in ethanol (5 ml) and $CH_2Cl_2$ (2 ml), and the reaction was stirred at room temperature for 1 h before being heated to 50° C. for 30 min. The solution was cooled to room temperature and the resulting precipitate was filtered, washed with ethanol, and dried to afford trioxolane OZ30 (0.37 g, 90%) as a colorless solid. mp 161–163° C. dec (ethanol); $^1H$ NMR (500 MHz, $CDCl_3$) δ1.62–2.10 (m, 18H), 2.48–2.61 (m, 3H), 2.62–2.69 (m, 1H), 7.02–7.09 (m, 1H), 7.23–7.35 (m, 2H), 7.48–7.54 (m, 2H), 8.24 (s, 1H), 9.11 (s, 1H); $^{13}C$ NMR (125.7 MHz, $CDCl_3$) δ23.17, 26.46, 26.87, 31.88, 32.57, 33.92, 34.75, 34.79, 34.93, 36.35, 36.37, 36.75, 107.75, 112.17, 119.33, 123.10, 128.84, 138.26, 150.83, 154.31. Anal. Calcd for $C_{23}H_{29}N_3O_4$: C, 67.13; H, 7.10; N, 10.21. Found: C, 66.86; H, 6.92; N, 10.04.

Adamantane-2-spiro-3'-11',12'-benzo-1',2',4', 9',14'-pentaoxadispiro[4.2.6.2]hexadecane (OZ31). To a solution of OZ05 (0.28 g, 1.0 mmol) in 1,2-dimethoxyethane (10 ml) were added 1,5-dihydro-3-methoxy-2,4-benzodioxepin (0.20 g, 1.1 mmol) and p-toluenesulfonic acid monohydrate (38 mg), and the reaction was stirred at room temperature for 30 min before being quenched by addition of saturated $NaHCO_3$ solution (1.0 ml). The reaction mixture was concentrated in vacuo to provide a crude residue that was purified by recrystallizations from ethanol/$H_2O$ (15 ml, 2:1) and from ethanol (10 ml) to give trioxolane OZ31 (0.22 g, 56%) as a colorless solid. mp 149–151° C. (ethanol); $^1H$ NMR (500 MHz, $CDCl_3$) δ1.60–2.20 (m, 22H), 4.80–4.94 (m, 4H), 7.02–7.09 (m, 2H), 7.13–7.22 (m, 2H); $^{13}C$ NMR (125.7 MHz, $CDCl_3$) δ26.53, 26.94, 29.46, 31.12, 34.81, 34.91, 36.42, 36.84, 64.65, 101.38, 108.42, 111.65, 126.09, 126.15, 126.75, 138.01, 138.09. Anal. Calcd for $C_{24}H_{30}O_5$: C, 72.34; H, 7.59. Found: C, 72.51; H, 7.70.

Adamantane-2-spiro-3'-8'-hydroxy-1',2',4'-trioxaspiro [4.5]decane (OZ32). A solution of $NaBH_4$ (42 mg, 1.1 mmol) in ethanol (10 ml) containing 3 drops of 1.0 M aq NaOH was added to a solution of OZ05 (0.277g, 1.0 mmol) in THF (5 ml) at 0° C. over a period of 5 min. The reaction was stirred at room temperature for 1 h before being quenched with EtOAc (10 ml). The solvent was removed using rotary evaporation and the crude product dissolved in EtOAc (50 ml) and washed with saturated aqueous bicarbonate (10 ml), water (10 ml), and brine (10 ml). The organic layer was dried over $MgSO_3$, filtered, and concentrated to give trioxolane OZ32 (0.25 g, 89%, 1:1 mixture of two diastereomers) as a colorless solid. mp 100–106° C.; $^1H$ NMR (500 MHz, $CDCl_3$) δ1.45–2.20 (m, 22H), 3.70–3.80 (m, 1H); $^{13}C$ NMR (125.7 MHz, $CDCl_3$) δ26.52, 26.94, 30.76, 31.26, 31.59, 32.07, 34.80, 34.88, 34.92, 36.38, 36.46, 36.83, 67.46, 68.06, 108.09, 108.19, 111.50, 111.68. Anal. Calcd for $C_{16}H_{24}O_4$: C, 68.54; H, 8.63. Found: C, 68.36; H, 8.44.

Adamantane-2-spiro-3'-8',8'-dimethyl-1',2',4'-trioxaspiro [4.5]decane (OZ33). A solution of O-methyl 2-adamantanone oxime (0.90 g, 5 mmol) and 4,4-dimethylcyclohexanone (1.26 g, 10 mmol) in pentane (100 ml) was treated with ozone according to the general procedure. The crude product was purified by flash chromatography (silica gel, 2% ether in petroleum ether) to afford trioxolane OZ33 (0.72 g, 49%) as a colorless solid. mp 125–127° C. (ethanol/H20 3:1); $^1H$ NMR (500 MHz, $CDCl_3$) δ0.92 (s, 3H), 0.95 (s, 3H), 1.42 (t, J=6.4 Hz, 4H), 1.62–2.10 (m, 18H); $^{13}C$ NMR (125.7 MHz, $CDCl_3$) δ26.46, 26.72 (br), 26.87, 28.87 (br), 29.41, 30.80, 34.75, 34.83, 36.37, 36.52, 36.79, 109.07, 111.19. Anal. Calcd for $C_{18}H_{28}O_3$: C, 73.93; H, 9.65. Found: C, 74.16; H, 9.55.

Adamantane-2-spiro-3'-8',8'-diphenyl-1',2',4'-trioxaspiro [4.5]decane (OZ34). A solution of O-methyl 2-adamantanone oxime (0.90 g, 5 mmol) and 4,4-diphenylcyclohexanone (1.25 g, 5 mmol) in pentane (60 ml) and $CH_2Cl_2$ (40 ml) was treated with ozone according to the general procedure. The crude product was purified by flash chromatography (silica gel, 5% ether in petroleum ether) to afford trioxolane OZ34 (0.48 g, 23%) as a colorless solid. mp 155–157° C. (ethanol); $^1H$ NMR (500 MHz, $CDCl_3$) δ1.40–2.20 (m, 18H), 2.32–2.65 (m, 4H), 7.00–7.42 (m, 1OH); $^{13}C$ NMR (125.7 MHz, $CDCl_3$) δ26.52, 26.91, 31.51, 34.05, 34.79, 34.87, 36.45, 36.83, 45.47, 108.66, 111.46, 125.79, 125.88, 126.72, 127.17, 128.30, 128.46, 145.94, 147.63. Anal. Calcd, for $C_{28}H_{32}O_3$: C, 80.73; H, 7.74. Found: C, 80.95; H, 7.61.

Adamantane-2-spiro-3'-8'-t-butoxycarbonyl-1',2',4'-trioxa-8'-azaspiro[4.5]decane (OZ35). A solution of O-methyl 2-adamantanone oxime (0.90 g, 5 mmol) and 1-tert-butoxycarbonyl-4-piperidone (1.99 g, 10 mmol) in pentane (80 ml) and $CH_2Cl_2$ (20 ml) was treated with ozone according to the general procedure. The crude product was purified by flash chromatography (silica gel, 15% ether in petroleum ether) to afford trioxolane OZ35 (0.73 g, 40%) as a colorless solid. mp 82–84° C. (ethanol/$H_2O$ 2:1); $^1$H NMR (500 MHz, $CDCl_3$) δ1.46 (s, 9H), 1.62–2.10 (m, 18H), 3.40–3.70 (m, 4H); $^{13}$C NMR (125.7 MHz, $CDCl_3$) δ26.48, 26.88, 28.41, 34.45, 34.76, 34.85, 36.43, 36.76, 41.60 (br), 79.73, 107.07, 112.01, 154.60. Anal. Calcd for $C_{20}H_{31}NO_5$: C, 65.73; H, 8.55; N, 3.83. Found: C, 65.52; H, 8.39; N, 3.80.

2,2,4,4,14,14-Hexamethyl-7,12,16,19,20-pentaoxatrispiro[5.1.2.5.2.2]icosane (OZ36). A solution of O-methyl 3,3,5,5-tetramethylcyclohexanone oxime (0.92 g, 5 mmol) and 3,3-dimethyl-1,5-dioxaspiro[5.5]undecan-9-one (1.98 g, 10 mmol) in pentane (100 ml) was treated with ozone according to the general procedure. The crude product was purified by flash chromatography (silica gel, 4% ether in petroleum ether) to afford trioxolane OZ36 (0.70 g, 38%) as a colorless solid. mp 95–97° C. (ethanol); $^1$H NMR (500 MHz, $CDCl_3$) δ0.97 (s, 6H), 1.03 (s, 6H), 1.04 (s, 6H), 1.20–1.29 (m, 2H), 1.55 (d, J=3.2 Hz, 2H), 1.63 (d, J=3.7 Hz, 2H), 1.83 (t, J=6.4 Hz, 4H), 1.86–2.04 (m, 4H), 3.50 (s, 4H); $^{13}$C NMR (125.7 MHz, $CDCl_3$) δ22.68, 29.47, 30.20, 30.40, 30.91, 32.21, 32.30, 45.59, 51.43, 70.29, 96.70, 107.94, 110.58. Anal. Calcd for $C_{21}H_{36}O_5$: C, 68.44; H, 9.85. Found: C, 68.24; H, 9.70.

Adamantane-2-spiro-3'-1',2',4'-trioxolane-5'-spiro-3"-7"-methoxyimino-cis-bicyclo[3.3.0]octane (OZ37). To a solution of OZ12 (0.304 g, 1.0 mmol) in $CH_2Cl_2$ (5 ml) and ethanol (5 ml) were added pyridine (0.15 ml) and methoxylamine hydrochloride (0.125 g, 1.5 mmol), and the reaction was stirred at room temperature for 24 h. The reaction mixture was concentrated in vacuo to provide a crude residue that was purified by recrystallization from ethanol/$H_2O$ (15 ml, 2:1) to give trioxolane OZ37 (0.32 g, 96%) as a colorless solid. mp 118–120° C. (ethanol/$H_2O$ 2:1); $^1$H NMR (500 MHz, $CDCl_3$) δ1.62–2.05 (m, 16H), 2.14–2.25 (m, 2H), 2.33–2.42 (m, 2H), 2.55–2.74 (m, 4H), 3.84 (s, 3H); $^{13}$C NMR (125.7 MHz, $CDCl_3$) δ26.49, 26.88, 33.23, 34.73, 34.85, 34.89, 35.99, 36.17, 36.79, 39.21, 39.33, 40.62, 41.42, 61.40, 111.54, 118.11, 165.40. Anal. Calcd for $C_{19}H_{27}NO_4$: C, 68.44; H, 8.16; N, 4.20. Found: C, 68.54; H, 7.96; N, 4.29.

Adamantane-2-spiro-3'-8'-(N-phthalimido)imino-1',2',4'-trioxaspiro[4.5]decane (OZ38). To a solution of OZ05 (0.454 g, 1.63 mmol) and N-aminophthalimide (0.290 g, 1.79 mmol) in $CH_2Cl_2$ (5 ml) and ethanol (5 ml) was added acetic acid (0.5 ml), and the reaction was heated to 50° C. for 2 h. The reaction mixture was cooled to room temperature, filtered through Celite, washed with $CH_2Cl_2$, and the solvent was removed in vacuo. The residue was purified by recrystallization from ethanol (10 ml) to give trioxolane OZ38 (0.45 g, 65%) as a colorless solid. mp 146–148° C. (ethanol); $^1$H NMR (500 MHz, $CDCl_3$) δ1.65–2.07 (m, 16H), 2.10–2.19 (m, 2H), 2.43–2.58 (m, 2H), 2.78–2.90 (m, 2H), 7.70–7.79 (m, 2H), 7.84–7.90 (m, 2H); $^{13}$C NMR (125.7 MHz, $CDCl_3$) δ26.43, 26.82, 28.12, 32.41, 33.15, 33.81, 34.72, 34.76, 34.79, 34.88, 36.30, 36.32, 36.70, 107.20, 112.28, 123.54, 131.08, 134.20, 164.32, 180.89. Anal. Calcd for $C_{24}H_{26}N_2O_5$: C, 68.23; H, 6.20; N, 6.63. Found: C, 68.12; H, 6.03; N, 6.57.

Adamantane-2-spiro-3'-1',2',4'-trioxaspiro[4.5]decan-8'-one tosylhydrazone (OZ39). To a solution of OZ05 (0.28 g, 1.0 mmol) and p-toluenesulfonhydrazide (0.21 g, 1.1 mmol) in $CH_2Cl_2$ (5 ml) and ethanol (5 ml) was added acetic acid (0.5 ml), and the reaction was heated to 50° C. for 2 h. The reaction mixture was cooled to room temperature and concentrated in vacuo. The residue was purified by recrystallization from ethanol/$H_2O$ (15 ml, 2:1) to give trioxolane OZ39 (0.26 g, 58%) as a colorless solid. mp 137° C. dec (ethanol/$H_2O$ 2:1); $^1$H NMR (500 MHz, DMSO-$d_6$) δ1.52–2.10 (m, 18H), 2.15–2.65 (m, 4H), 2.38 (s, 3H), 7.39 (d, J=7.8 Hz, 2H), 7.72 (d, J=7.8 Hz, 2H), 10.23 (s, 1H); $^{13}$C NMR (125.7 MHz, DMSO-$d_6$) δ20.92, 23.84, 25.72, 26.12, 31.05, 31.80, 33.09, 34.17, 34.29, 35.58, 35.97, 107.55, 111.19, 127.44, 129.31, 136.28, 143.01, 158.63. Anal. Calcd for $C_{23}H_{30}N_2O_5S$: C, 61.86; H, 6.77; N, 6.27. Found: C, 61.71; H, 6.81; N, 6.53.

Adamantane-2-spiro-3'-8'-isopropyl-1',2',4'-trioxaspiro[4.5]decane (OZ40). A solution of O-methyl 2-adamantanone oxime (0.90 g, 5 mmol) and 4-isopropylcyclohexanone (1.40 g, 10 mmol) in pentane (100 ml) was treated with ozone according to the general procedure. The crude product was purified by flash chromatography (silica gel, 2% ether in petroleum ether) to afford trioxolane OZ40 (0.47 g, 31%) as a colorless solid. mp 67–69° C. (ethanol); $^1$H NMR (500 MHz, $CDCl_3$) δ0.85 (d, J=6.8 Hz, 6H), 1.02–1.13 (m, 1H), 1.17–1.32 (m, 2H), 1.40–1.52 (m, 1H), 1.60–2.10 (m, 20H); $^{13}$C NMR (125.7 MHz, $CDCl_3$) δ19.82, 26.54, 26.85, 26.94, 32.12, 34.54, 34.81, 34.83, 36.44, 36.87, 42.57, 109.11, 111.10. Anal. Calcd for $C_{19}H_{30}O_3$: C, 74.47; H, 9.87. Found: C, 74.21; H, 9.86.

Adamantane-2-spiro-3'-8'-(4'-fluorophenyl)-1',2',4'-trioxaspiro[4.5]decane (OZ41). A solution of O-methyl 2-adamantanone oxime (0.36 g, 2 mmol) and 4-(4-fluorophenyl)cyclohexanone (0.38 g, 2 mmol) in pentane (50 ml) was treated with ozone according to the general procedure. The crude product was purified by flash chromatography (silica gel, 2% ether in petroleum ether) to afford trioxolane OZ41 (0.36 g, 50%) as a colorless solid. mp 103–106° C. (ethanol/$H_2O$ 1:1); $^1$H NMR NMR (500 MHz, $CDCl_3$) δ1.58–2.25 (m, 22H), 2.43–2.70 (m, 1H), 6.90–7.02 (m, 2H), 7.11–7.22 (m, 2H); $^{13}$C NMR (125.7 MHz, $CDCl_3$) δ26.43, 26.84, 31.57, 34.63, 34.76, 36.36, 36.75, 42.15, 108.24, 111.41, 115.06 (d, J=21.4 Hz), 128.03 (d, J=7.4 Hz), 141.75 (d, J=3.0 Hz), 161.26 (d, J=244.1 Hz). Anal. Calcd for $C_{22}H_{27}FO_3$: C, 73.72; H, 7.59. Found: C, 73.65; H, 7.66.

Adamantane-2-spiro-3'-5',5'-diphenyl-1',2',4'-trioxolane (OZ42). A solution of O-methyl 2-adamantanone oxime (0.90 g, 5 mmol) and benzophenone (0.91 g, 5 mmol) in pentane (90 ml) and $CH_2Cl_2$ (10 ml) was treated with ozone according to the general procedure. The crude product was purified by flash chromatography (silica gel, 2% ether in petroleum ether) to afford trioxolane OZ42 (0.55 g, 32%) as a colorless solid. mp 105–107° C. (ethanol/$H_2O$ 2:1); $^1$H NMR (500 MHz, $CDCl_3$) δ1.60–2.10 (m, 12H), 2.16–2.30 (m, 2H), 7.25–7.42 (m, 6H), 7.45–7.60 (m, 4H); $^{13}$C NMR (125.7 MHz, $CDCl_3$) δ26.56, 26.98, 34.86, 35.07, 36.21, 36.88, 109.68, 113.92, 126.97, 128.05, 128.56, 140.06. Anal. Calcd for $C_{23}H_{24}O_3$: C, 79.28; H, 6.94. Found: C, 79.32; H, 6.96.

Adamantane-2-spiro-3'-5', 5'-bis(4'-chlorophenyl)-1',2',4'-trioxolane (OZ43). A solution of O-methyl 2-adamantanone oxime (0.90 g, 5 mmol) and 4,4'-dichlorobenzophenone (1.26 g, 5 mmol) in pentane (80 ml) and $CH_2Cl_2$ (20 ml) was treated with ozone according to the general procedure. The crude product was purified by flash chromatography (silica gel, 1% ether in petroleum ether) to afford trioxolane OZ43 (0.55 g, 26%) as a colorless solid.

mp 128–130° C. (ethanol/H20 5:2); $^1$H NMR (500 MHz, CDCl$_3$) δ1.60–2.05 (m, 12H), 2.10–2.30 (m, 2H), 7.20–7.60 (m, 8H); $^{13}$C NMR (125.7 MHz, CDCl$_3$) δ26.46, 26.88, 34.80, 35.00, 36.17, 36.74, 108.78, 114.42, 128.33, 128.43, 134.93, 138.20. Anal. Calcd for C$_{23}$H$_{22}$Cl$_2$O$_3$: C, 66.19; H, 5.31. Found: C, 66.37; H, 5.12.

Adamantane-2-spiro-3'-5', 5'-bis(4'-fluorophenyl)-1',2',4'-trioxolane (OZ44). A solution of O-methyl 2-adamantanone oxime (0.90 g, 5 mmol) and 4,4'-difluorobenzophenone (1.09 g, 5 mmol) in pentane (90 ml) and CH$_2$Cl$_2$ (10 ml) was treated with ozone according to the general procedure. The crude product was purified by flash chromatography (silica gel, 2% ether in petroleum ether) to afford trioxolane OZ44 (0.87 g, 45%) as a colorless solid. mp 86–89° C. (ethanol/H$_2$O 1:1); $^1$H NMR (500 MHz, CDCl$_3$) δ1.60–2.05 (m, 12H), 2.06–2.40 (m, 2H), 6.90–7.20 (m, 4H), 7.35–7.65 (m, 4H); $^{13}$C NMR 125.7 MHz, CDCl$_3$) δ26.41, 26.84, 34.77, 34.96, 36.17, 36.71, 108.95, 114.21, 115.06 (d, J=21.3 Hz), 128.96 (d, J=8.4 Hz), 135.56, 162.95 (d, J=248.0 Hz). Anal. Calcd for C$_{23}$H$_{22}$F$_2$O$_3$: C, 71.86; H, 5.77. Found: C, 71.78; H, 5.87.

Adamantane-2-spiro-3'-5',5'-bis(2',3',4',5',6'-pentafluorophenyl)-5',2',4'-trioxolane (OZ45). A solution of O-methyl 2-adamantanone oxime (0.90 g, 5 mmol) and decafluorobenzophenone (1.81 g, 5 mmol) in pentane (90 ml) and CH$_2$Cl$_2$ (10 ml) was treated with ozone according to the general procedure. The crude product was purified by flash chromatography (silica gel, 1% ether in petroleum ether) to afford trioxolane OZ45 (0.60 g, 23%) as a colorless solid. mp 92–95° C. (ethanol); $^1$H NMR (500 MHz, CDCl$_3$) δ1.62–2.03 (m, 12H), 2.06–2.20 (m, 2H); $^{13}$C NMR (125.7 MHz, CDCl$_3$) δ26.37, 26.70, 34.78, 34.83, 35.91, 36.50, 103.85 (m), 113.07 (m), 115.63, 136.83 (m), 138.84 (m), 140.95 (m), 143.00 (m), 143.54 (m), 145.54 (m). Anal. Calcd for C$_{23}$H$_{14}$F$_{10}$O$_3$: C, 52.29; H, 2.67. Found: C, 52.31; H, 2.77.

Adamantane-2-spiro-3'-5',5'-bis[3'-(trifluoromethyl)phenyl]-1',2',4'-trioxolane (OZ46). A solution of O-methyl 2-adamantanone oxime (0.90 g, 5 mmol) and 3,3'-bis(trifluoromethyl)benzophenone (1.59 g, 5 mmol) in pentane (80 ml) and CH$_2$Cl$_2$ (20 ml) was treated with ozone according to the general procedure. The crude product was purified by flash chromatography (silica gel, 1% ether in petroleum ether) to afford trioxolane OZ46 (0.62 g, 26%) as a colorless solid. mp 60–62° C. (ethanol/H$_2$O 1:1); $^1$H NMR (500 MHz, CDCl$_3$) δ51.60–2.05 (m, 12H), 2.10–2.30 (m, 2H), 7.40–7.57 (m, 2H), 7.59–7.75 (m, 4H), 7.82 (s, 2H); $^{13}$C NMR (125.7 MHz, CDCl$_3$) δ26.46, 26.85, 34.82, 34.94, 36.13, 36.71, 108.36, 114.99, 123.53 (q, J=3.8 Hz), 123.93 (q, J=272.4 Hz), 125.84 (q, J=3.8 Hz), 128.93, 130.17, 130.98 (q, J=32.8 Hz), 140.60. Anal. Calcd for C$_{25}$H$_{22}$F$_6$O$_3$: C, 61.98; H, 4.58. Found: C, 61.70; H, 4.71.

Adamantane-2-spiro-3'-8'-(4'-chlorophenyl)-1',2',4'-trioxaspiro[4.5]decane (OZ47). A solution of O-methyl 2-adamantanone oxime (0.90 g, 5 mmol) and 4-(4-chlorophenyl)cyclohexanone (1.05 g, 5 mmol) in pentane (80 ml) and CH$_2$Cl$_2$ (20 ml) was treated with ozone according to the general procedure. The crude product was purified by flash chromatography (silica gel, 4% ether in petroleum ether) to afford trioxolane OZ47 (0.68 g, 36%) as a colorless solid. mp 122–124° C. (ethanol); $^1$H NMR (500 MHz, CDCl$_3$) δ1.60–2.18 (m, 22H), 2.40–2.60 (m, 1H), 7.05–7.30 (m, 4H); $^{13}$C NMR (125.7 MHz, CDCl$_3$) δ26.59, 26.99, 31.43, 34.68, 34.86, 36.53, 36.89, 42.40, 108.22, 111.48, 128.12, 128.52, 131.84, 144.63. Anal. Calcd for C$_{22}$H$_{27}$C$_{10}$O$_3$: C, 70.48; H, 7.26. Found: C, 70.50; H, 7.38.

Adamantane-2-spiro-3'-8'-[4'-(trifluoromethyl)phenyl]-1',2',4'-trioxaspiro[4.5]decane (OZ48). A solution of O-methyl 2-adamantanone oxime (0.90 g, 5 mmol) and 4-[4-(trifluoromethyl)phenyl]cyclohexanone (1.21 g, 5 mmol) in pentane (90 ml) and CH$_2$Cl$_2$ (10 ml) was treated with ozone according to the general procedure. The crude product was purified by flash chromatography (silica gel, 4% ether in petroleum ether) to afford trioxolane OZ48 (0.96 g, 47%) as a colorless solid. mp 115–117° C. (ethanol/H$_2$O 2:1); 1H NMR (500 MHz, CDCl$_3$) δ1.60–2.20 (m, 22H), 2.50–2.70 (m, 1H), 7.26–7.65 (m, 4H); $^{13}$C NMR (125.7 MHz, CDCl$_3$) δ26.60, 27.01, 31.26, 34.64, 34.88, 36.56, 36.90, 42.91, 108.13, 111.57, 124.33 (q, J=269.3 Hz), 125.38 (q, J=3.8 Hz), 127.14, 128.67 (q, J=32.8 Hz), 150.21. Anal. Calcd for C$_{23}$H$_{27}$F$_3$O$_3$: C, 67.63; H, 6.66. Found: C, 67.41; H, 6.48.

Adamantane-2-spiro-3'-8'-acetyl-1',2',4'-trioxa-8'-azaspiro[4.5]decane (OZ49). A solution of O-methyl 2-adamantanone oxime (0.90 g, 5 mmol) and 1-acetyl-4-piperidone (0.71 g, 5 mmol) in pentane (60 ml) and CH$_2$Cl$_2$ (40 ml) was treated with ozone according to the general procedure. The crude product was purified by flash chromatography (silica gel, ether) to afford trioxolane OZ49 (0.22 g, 14%) as a colorless solid. mp 77–79° C. (ethanol/H$_2$O 1:2); $^1$H NMR (500 MHz, CDCl$_3$) δ1.60–2.05 (m, 18H), 2.11 (s, 3H), 3.45–3.70 (m, 3H), 3.72–3.86 (m, 1H); $^{13}$C NMR (125.7 MHz, CDCl$_3$) δ21.22, 26.51, 26.91, 34.14, 34.74, 34.83, 35.00, 35.16, 36.44, 36.51, 36.76, 39.42, 44.15, 106.75, 112.26, 168.77. Anal. Calcd for C$_{17}$H$_{25}$NO$_4$: C, 66.43; H, 8.20; N, 4.56. Found: C, 66.18; H, 7.96; N, 4.47.

Adamantane-2-spiro-3'-1',2',4'-trioxa-8'-thiaspiro[4.5]decane 8',8'-dioxide (OZ50). A solution of O-methyl 2-adamantanone oxime (0.90 g, 5 mmol) and 1,1-dioxotetrahydrothiopyran-4-one (0.74 g, 5 mmol) in pentane (25 ml) and CH$_2$Cl$_2$ (50 ml) was treated with ozone according to the general procedure. The crude product was purified by flash chromatography (silica gel, 50% ether in hexanes) to afford trioxolane OZ50 (0.23 g, 15%) as a colorless solid. mp 128–129° C. (ethanol/H$_2$O 1:1); $^1$H NMR (500 MHz, CDCl$_3$) δ1.60–2.05 (m, 14H), 2.38 (t, J=6.3 Hz, 4H), 3.10–3.30 (m, 4H); $^{13}$C NMR (125.7 MHz, CDCl$_3$) δ26.36, 26.76, 32.31, 34.74, 34.84, 36.31, 36.59, 48.81, 104.97, 113.33. Anal. Calcd for C$_{15}$H$_{22}$O$_5$S: C, 57.30; H, 7.05. Found: C, 57.44; H, 6.97.

Adamantane-2-spiro-3'-8'-(p-toluenesulfonyl)-1',2',4'-trioxa-8'-azaspiro[4.5]decane (OZ51). A solution of O-methyl 2-adamantanone oxime (0.90 g, 5 mmol) and 1-(p-toluenesulfonyl)-4-piperidone (1.30 g, 5 mmol) in pentane (45 ml) and CH$_2$Cl$_2$ (25 ml) was treated with ozone according to the general procedure. The crude product was purified by flash chromatography (silica gel, 25% ether in hexanes) to afford trioxolane OZ51 (0.33 g, 16%) as a colorless solid. mp 124–125° C. (ethanol); $^1$H NMR (500 MHz, CDCl$_3$) δ1.60–2.05 (m, 18H), 2.44 (s, 3H), 2.85–3.02 (m, 2H), 3.27–3.42 (m, 2H), 7.32 (d, J=8.3 Hz, 2H), 7.64 (d, J=8.3 Hz, 2H); $^{13}$C NMR (125.7 MHz, CDCl$_3$) δ21.47, 26.48, 26.87, 34.06, 34.76, 34.79, 36.42, 36.73, 44.26, 106.00, 112.34, 127.62, 129.71, 133.94, 143.60. Anal. Calcd for C$_{22}$H$_{29}$NO$_5$S: C, 62.98; H, 6.97; N, 3.34. Found: C, 62.99; H, 6.88; N, 3.12.

Adamantane-2-spiro-3'-5',5'-dibenzyl-1',2',4'-trioxolane (OZ52). A solution of O-methyl 2-adamantanone oxime (0.90 g, 5 mmol) and 1,3-diphenylacetone (1.10 g, 5 mmol) in pentane (60 ml) was treated with ozone according to the general procedure. The crude product was purified by flash chromatography (silica gel, 1% ether in hexanes) to afford trioxolane OZ52 (1.10 g, 58%) as a colorless solid. mp 86–88° C. (ethanol/H$_2$O 1:1); $^1$H NMR (500 MHz, CDCl$_3$)

δ1.40–2.10 (m, 14H), 2.93 (d, J=4.2 Hz, 2H), 3.04 (d, J=4.2 Hz 2H), 7.10–7.40 (m, 10H); $^{13}$C NMR (125.7 MHz, CDCl$_3$) δ26.49, 26.93, 34.81, 34.90, 36.13, 36.80, 41.92, 110.37, 112.48, 126.58, 127.89, 130.89, 135.70. Anal. Calcd for C$_{25}$H$_{28}$O$_3$: C, 79.75; H, 7.50. Found: C, 79.57; H, 7.39.

Adamantane-2-spiro-3'-8'-[3'-(ethoxycarbonyl) propionyl]-1',2',4'-trioxa-8'-azaspiro[4.5]decane (OZ53). A solution of O-methyl 2-adamantanone oxime (0.90 g, 5 mmol) and 1-[3-(ethoxycarbonyl)propionyl]-4-piperidone (1.20 g, 5 mmol) in pentane (45 ml) and CH$_2$Cl$_2$ (15 ml) was treated with ozone according to the general procedure. The crude product was purified by flash chromatography (silica gel, 25% ether in hexanes) to afford trioxolane OZ53 (0.60 g, 30%) as a colorless solid. mp 116–117° C. (ethanol/H$_2$O 1:1); $^1$H NMR (500 MHz, CDCl$_3$) δ1.26 (t, J=7.1 Hz, 3H), 1.60–2.10 (m, 18H), 2.55–2.75 (m, 4H), 3.45–3.70 (m, 3H), 3.72–3.87 (m, 1H), 4.15 (q, J=7.2 Hz, 2H); $^{13}$C NMR (125.7 MHz, CDCl$_3$) δ14.17, 26.50, 26.90, 27.84, 29.45, 34.17, 34.74, 34.98, 35.06, 36.48, 36.76, 39.81, 43.10, 60.51, 106.80, 112.26, 169.60, 173.02. Anal. Calcd for C$_{21}$H$_{31}$NO$_6$: C, 64.10; H, 7.94; N, 3.56. Found: C, 63.96; H, 7.81; N, 3.40.

Adamantane-2-spiro-3'-8'-carboxymethoxyimino-1',2',4'-trioxaspiro[4.5]decane (OZ54). To a solution of OZ05 (0.278 g, 1.0 mmol) in methanol (5 ml) were added pyridine (0.16 g, 2.0 mmol) and carboxymethoxylamine hemihydrochloride (0.262 g, 1.2 mmol). The reaction was stirred at room temperature for 4 h. After the solvent was removed in vacuo, the crude residue was acidified with 2 M HCl (25 ml) and extracted with CH$_2$Cl$_2$ (3×20 ml). The combined extracts were dried over Na$_2$SO$_4$ and concentrated to give a residue that was triturated in hexanes to afford trioxolane OZ54 (0.30 g, 85%) as a colorless solid. mp 126–128° C. (hexanes); $^1$H NMR (500 MHz, CDCl$_3$) δ1.60–2.10 (m, 18H), 2.33–2.50 (m, 2H), 2.59–2.70 (m, 1H), 2.72–2.90 (m, 1H), 4.62 (s, 2H); $^{13}$C NMR (125.7 MHz, CDCl$_3$) δ22.08, 26.52, 26.92, 28.55, 32.54, 33.76, 34.80, 34.87, 34.92, 36.41, 36.79, 69.71, 107.77, 112.15, 160.04, 174.84. Anal. Calcd for C$_{18}$H$_{25}$NO$_6$: C, 61.52; H, 7.17; N, 3.99. Found: C, 61.48; H, 7.16; N, 3.84.

Adamantane-2-spiro-3'-1',2',4'-trioxaspiro[4.5]decan-8'-one pyridinioacetylhydrazone chloride (OZ55). To a solution of OZ05 (278 mg, 1 mmol) in ethanol (10 ml) and acetic acid (1 ml) was added Girard's reagent P (190 mg, 1 mmol). The mixture was stirred at 25° C. for 24 h. The solvent was removed in vacuo, and the residue was purified by recrystallization from ether/methanol (95:5) to afford trioxolane OZ55 (140 mg, 31%, 2:1 mixture of two tautomers) as a yellowish solid. mp 88–90° C. (ether/methanol 9:1); $^1$H NMR (500 MHz, CD$_3$OD) δ1.58–2.39 (m, 18H), 2.43–2.92 (m, 4H), 5.72 (s, minor isomer), 5.94 (s, major isomer), 8.10–8.28 (m, 2H), 8.61–8.78 (m, 1H), 8.90–9.14 (m, 2H); $^{13}$C NMR (125.7 MHz, CD$_3$OD) δ21.36, 24.51, 25.72, 27.88, 28.29, 29.00, 29.08, 31.93, 32.59, 32.80, 32.87, 33.58, 33.68, 33.89, 34.83, 35.73, 35.77, 35.92, 36.63, 37.22, 37.72, 38.78, 39.02, 40.18, 40.25, 41.08, 61.72 (m), 62.77 (m), 108.80, 108.92, 113.21, 128.86, 129.00, 129.20, 147.46, 147.66, 157.71, 163.30, 167.86, 175.75. Anal. Calcd for C$_{23}$H$_{30}$ClN$_3$O$_4$·H$_2$O: C, 59.28; H, 6.92; N, 9.02. Found: C, 58.88; H, 7.24; N, 8.83.

Adamantane-2-spiro-3'-8'-methanesulfonyl-1',2',4'-trioxa-8'-azaspiro[4.5]decane (OZ56). A solution of O-methyl 2-adamantanone oxime (0.90 g, 5 mmol) and 1-methanesulfonyl-4-piperidone (0.90 g, 5.1 mmol) in pentane (50 ml) and CH$_2$Cl$_2$ (50 ml) was treated with ozone according to the general procedure. The crude product was purified by flash chromatography (silica gel, 20% ether in hexanes) to afford trioxolane OZ56 (0.33 g, 19%) as a colorless solid. mp 146–148° C. (95% ethanol); $^1$H NMR (500 MHz, CDCl$_3$) δ1.62–2.08 (m, 18H), 2.81 (s, 3H), 3.26–3.34 (m, 2H), 3.38–3.47 (m, 2H); $^{13}$C NMR (125.7 MHz, CDCl$_3$) δ26.50, 26.90, 34.28, 34.79, 34.87, 35.56, 36.47, 36.75, 44.07, 106.02, 112.48. Anal. Calcd for C$_{16}$H$_{25}$NO$_5$S: C, 55.95; H, 7.34; N, 4.08. Found: C, 56.06; H, 7.33; N, 3.91.

Adamantane-2-spiro-3'-8'-(4'-chlorobenzenesulfonyl)-1',2',4'-trioxa-8'-azaspiro[4.5]decane (OZ57). A solution of O-methyl 2-adamantanone oxime (0.90 g, 5 mmol) and 1-(4-chlorobenzenesulfonyl)-4-piperidone (1.37 g, 5 mmol) in pentane (25 ml) and CH$_2$Cl$_2$ (75 ml) was treated with ozone according to the general procedure. The crude product was purified by flash chromatography (silica gel, 25% ether in hexanes) to afford trioxolane OZ57 (0.19 g, 9%) as a colorless solid. mp 142–144° C. (95% ethanol); $^1$H NMR (500 MHz, CDCl$_3$) δ1.60–2.09 (m, 18H), 2.96–3.05 (m, 2H), 3.27–3.36 (m, 2H), 7.52 (d, J=8.8 Hz, 2H), 7.70 (d, J=8.8 Hz, 2H); $^{13}$C NMR (125.7 MHz, CDCl$_3$) δ26.45, 26.83, 34.05, 34.74, 34.78, 36.40, 36.70, 44.26, 105.79, 112.46, 128.93, 129.46, 135.55, 139.45. Anal. Calcd for C$_{21}$H$_{26}$ClNO$_5$S: C, 57.33; H, 5.96; N, 3.18. Found: C, 57.59; H, 6.00; N, 3.08.

Adamantane-2-spiro-3'-8'-(3'-carboxypropionyl)-1',2',4'-trioxa-8'-azaspiro[4.5]decane (OZ58). To a suspension of OZ53 (500 mg, 1.27 mmol) in ethanol (5 ml) was added KOH (225 mg, 4 mmol) dissolved in water (5 ml). The mixture was heated at 50° C. for 4 h. Ethanol was removed in vacuo and the residue was washed with CH$_2$Cl$_2$ (2×10 ml). The aqueous layer was acidified to pH 2 with 3 M aq. HCl and extracted with CH$_2$Cl$_2$ (2×10 ml). The combined organic extracts were dried over MgSO$_4$ and concentrated in vacuo. The residue was purified by recrystallization from ethanol to afford trioxolane OZ58 (200 mg, 43%) as a colorless solid. mp 124–126° C. (95% ethanol); $^1$H NMR (500 MHz, CDCl$_3$) δ1.60–2.10 (m, 18H), 2.60–2.80 (m, 4H), 3.50–3.70 (m, 3H), 3.72–3.89 (m, 1H); $^{13}$C NMR (125.7 MHz, CDCl$_3$) δ26.51, 26.90, 27.95, 29.57, 34.13, 34.75, 34.83, 35.00, 36.45, 36.50, 36.76, 40.04, 43.27, 106.62, 112.37, 170.20, 176.15. Anal. Calcd for C$_{19}$H$_{27}$NO$_6$: C, 62.45; H, 7.45; N, 3.83. Found: C, 62.60; H, 7.53; N, 3.70.

Adamantane-2-spiro-3'-8'-(4'-methoxybenzenesulfonyl)-1',2',4'-trioxa-8'-azaspiro[4.5]decane (OZ59). A solution of O-methyl 2-adamantanone oxime (0.90 g, 5 mmol) and 1-(4-methoxybenzenesulfonyl)-4-piperidone (1.35 g, 5 mmol) in pentane (50 ml) and CH$_2$Cl$_2$ (50 ml) was treated with ozone according to the general procedure. The crude product was purified by flash chromatography (silica gel, 20% ether in hexanes) to afford trioxolane OZ59 (0.40 g, 18%) as a colorless solid. mp 116–118° C.; $^1$H NMR (500 MHz, CDCl$_3$) δ1.60–2.05 (m, 18H), 2.89–3.01 (m, 2H), 3.28–3.41 (m, 2H), 3.88 (s, 3H), 6.99 (d, J=9.3 Hz, 2H), 7.69 (d, J=8.8 Hz, 2H); $^{13}$C NMR (125.7 MHz, CDCl$_3$) δ26.46, 26.85, 34.02, 34.74, 34.78, 36.40, 36.71, 44.27, 55.60, 105.99, 112.32, 114.32, 128.45, 129.68, 163.13. Anal. Calcd for C$_{22}$H$_{29}$NO$_6$S: C, 60.67; H, 6.71; N, 3.22. Found: C, 60.81; H, 6.79; N, 3.10.

Adamantane-2-spiro-3'-8'-benzenesulfonyl-1', 2',4'-trioxa-8'-azaspiro[4.5]decane (OZ60). A solution of O-methyl 2-adamantanone oxime (0.90 g, 5 mmol) and 1-benzenesulfonyl-4-piperidone (1.20 g, 5 mmol) in pentane (40 ml) and CH$_2$Cl$_2$ (60 ml) was treated with ozone according to the general procedure. The crude product was purified by flash chromatography (silica gel, 20% ether in hexanes) to afford trioxolane OZ60 (0.20 g, 10%) as a colorless solid.

mp 130–132° C. (95% ethanol); $^1$H NMR (500 MHz, CDCl$_3$) δ1.60–2.09 (m, 18H), 2.92–3.05 (m, 2H), 3.29–3.42 (m, 2H), 7.50–7.57 (m, 2H), 7.58–7.64 (m, 1H), 7.73–7.81 (m, 2H); $^{13}$C NMR (125.7 MHz, CDCl$_3$) δ26.46, 26.85, 34.07, 34.75, 34.79, 36.41, 36.72, 44.28, 105.95, 112.38, 127.55, 129.10, 132.79, 136.96. Anal. Calcd for C$_{21}$H$_{27}$NO$_5$S: C, 62.20; H, 6.71; N, 3.45. Found: C, 62.38; H, 6.88; N, 3.44.

Adamantane-2-spiro-3'-8'-ethoxycarbonylmethyl-1',2',4'-trioxaspiro[4.5]decane (OZ61). A solution of O-methyl 2-adamantanone oxime (0.90 g, 5 mmol) and 4-(ethoxycarbonylmethyl)cyclohexanone (1.00 g, 5.4 mmol) in pentane (80 ml) and CH$_2$Cl$_2$ (20 ml) was treated with ozone according to the general procedure. The crude product was purified by flash chromatography (silica gel, 2% ether in hexanes) to afford trioxolane OZ61 (0.35 g, 20%) as a colorless solid. mp 62–64° C. (95% ethanol); $^1$H NMR (500 MHz, CDCl$_3$) δ1.25 (t, J=7.1 Hz, 3H), 1.20–1.32 (m, 2H), 1.60–2.10 (m, 21H), 2.20 (d, J=6.8 Hz, 2H), 4.12 (q, J=7.1 Hz, 2H); $^{13}$C NMR (125.7 MHz, CDCl$_3$) δ14.23, 26.59, 26.99, 29.94, 33.24, 33.99, 34.84, 34.86, 36.50, 36.90, 40.92, 60.16, 108.48, 111.31, 172.67. Anal. Calcd for C$_{20}$H$_{30}$O$_5$: C, 68.54; H, 8.63. Found: C, 68.63; H, 8.62.

3,11-Diphenyl-7,14,15-trioxadispiro[5.1.5.2]pentadecane (OZ62). A solution of O-methyl 4-phenylcyclohexanone oxime (1.02 g, 5 mmol) and 4-phenylcyclohexanone (0.87 g, 5 mmol) in pentane (90 ml) and CH$_2$Cl$_2$ (10 ml) was treated with ozone according to the general procedure. The crude product was purified by flash chromatography (silica gel, 2% ether in hexanes) to afford trioxolane OZ62 (0.45 g, 25%, 1:1 mixture of two diastereomers) as a colorless solid. mp 136–138° C. (95% ethanol); $^1$H NMR (500 MHz, CDCl$_3$) δ1.65–2.20 (m, 16H), 2.52–2.62 (m, 2H), 7.16–7.35 (m, 10H); $^{13}$C NMR (125.7 MHz, CDCl$_3$) δ31.14, 31.46, 34.53, 34.64, 42.99, 43.27, 108.43, 108.86, 126.19, 126.79, 126.86, 128.39, 128.41, 146.08, 146.11. Anal. Calcd for C$_{24}$H$_{28}$O$_3$: C, 79.09; H, 7.74. Found: C, 79.22; H, 7.68.

Adamantane-2-spiro-3'-8'-cyano-8'-phenyl-1',2',4'-trioxaspiro[4.5]decane (OZ63). A solution of O-methyl 2-adamantanone oxime (1.79 g, 10 mmol) and 4-cyano-4-phenylcyclohexanone (2.00 g, 10 mmol) in pentane (60 ml) and CH$_2$Cl$_2$ (20 ml) was treated with ozone according to the general procedure. The crude product was purified by flash chromatography (silica gel, 4% ether in petroleum ether) to afford trioxolane OZ63 (1.85 g, 51%) as a colorless solid. mp 137–138° C. (ethanol/H$_2$O 1:1); $^1$H NMR NMR (500 MHz, CDCl$_3$) δ1.60–2.38 (m, 22H), 7.25–7.55 (m, 5H); $^{13}$C NMR (125.7 MHz, CDCl$_3$) δ26.55, 26.92, 31.92, 34.84, 34.89, 36.53, 36.81, 43.21, 106.90, 112.14, 121.71, 125.53, 128.13, 129.02, 139.88. Anal. Calcd for C$_{23}$H$_{27}$NO$_3$: C, 75.59; H, 7.45; N, 3.83. Found: C, 75.46; H, 7.39; N, 3.86.

Adamantane-2-spiro-3'-8'-neopentyloxycarbonyl-1',2',4'-trioxaspiro[4.5]decane (OZ64). A solution of O-methyl 2-adamantanone oxime (0.54 g, 3 mmol) and 4-(neopentyloxycarbonyl)cyclohexanone (0.64 g, 3 mmol) in pentane (100 ml) was treated with ozone according to the general procedure. The crude product was purified by flash chromatography (silica gel, 4% ether in petroleum ether) to afford trioxolane OZ64 (0.70 g, 62%, 4:1 mixture of two diastereomers). Recrystallization from 95% ethanol gave the analytically pure trans-isomer (0.20 g, 18%) as a colorless solid. mp 84–86° C. (95% ethanol); $^1$H NMR (500 MHz, CDCl$_3$) δ0.93 (s, 9H), 1.60–2.10 (m, 22H), 2.32–2.44 (m, 1H), 3.76 (s, 2H); $^{13}$C NMR (125.7 MHz, CDCl$_3$) δ26.32, 26.45, 26.57, 26.98, 31.41, 33.42, 34.83, 34.88, 36.50, 36.87, 41.69, 73.70, 107.98, 111.54, 174.76. Anal. Calcd for C$_{22}$H$_{34}$O$_5$: C, 69.81; H, 9.05. Found: C, 70.00; H, 8.98.

Adamantane-2-spiro-3'-1',2',4'-trioxaspiro[4.5]decane-8'-yl sodium sulfate (OZ65). A mixture of OZ32 (0.42 g, 1.5 mmol), sulfur trioxide pyridine complex (0.60 g, 3.8 mmol), pyridine (0.75 ml), and acetic anhydride (0.75 ml) was heated at 50° C. with stirring for 30 min. The reaction mixture was cooled to room temperature, diluted with petroleum ether (30 ml), and kept at −20° C. overnight. The precipitate was collected by filtration, washed with petroleum ether/benzene (5:1), and dried in a vacuum oven. The dried solid residue was dissolved in chloroform (12 ml), cooled in an ice bath, and filtered to remove the insoluble sulfur trioxide pyridine complex. The filtrate was concentrated to afford the pyridinium sulfate of OZ32 (0.65 g, 100%). To a suspension of the above pyridinium salt (0.50 g) in water (6 ml) was added 10% aqueous sodium carbonate (6 ml) while shaking. The mixture was kept at −20° C. for 4 h. The precipitate was filtered, washed with cold water (2 ml), and dried in a vacuum oven to give trioxolane OZ65 (0.35 g, 61%, 2:1 mixture of two diastereomers) as a colorless solid. mp 154° C. dec (water); $^1$H NMR (500 MHz, DMSO-d$_6$) δ1.50–2.02 (m, 22H), 4.12–4.22 (m, 1H); $^{13}$C NMR (125.7 MHz, CDCl$_3$) δ25.88, 26.28, 28.84, 29.24, 30.26, 30.68, 34.30, 34.36, 35.78, 35.89, 36.17, 70.66, 71.08, 108.05, 108.09, 110.68, 110.72. Anal. Calcd for C$_{16}$H$_{23}$NaO$_7$S.H$_2$O: C, 47.99; H, 6.29. Found: C, 47.67; H, 6.59.

3,3-Bis(4-fluorophenyl)-8-phenyl-1,2,4-trioxaspiro[4.5]decane (OZ66). A solution of O-methyl 4-phenylcyclohexanone oxime (1.02 g, 5 mmol) and 4,4'-difluorobenzophenone (1.09 g, 5 mmol) in pentane (90 ml) and CH$_2$Cl$_2$ (10 ml) was treated with ozone according to the general procedure. The crude product was purified by flash chromatography (silica gel, 3% ether in petroleum ether) to afford trioxolane OZ66 (0.56 g, 27%, 3:1 mixture of two diastereomers) as a colorless solid. mp 87–90° C. (ethanol/H$_2$O 2.5:1); $^1$H NMR (500 MHz, CDCl$_3$) δ1.60–2.15 (m, 8H), 2.51–2.70 (m, 1H), 6.99–7.09 (m, 4H), 7.16–7.36 (m, 5H), 7.44–7.53 (m, 4H); $^{13}$C NMR (125.7 MHz, CDCl$_3$) δ31.23, 31.34, 34.20, 34.48, 42.85, 43.01, 108.84, 109.29, 111.20, 111.29, 115.15 (d, J=21.4 Hz), 115.18 (d, J=21.4 Hz), 126.29, 126.33, 126.74, 126.83, 128.47, 128.95 (d, J=8.4 Hz), 129.01 (d, J=6.1 Hz), 135.33, 135.36, 145.74, 145.79, 163.05 (d, J=248.0 Hz). Anal. Calcd for C$_{25}$H$_{22}$F$_2$O$_3$: C, 73.52; H, 5.43. Found: C, 73.53; H, 5.51.

Bicyclo[3.3.1]nonane-9-spiro-3'-8'-phenyl-1',2',4'-trioxaspiro[4.5]decane (OZ67). A solution of O-methyl bicyclo[3.3.1]nonan-9-one oxime (0.84 g, 5 mmol) and 4-phenylcyclohexanone (0.87 g, 5 mmol) in pentane (80 ml) and CH$_2$Cl$_2$ (20 ml) was treated with ozone according to the general procedure. The crude product was purified by flash chromatography (silica gel, 3% ether in petroleum ether) to afford trioxolane OZ67 (0.54 g, 33%) as a colorless solid. mp 120–122° C. (ethanol/H$_2$O 4:1); $^1$H NMR (500 MHz, CDCl$_3$) δ1.41–1.60 (m, 2H), 1.61–2.20 (m, 20H), 2.49–2.60 (m, 1H), 7.14–7.35 (m, 5H); $^{13}$C NMR (125.7 MHz, CDCl$_3$) δ20.51, 20.93, 29.47, 29.68, 31.49, 34.88, 36.44, 43.05, 108.32, 111.35, 126.16, 126.78, 128.40, 146.22. Anal. Calcd for C$_{21}$H$_{28}$O$_3$: C, 76.79; H, 8.59. Found: C, 76.90; H, 8.39.

Bicyclo[3.3.1]nonane-9-spiro-3'-11',11'-dimethyl-1',2',4',9',13'-pentaoxadispiro[4.2.5.2]pentadecane (OZ68). A solution of O-methyl bicyclo[3.3.1]nonan-9-one oxime (0.84 g, 5 mmol) and 3,3-dimethyl-1,5-dioxaspiro[5.5]undecan-9-one (0.99 g, 5 mmol) in pentane (100 ml) was treated with ozone according to the general procedure. The crude product was purified by flash chromatography (silica gel, 5% ether in petroleum ether) to afford trioxolane OZ68 (0.72 g, 41%) as a colorless solid. mp 122–124° C. (ethanol/H$_2$O 5:1); $^1$H NMR (500 MHz, CDCl$_3$) δ0.97 (s, 6H), 1.40–1.56 (m, 2H), 1.62–2.16 (m, 20H), 3.49 (s, 4H); $^{13}$C NMR (125.7 MHz, CDCl$_3$) δ20.48, 20.91, 22.71, 29.40, 29.54, 29.73, 30.21, 30.64, 36.34, 70.30, 70.33, 96.76, 108.46, 111.50. Anal. Calcd for C$_{20}$H$_{32}$O$_5$: C, 68.15; H, 9.15. Found: C, 68.25; H, 9.06.

Adamantane-2-spiro-3'-8'-acetoxy-8'-(4'-fluorophenyl)-1',2',4'-trioxaspiro[4.5]decane (OZ69). A solution of O-methyl 2-adamantanone oxime (0.36 g, 2 mmol) and 4-acetoxy-4-(4-fluorophenyl)cyclohexanone (0.50 g, 2 mmol) in pentane (100 ml) and CH$_2$Cl$_2$ (10 ml) was treated with ozone according to the general procedure. The crude product was purified by flash chromatography (silica gel, 5% ether in petroleum ether) to afford trioxolane OZ69 (0.44 g, 53%) as a colorless solid. mp 147–149° C. (ethanol/H$_2$O 1:1); $^1$H NMR NMR (500 MHz, CDCl$_3$) δ1.62–2.19 (m, 20H), 2.07 (s, 3H), 2.53 (apparent d, J=12.2 Hz, 2H), 6.96–7.04 (m, 2H), 7.27–7.33 (m, 2H); $^{13}$C NMR (125.7 MHz, CDCl$_3$) δ21.93, 26.57, 26.98, 30.31, 33.71, 34.86, 34.88, 36.51, 36.87, 80.67, 107.76, 111.82, 115.20 (d, J=21.4 Hz), 128.30 (d, J=8.4 Hz), 139.92 (d, J=3.1 Hz), 161.95 (d, J=245.7 Hz), 169.43. Anal. Calcd for C$_{24}$H$_{29}$FO$_5$: C, 69.21; H, 7.02. Found: C, 68.98; H, 7.09.

Adamantane-2-spiro-3'-8'-ethoxycarbonyl-1',2',4'-trioxaspiro[4.5]decane (OZ70). A solution of O-methyl 2-adamantanone oxime (3.58 g, 20 mmol) and 4-(ethoxycarbonyl)cyclohexanone (3.40 g, 20 mmol) in pentane (160 ml) and CH$_2$Cl$_2$ (40 ml) was treated with ozone according to the general procedure. The crude product was purified by flash chromatography (silica gel, 5% ether in petroleum ether) to afford trioxolane OZ70 (3.10 g, 46%, 2.5:1 mixture of two diastereomers) as a colorless oil. Two analytically pure diastereomers were obtained by subsequent flash chromatography (silica gel, 3% ether in petroleum ether). For the cis-isomer (minor): yield, 9%; colorless oil; $^1$H NMR (500 MHz, CDCl$_3$) δ1.26 (t, J=7.1 Hz, 3H), 1.58–2.10 (m, 22H), 2.34 (m, 1H), 4.14 (q, J=7.0 Hz, 2H); $^{13}$C NMR (125.7 MHz, CDCl$_3$) δ14.15, 25.99, 26,50, 26.90, 33.10, 34.72, 34.84, 36.41, 36.79, 41.15, 60.20, 107.93, 111.66, 174.74. For the trans-isomer (major): yield, 14%; colorless solid; mp 38–39° C. (95% ethanol); $^1$H NMR (500 MHz, CDCl$_3$) δ1.25 (t, J=7.1 Hz, 3H), 1.58–2.10 (m, 22H), 2.32 (m, 1H), 4.12 (q, J=7.1 Hz, 2H); $^{13}$C NMR (125.7 MHz, CDCl$_3$) δ14.13, 26.18, 26.51, 26.92, 33.31, 34.76, 34.81, 36.42, 36.81, 41.38, 60.22, 107.90, 111.40, 174.70. Anal. Calcd for C$_{19}$H$_{28}$O$_5$: C, 67.83; H, 8.39. Found: C, 68.06; H, 8.50.

cis-Adamantane-2-spiro-3'-8'-carboxy-1',2',4'-trioxaspiro[4.5]decane (OZ71). A mixture of cis-OZ70 (0.34 g, 1 mmol), methanol (10 ml), and KOH (0.2 g) dissolved in water (1.2 ml) was heated at 50° C. for 1.5 h and then cooled to rt. The reaction mixture was acidified with conc. HCl (0.5 ml) and cooled to −20° C. The precipitate was filtered and washed with cold ethanol/H$_2$O (1:1). The filtrate was diluted with water and extracted with chloroform (2×10 ml). The combined organic layers were dried over MgSO$_4$, filtered, and concentrated in vacuo. Recrystallization of the combined solids from ethanol/H$_2$O (1:1) afforded trioxolane OZ71 (0.25 g, 81%) as a colorless solid. mp 158–159° C. (ethanol/H$_2$O 1:1); $^1$H NMR (500 MHz, CDCl$_3$) δ1.58–2.12 (m, 22H), 2.42 (m, 1H); $^{13}$C NMR (125.7 MHz, CDCl$_3$) δ25.84, 26.54, 26.94, 33.02, 34.79, 34.92, 36.46, 36.84, 40.78, 107.86, 111.85, 180.61. Anal. Calcd for C$_{17}$H$_{24}$O$_5$: C, 66.21; H, 7.84. Found: C, 66.12; H, 7.60.

trans-Adamantane-2-spiro-3'-8'-carboxy-1',2',4'-trioxaspiro[4.5]decane (OZ72). A mixture of trans-OZ70 (0.40 g, 1.2 mmol), methanol (12 ml), and KOH (0.2 g) dissolved in water (1.2 ml) was heated at 50° C. for 1.5 h and then cooled to rt. The reaction mixture was acidified with conc. HCl (0.6 ml) and cooled at −20° C. The precipitate was filtered and washed with cold ethanol/H$_2$O (1:1). The filtrate was diluted with water and extracted with chloroform (2×10 ml). The combined organic layers were dried over MgSO$_4$, filtered, and concentrated in vacuo. Recrystallization of the combined solids from ethanol/H$_2$O (1:1) afforded trioxolane OZ72 (0.33 g, 89%) as a colorless solid. mp 148–150° C. (ethanol/H$_2$O 1:1); $^1$H NMR (500 MHz, CDCl$_3$) δ1.59–2.10 (m, 22H), 2.38 (m, 1H); $^{13}$C NMR (125.7 MHz, CDCl$_3$) δ26.00, 26.55, 26.96, 33.25, 34.82, 34.87, 36.47, 36.85, 40.99, 107.80, 111.58, 180.51. Anal. Calcd for C$_{17}$H$_{24}$O$_5$: C, 66.21; H, 7.84. Found: C, 66.13; H, 7.68.

Adamantane-2-spiro-3'-8'-diethylaminocarbonyl-1',2',4'-trioxaspiro[4.5] decane (OZ73). A solution of O-methyl 2-adamantanone oxime (1.43 g, 8 mmol) and N,N-diethyl-4-oxo-cyclohexanecarboxamide (1.61 g, 8 mmol) in pentane (100 ml) and CH$_2$Cl$_2$ (20 ml) was treated with ozone according to the general procedure. The crude product was purified by flash chromatography (silica gel, 10 to 35% ether in hexanes) to afford trioxolane OZ73 (1.00 g, 34%). Recrystallization from hexanes/CH$_2$Cl$_2$ (9:1) gave the analytically pure trans-isomer (0.60 g, 21%) as a colorless solid. mp 115–117° C. (hexanes/CH$_2$Cl$_2$ 9:1); $^1$H NMR (500 MHz, CDCl$_3$) δ1.09 (t, J=7.3 Hz, 3H), 1.19 (t, J=7.3 Hz, 3H), 1.60–2.14 (m, 22H), 2.36–2.46 (m, 1H), 3.32 (q, J=7.3 Hz, 2H), 3.36 (q, J=7.3 Hz, 2H); $^{13}$C NMR (125.7 MHz, CDCl$_3$) δ13.09, 14.95, 26.53, 26.96, 27.08, 33.81, 34.78, 34.85, 36.45, 36.85, 39.16, 40.08, 41.74 107.92, 111.21, 174.14. Anal. Calcd for C$_{21}$H$_{33}$NO$_4$: C, 69.39; H, 9.15; N, 3.85. Found: C, 69.17; H, 9.03; N, 3.80.

Adamantane-2-spiro-3'-8'-benzoyloxy-1',2',4'-trioxaspiro[4.5]decane (OZ74). A solution of O-methyl 2-adamantanone oxime (1.80 g, 10 mmol) and 4-benzoyloxycyclohexanone (2.18 g, 10 mmol) in pentane (120 ml) and CH$_2$Cl$_2$ (30 ml) was treated with ozone according to the general procedure. The crude product was purified by flash chromatography (silica gel, 6% ether in petroleum ether) to afford trioxolane OZ74 (2.00 g, 52%, 2:1 mixture of two diastereomers) as a colorless solid. mp 103–106° C. (95% ethanol); $^1$H NMR (500 MHz, CDCl$_3$) δ1.59–2.18 (m, 22H), 5.12–5.21 (m, 1H), 7.40–7.48 (m, 2H), 7.52–7.61 (m, 1H), 8.01–8.09 (m, 2H); $^{13}$C NMR (125.7 MHz, CDCl$_3$) δ26.57, 26.99, 28.23, 28.50, 30.62, 31.01, 34.84, 34.92, 34.94, 36.45, 36.53, 36.87, 69.91, 70.45, 107.88, 107.98, 111.74, 111.80, 128.33, 129.57, 130.75, 130.80, 132.83, 165.84, 165.91. Anal. Calcd for C$_{23}$H$_{28}$O$_5$: C, 71.85; H, 7.34. Found: C, 71.65; H, 7.45.

Adamantane-2-spiro-3'-8'-cyano-8'-(3',4'-dichlorophenyl)-1',2',4'-trioxaspiro[4.5]decane (OZ75). A solution of O-methyl 2-adamantanone oxime (0.85 g, 4.7 mmol) and 4-cyano-4-(3,4-dichlorophenyl)cyclohexanone (1.30 g, 4.7 mmol) in pentane (50 ml) and CH$_2$Cl$_2$ (70 ml) was treated with ozone according to the general procedure. The crude product was purified by flash chromatography (silica gel, 8% ether in hexanes) to afford trioxolane OZ75 (0.62 g, 30%) as a colorless solid. mp 143–145° C. (ethanol/H$_2$O 4:1); $^1$H NMR (500 MHz, CDCl$_3$) δ1.62–2.33 (m, 22H), 7.33 (dd, J=8.3, 2.4 Hz, 1H), 7.47 (d, J=8.3 Hz, 1H), 7.57 (d, J=2.4 Hz, 1H); $^{13}$C NMR (125.7 MHz, CDCl$_3$) δ26.52, 26.90, 31.78, 34.84, 34.87, 36.52, 36.78, 42.75, 106.54, 112.38, 120.85, 125.00, 127.87, 130.99, 132.63, 133.42, 140.09. Anal. Calcd for C$_{23}$H$_{25}$Cl$_2$NO$_3$: C, 63.60; H, 5.80; N, 3.22. Found: C, 63.70; H, 5.80; N, 3.22.

Adamantane-2-spiro-3'-8'-(4'-fluorophenyl)-8'-hydroxy-1',2',4'-trioxaspiro[4.5]decane (OZ76). A mixture of OZ69

(2.40 g, 5.76 mmol), methanol (56 ml), and 17% aq. KOH (5.6 ml) was heated at 50° C. for 2 h. The reaction mixture was cooled to rt, concentrated to 10 ml, diluted with water (40 ml), and extracted with chloroform (40 ml×3). The combined organic layers were dried over MgSO₄, filtered, concentrated in vacuo. The residue was purified by crystallization from ethanol/H₂O (1:1) to give OZ76 (1.87 g, 87%) as a colorless solid. mp 122–124° C. (ethanol/H₂O 1:1); $^1$H NMR (500 MHz, CDCl₃) δ1.60–2.18 (m, 20H), 2.25 (td, J=13.7, 4.4 Hz, 2H), 6.98–7.14 (m, 2H), 7.38–7.56 (m, 2H); $^{13}$C NMR (125.7 MHz, CDCl₃) δ26.54, 26.94, 30.25, 34.84, 36.49, 36.53, 36.84, 71.85, 108.22, 111.62, 115.02 (d, J=21.1 Hz), 126.17 (d, J=7.8 Hz), 144.03 (d, J=3.2 Hz), 161.87 (d, J=245.4 Hz). Anal. Calcd for C₂₂H₂₇FO₄: C, 70.57; H, 7.27. Found: C, 70.37; H, 7.27.

Adamantane-2-spiro-3'-8'-(4'-fluorophenyl)-8'-methoxy-1',2',4'-trioxaspiro[4.5]decane (OZ77). A solution of O-methyl 2-adamantanone oxime (0.63 g, 3.5 mmol) and 4-(4-fluorophenyl)-4-methoxycyclohexanone (0.78 g, 3.5 mmol) in pentane (100 ml) and CH₂Cl₂ (10 ml) was treated with ozone according to the general procedure. The crude product was purified by flash chromatography (silica gel, 10% ether in hexanes) to afford trioxolane OZ77 (0.34 g, 25%) as a colorless solid. mp 121–123° C. (95% ethanol); $^1$H NMR (500 MHz, CDCl₃) δ1.60–2.27 (m, 22H), 2.97 (s, 3H), 6.97–7.14 (m, 2H), 7.30–7.45 (m, 2H); $^{13}$C NMR (125.7 MHz, CDCl₃) δ26.58, 26.98, 30.04, 32.80, 34.86, 34.88, 36.52, 36.88, 49.89, 75.82, 108.38, 111.51, 115.08 (d, J=21.1 Hz), 127.66 (d, J=7.8 Hz), 140.33, 161.98 (d, J=245.5 Hz). Anal. Calcd for C₂₃H₂₉FO₄: C, 71.11; H, 7.52. Found: C, 70.90; H, 7.50.

Adamantane-2-spiro-3'-8'-carboxymethyl-1',2',4'-trioxaspiro[4.5]decane (OZ78). To a solution of OZ61 (998 mg, 2.85 mmol) in 95% ethanol (10 ml) was added 15% aq. NaOH (10 ml). The mixture was heated at 60–65° C. for 2 h, cooled to rt, and acidified with 6 M HCl (10 ml). The suspension was kept at 0–5° C. for 1 h and filtered. Recrystallization of the solid from 95% ethanol afforded trioxolane OZ78 (700 mg, 76%) as a colorless solid. mp 146–148° C. (95% ethanol); $^1$H NMR (500 MHz, CDCl₃) δ1.19–1.41 (m, 2H), 1.60–2.05 (m, 21H), 2.27 (d, J=6.8 Hz, 2H); $^{13}$C NMR (125.7 MHz, CDCl₃) δ26.58, 26.97, 29.91, 33.00, 33.95, 34.86, 36.49, 36.89, 40.39, 108.38, 111.40, 177.75. Anal. Calcd for C₁₈H₂₆O₅: C, 67.06; H, 8.13. Found: C, 67.20; H, 8.13.

Adamantane-2-spiro-3'-8'-ethanesulfonyl-1',2',4'-trioxa-8'-azaspiro[4.5]decane (OZ79). A solution of O-methyl 2-adamantanone oxime (895 mg, 5.0 mmol) and 1-ethanesulfonyl-4-piperidone (955 mg, 5.0 mmol) in pentane (50 ml) and CH₂Cl₂ (50 ml) was treated with ozone according to the general procedure. The crude product was purified by flash chromatography (silica gel, 20% ether in hexanes) to afford trioxolane OZ79 (700 mg, 39%) as a colorless solid. mp 110–112° C. (methanol); $^1$H NMR (500 MHz, CDCl₃) δ1.37 (t, J=7.3 Hz, 3H), 1.62–2.08 (m, 18H), 2.97 (q, J=7.5 Hz, 2H), 3.28–3.41 (m, 2H), 3.43–3.56 (m, 2H); $^{13}$C NMR (125.7 MHz, CDCl₃) δ7.91, 26.48, 26.88, 34.70, 34.78, 34.86, 36.46, 36.74, 44.00, 44.85, 106.20, 112.40. Anal. Calcd for C₁₇H₂₇NO₅S: C, 57.12; H, 7.61; N, 3.92. Found: C, 56.94; H, 7.52; N, 3.89.

Adamantane-2-spiro-3'-1',2',4'-trioxa-8'-azaspiro[4.5]decane hydrochloride (OZ80). To a solution of OZ35 (1.41 g, 3.86 mmol) in ether (10 ml) was added 1 M ethereal HCl (40 ml). The mixture was stirred at rt for 16 h, and the resulting precipitate was filtered and washed with ether (2×5 ml) to afford trioxolane OZ80 (400 mg, 34%) as a colorless solid. mp 138–140° C. (ether); $^1$H NMR (500 MHz, CDCl₃) δ1.61–2.05 (m, 14H), 2.19 (br s, 4H), 2.34 (br s, 4H), 9.72 (br s, 2H); $^{13}$C NMR (125.7 MHz, CDCl₃) δ26.37, 26.74, 31.35, 34.70, 34.79, 36.32, 36.60, 42.31, 104.12, 113.08. Anal. Calcd for C₁₅H₂₄ClNO₃: C, 59.69; H, 8.02; N, 4.64. Found: C, 59.78; H, 7.89; N, 4.70.

Adamantane-2-spiro-3'-5',5'-bis(2'-pyridyl)-1',2',4'-trioxolane (OZ81). A solution of O-methyl 2-adamantanone oxime (716 g, 4.0 mmol) and di-2-pyridyl ketone (777 mg, 4.2 mmol) in pentane (70 ml) and CH₂Cl₂ (30 ml) was treated with ozone according to the general procedure. The crude product was purified by flash chromatography (silica gel, 4% ethanol in ether) to afford trioxolane OZ81 (620 mg, 44%) as a colorless solid. mp 135–136° C. (ether); $^1$H NMR (500 MHz, CDCl₃) δ1.60–2.10 (m, 12H), 2.27 (d, J=12 Hz, 2H), 7.21 (ddd, J=8.5, 5.0, 1.0 Hz, 2H), 7.76 (ddd, J=8.0, 8.0, 2.0 Hz, 2H), 7.95 (d, J=8.0 Hz, 2H), 8.55 (dd, J=4.5, 1.0 Hz, 2H); $^{13}$C NMR (125.7 MHz, CDCl₃) δ26.50, 26.86, 34.81, 34.88, 35.93, 36.74, 107.92, 114.58, 121.16, 123.16, 136.38, 149.12, 158.20. Anal. Calcd for C₂₁H₂₂N₂O₃: C, 71.98; H, 6.33; N, 7.99. Found: C, 71.94; H, 6.30; N, 7.91. The reaction using 2 equiv of the ketone under the same conditions gave after purification the OZ81 (680 mg, 49%).

Adamantane-2-spiro-3'-8'-acetoxyacetyl-1',2',4'-trioxa-8'-azaspiro[4.5]decane (OZ82). A solution of O-methyl 2-adamantanone oxime (1.79 g, 10 mmol) and 1-acetoxyacetyl-4-piperidone (3.82 g, 20 mmol) in pentane (50 ml) and CH₂Cl₂ (50 ml) was treated with ozone according to the general procedure. The crude product was purified by flash chromatography (silica gel, 80% ether in heaxanes) to afford trioxolane OZ82 (1.82 g, 50%) as a colorless solid. mp 112–114° C.; $^1$H NMR (500 MHz, CDCl₃) δ1.62–2.06 (m, 18H), 2.19 (s, 3H), 3.39–3.55 (m, 2H), 3.60–3.69 (m, 1H), 3.73–3.87 (m, 1H), 4.73 (AB system, 2H); $^{13}$C NMR (125.7 MHz, CDCl₃) δ20.54, 26.46, 26.85, 34.00, 34.76, 34.96, 36.43, 36.71, 40.06, 42.41, 61.27, 106.49, 112.41, 164.85, 170.43. Anal. Calcd for C₁₉H₂₇NO₆: C, 62.45; H, 7.45; N, 3.83. Found: C, 62.20; H, 7.48; N, 3.84.

Adamantane-2-spiro-3'-8'-hydroxyacetyl-1',2',4'-trioxa-8'-azaspiro[4.5]decane (OZ83). To a solution of OZ82 (600 mg, 1.64 mmol) in THF (5 ml) were added water (3 ml) and 15% aq. NaOH (3 ml). The mixture was stirred at rt for 16 h and extracted with CH₂Cl₂ (3×10 ml). The combined extracts were dried over MgSO₄ and concentrated. Crystallization of the residue from methanol to afford trioxolane OZ83 (360 mg, 68%) as a colorless solid. mp 152–154° C. (methanol); $^1$H NMR (500 MHz, CDCl₃) δ1.61–2.07 (m, 18H), 3.28–3.43 (m, 2H), 3.64–3.79 (m, 1H), 3.80–3.91 (m, 1H), 4.18 (d, J=Hz, 2H); $^{13}$C NMR (125.7 MHz, CDCl₃) δ26.43, 26.83, 33.99, 34.71, 34.79, 34.95, 36.38, 36.43, 36.68, 40.39, 41.22, 59.69, 106.37, 112.49, 170.03. Anal. Calcd for C₁₇H₂₅NO₅: C, 63.14; H, 7.79; N, 4.33. Found: C, 63.20; H, 7.85; N, 4.26.

Adamantane-2-spiro-3'-1',2',4'-trioxolane-5'-spiro-1''-3'',4''-dihydro-2''H-naphthalene (OZ84). A solution of O-methyl 2-adamantanone oxime (895 mg, 5 mmol) and α-tetralone (710 mg, 5 mmol) in pentane (90 ml) and CH₂Cl₂ (10 ml) was treated with ozone according to the general procedure. The crude product was purified by flash chromatography (silica gel, 1% ether in hexanes) to afford trioxolane OZ84 (360 mg, 23%) as a colorless solid. mp 90–92° C. (methanol/ether 9:1); $^1$H NMR (500 MHz, CDCl₃) δ1.64–2.22 (m, 16H), 2.37–2.53 (m, 2H), 2.72–3.89 (m, 2H), 7.12 (d, J=7.3 Hz, 1H), 7.19–7.35 (m, 2H), 7.65 (d, J=7.3 Hz, 1H); $^{13}$C NMR (125.7 MHz, CDCl₃) δ20.63, 26.65, 27.09, 29.24, 34.09, 34.14, 34.99, 35.00, 35.78, 36.43, 37.00, 37.22, 107.73, 112.40, 126.23, 127.97, 128.69, 129.36, 131.93, 140.70. Anal. Calcd for C₂₀H₂₄O₃: C, 76.89; H, 7.74. Found: C, 76.77; H, 8.00.

Adamantane-2-spiro-3'-1',2',4'-trioxolane-5'-spiro-2"-3", 4"-dihydro-1"H-naphthalene (OZ85). A solution of O-methyl 2-adamantanone oxime (895 mg, 5 mmol) and β-tetralone (710 mg, 5 mmol) in pentane (90 ml) and $CH_2Cl_2$ (10 ml) was treated with ozone according to the general procedure. The crude product was purified by flash chromatography (silica gel, 2% ether in hexanes) to afford trioxolane OZ85 (400 mg, 26%) as a colorless solid. mp 64–66° C.; $^1$H NMR (500 MHz, $CDCl_3$) δ1.62–2.18 (m, 16H), 2.96 (t, J=6.6 Hz, 2H), 3.12 (AB system, 2H), 7.02–7.21 (m, 4H); $^{13}$C NMR (125.7 MHz, $CDCl_3$) δ26.59, 26.97, 27.72, 31.78, 34.78, 34.83, 34.86, 34.99, 36.53, 36.55, 36.88, 38.19, 108.44, 112.02, 125.95, 126.10, 128.32, 129.08, 133.89, 135.51. Anal. Calcd for $C_{20}H_{24}O_3$: C, 76.89; H, 7.74. Found: C, 76.77; H, 7.61.

Adamantane-2-spiro-3'-8'-(4'-fluorobenzenesulfonyl)-1', 2',4'-trioxa-8'-azaspiro[4.5]decane (OZ86). A solution of O-methyl 2-adamantanone oxime (895 mg, 5 mmol) and 1-(4-fluorobenzenesulfonyl)-4-piperidone (1.22 g, 5 mmol) in pentane (50 ml) and $CH_2Cl_2$ (50 ml) was treated with ozone according to the general procedure. The crude product was purified by flash chromatography (silica gel, 25% ether in hexanes) to afford trioxolane OZ86 (450 mg, 21%) as a colorless solid. mp 122–124° C. (95% ethanol); $^1$H NMR (500 MHz, $CDCl_3$) δ1.60–2.05 (m, 18H), 2.92–3.06 (m, 2H), 3.25–3.38 (m, 2H), 7.16–7.28 (m, 2H), 7.74–7.84 (m, 2H); $^{13}$C NMR (125.7 MHz, $CDCl_3$) δ26.46, 26.85, 34.05, 34.76, 34.80, 36.42, 36.71, 44.29, 105.83, 112.46, 116.39 (d, J=22.9 Hz), 130.23 (d, J=9.2 Hz), 133.03, 165.30 (d, J=254.8 Hz). Anal. Calcd for $C_{21}H_{26}FNO_5S$: C, 59.56; H, 6.19; N, 3.31. Found: C, 59.75; H, 6.40; N, 3.27.

Adamantane-2-spiro-3'-8'-chloroacetyl-1',2',4'-trioxa-8'-azaspiro[4.5]decane (OZ87). A solution of O-methyl 2-adamantanone oxime (2.01 g, 11.17 mmol) and 1-chloroacetyl-4-piperidone (3.02 g, 17.09 mmol) in pentane (50 ml) and $CH_2Cl_2$ (50 ml) was treated with ozone according to the general procedure. The crude product was purified by flash chromatography (silica gel, 25% ether in heaxanes) to afford trioxolane OZ87 (1.60 g, 42%) as a colorless solid. mp 112–114° C. (methanol); $^1$H NMR (500 MHz, $CDCl_3$) δ1.62–2.10 (m, 18H), 3.51–3.72 (m, 3H), 3.74–3.88 (m, 1H), 4.07 (AB system, 2H); $^{13}$C NMR (125.7 MHz, $CDCl_3$) δ26.43, 26.82, 33.96, 34.72, 34.92, 36.41, 36.68, 40.24, 40.83, 40.88, 40.94, 44.15, 50.73, 106.43, 112.38, 164.98. Anal. Calcd for $C_{17}H_{24}ClNO_4$: C, 59.73; H, 7.08; N, 4.10. Found: C, 59.60; H, 7.23; N, 4.06.

Adamantane-2-spiro-3'-8'-[2'-(4'-nitrobenzoyloxy)ethyl]-1',2',4'-trioxaspiro[4.5]decane (OZ88). A solution of O-methyl 2-adamantanone oxime (895 mg, 5 mmol) and 4-[2-(4-nitrophenyloxy)ethyl]cyclohexanone (1.45 g, 5 mmol) in pentane (80 ml) and $CH_2Cl_2$ (20 ml) was treated with ozone according to the general procedure. The crude product was purified by flash chromatography (silica gel, 10% ether in petroleum ether) to afford trioxolane OZ88 (1.10 g, 48%) as a colorless solid. mp 124–126° C.; $^1$H NMR (500 MHz, $CDCl_3$) δ1.22–1.39 (m, 2H), 1.41–1.58 (m, 2H), 1.62–2.11 (m, 21H), 4.41 (t, J=6.6 Hz, 2H), 8.19 (d, J=8.3 Hz, 2H), 8.28 (d, J=8.8 Hz, 2H); $^{13}$C NMR (125.7 MHz, $CDCl_3$) δ26.58, 26.98, 30.05, 33.42, 34.12, 34.85, 36.52, 36.89, 64.26, 108.61, 111.40, 123.55, 130.67, 135.84, 150.67, 164.71. Anal. Calcd for $C_{25}H_{31}NO_7$: C, 65.63; H, 6.83; N, 3.06. Found: C, 65.76; H, 6.90; N, 3.18.

Adamantane-2-spiro-3'-8'-(2'-hydroxyethyl)-1',2',4'-trioxaspiro[4.5]decane (OZ89). To a solution of OZ88 (610 mg, 1.33 mmol) in THF (10 ml) at rt was added NaOH solution (400 mg, 10 mmol) in water (5 ml). The mixture was stirred at rt for 6 h, concentrated, and extracted with $CH_2Cl_2$ (2×20 ml). The organic layers were combined, washed with water (10 ml) and brine (10 ml), dried over $MgSO_3$, and evaporated. The residue was recrystallized from ethanol/water (2:1) to give trioxolane OZ89 (220 mg, 54%) as a colorless solid. mp 88–90° C. (ethanol/water 2:1); $^1$H NMR (500 MHz, $CDCl_3$) δ1.09–2.15 (m, 25H), 3.61–3.79 (m, 2H); $^{13}$C NMR (125.7 MHz, $CDCl_3$) δ26.58, 26.97, 30.15, 32.72, 34.20, 34.84, 34.86, 36.49, 36.89, 39.12, 60.85, 108.89, 111.25. Anal. Calcd for $C_{18}H_{28}O_4$: C, 70.10; H, 9.15. Found: C, 70.24; H, 9.24.

Adamantane-2-spiro-3'-8'-hydroxy-8'-methyl-1',2',4'-trioxaspiro[4.5]decane (OZ90). To a solution of methyllithium (1.85 ml, 1.4 M in ether, 2.4 mmol) and lithium perchlorate (0.26 g, 2.4 mmol) in THF (2 ml) at −78° C. was added a solution of OZ05 (556 mg, 2 mmol) in THF (20 ml). The reaction was stirred at −78° C. for 2 h before being quenched with methanol (2 ml). The mixture was allowed to warm up to rt and concentrated in vacuo. The residue was dissolved in $CH_2Cl_2$ and washed with 1 M HCl (20 ml), water (20 ml), and brine (20 ml). The organic layer was dried over $MgSO_4$, filtered, and concentrated. The crude product was purified by flash chromatography (silica gel, 25% ether in petroleum ether) to afford trioxolane OZ90 (215 mg, 37%, 1.4:1 mixture of two diastereomers) as a colorless solid. mp 91–94° C. (hexanes/$CH_2Cl_2$ 9:1); $^1$H NMR (500 MHz, $CDCl_3$) δ1.29 (s, 3H), 1.60–2.12 (m, 22H) assigned to the major isomer; 1.25 (s, 3H), 1.60–2.12 (m, 22H) assigned to the minor isomer; $^{13}$C NMR (125.7 MHz, $CDCl_3$) δ26.54, 26.56, 26.95, 26.97, 29.37, 30.05, 30.31, 30.54, 34.79, 34.83, 34.87, 34.96, 36.44, 36.46, 36.49, 36.73, 36.86, 68.57, 68.96, 108.52, 108.57, 111.42, 111.51. Anal. Calcd for $C_{17}H_{26}O_4$: C, 69.36; H, 8.90. Found: C, 69.19; H, 8.82.

EXAMPLE 2

Chemical Properties of Compounds OZ01–OZ90

TABLE 1

| Compd | MW | Yield (%) | m.p. (° C.) | Tm dec. (° C.) | Stereochemistry |
| --- | --- | --- | --- | --- | --- |
| OZ01 | 212.1 | 58 | ND (oil) | ND | achiral |
| OZ02 | 226.1 | 39 | 52–54 | 193.3 | achiral |
| OZ03 | 264.2 | 46 | ND (oil) | ND | achiral |
| OZ04 | 316.3 | 40 | 150 dec. | 150.8 | achiral |
| OZ05 | 278.2 | 44 | 126–128 | 156.3 | achiral |
| OZ06 | 230.1 | 59 | ND (oil) | ND | diastereomeric mixture |
| OZ07 | 312.2 | 57 | ND (oil) | ND | diastereomeric mixture |
| OZ08 | 364.5 | 58 | ND (oil) | ND | diastereomeric mixture |
| OZ09 | 340.3 | 50 | 83–84 | 196.5 | mixture of achiral diastereomers |

TABLE 1-continued

| Compd | MW | Yield (%) | m.p. (° C.) | Tm dec. (° C.) | Stereochemistry |
|---|---|---|---|---|---|
| OZ10 | 322.2 | 33 | 84–85 | 159.4 | achiral |
| OZ11 | 364.5 | 39 | 123–125 | 162.4 | achiral |
| OZ12 | 304.4 | 17 | 122–124 | 149.8 | single achiral diastereomer |
| OZ13 | 318.4 | 9 | 153–155 | 170.1 | single achiral diastereomer |
| OZ14 | 340.4 | 23 | 106 dec. | 113.3 | single diastereomer |
| OZ15 | 307.2 | 83 | 97–99 | 157.8 | racemic mixture |
| OZ16 | 293.4 | 73 | 137–139 | 153.6 | racemic mixture |
| OZ17 | 294.2 | 35 | 116–118 | 158.4 | racemic mixture |
| OZ18 | 320.5 | 52 | 123–124 | 166.5 | single achiral diasteromer |
| OZ19 | 383.5 | 86 | 62–64 | 157.8 | racemic mixture |
| OZ20 | 348.5 | 54 | 73–75 | 170.5 | achiral |
| OZ21 | 310.4 | 42 | 78–80 | 190.7 | achiral |
| OZ22 | 266.3 | 65 | ND (oil) | ND | achiral |
| OZ23 | 337.5 | 26 | 44–46 | 160.8 | achiral |
| OZ24 | 369.5 | 33 | 130–132 | 154.9 | achiral |
| OZ25 | 306.4 | 58 | 49–51 | 167.7 | single achiral diastereomer |
| OZ26 | 320.5 | 48 | 71–72 | 173.4 | achiral |
| OZ27 | 340.5 | 49 | 103–105 | 161.7 | single achiral diastereomer |
| OZ28 | 349.5 | 90 | 68–70 | 162.4 | racemic mixture |
| OZ29 | 458.4 | 85 | 142–144 dec. | 155.7 | racemic mixture |
| OZ30 | 411.4 | 90 | 161–163 dec. | 174.8 | racemic mixture |
| OZ31 | 398.5 | 56 | 149–151 | 161.1 | racemic mixture |
| OZ32 | 280.4 | 89 | 100–106 | 147.9 | mixture of achiral diastereomers |
| OZ33 | 292.4 | 49 | 125–127 | 163.1 | achiral |
| OZ34 | 416.5 | 23 | 155–157 | 181.4 | achiral |
| OZ35 | 365.5 | 40 | 82–84 | 159.4 | achiral |
| OZ36 | 368.5 | 38 | 95–97 | 201.7 | achiral |
| OZ37 | 333.4 | 96 | 118–120 | 151.2 | racemic mixture |
| OZ38 | 422.5 | 65 | 146–148 | 165.1 | racemic mixture |
| OZ39 | 446.6 | 58 | 137 dec. | 146.9 | racemic mixture |
| OZ40 | 306.4 | 31 | 67–69 | 164.2 | single achiral diastereomer |
| OZ41 | 358.5 | 50 | 103–106 | 159.0 | single achiral diastereomer |
| OZ42 | 348.4 | 32 | 105–107 | 159.1 | achiral |
| OZ43 | 417.3 | 26 | 128–130 | 155.8 | achiral |
| OZ44 | 384.4 | 45 | 86–89 | 157.5 | achiral |
| OZ45 | 528.3 | 23 | 92–95 | 133.7 | achiral |
| OZ46 | 484.4 | 26 | 60–62 | 161.3 | achiral |
| OZ47 | 374.9 | 36 | 122–124 | 159.3 | single achiral diastereomer |
| OZ48 | 408.5 | 47 | 115–117 | 156.1 | single achiral diastereoiner |
| OZ49 | 307.4 | 14 | 77–79 | 155.7 | achiral |
| OZ50 | 314.4 | 15 | 128–129 | 147.1 | achiral |
| OZ51 | 419.5 | 16 | 124–125 | 152.3 | achiral |
| OZ52 | 376.5 | 58 | 86–88 | 154.9 | achiral |
| OZ53 | 393.5 | 30 | 116–117 | 152.7 | achiral |
| OZ54 | 351.4 | 85 | 126–128 | 149.3 | racemic mixture |
| OZ55 | 448 | 31 | 88–90 | | racemic mixture |
| OZ56 | 343.4 | 19 | 146–148 | 158.0 | achiral |
| OZ57 | 440 | 9 | 142–144 | 158.0 | achiral |
| OZ58 | 365.4 | 43 | 124–126 | 147.0 | achiral |
| OZ59 | 435.5 | 18 | 116–118 | 152.2 | achiral |
| OZ60 | 405.5 | 10 | 130–132 | 152.6 | achiral |
| OZ61 | 350.5 | 20 | 62–64 | 161.7 | single achiral diastereomer |
| OZ62 | 364.5 | 25 | 136–138 | 201.0 | mixture of achiral diastereomers |
| OZ63 | 365.5 | 51 | 137–138 | 158.3 | single achiral diastereomer |
| OZ64 | 378.5 | 62,18[1] | 84–86 | 163.8 | single achiral diastereomer |
| OZ65 | 382.4 | 61 | 154 dec. | 159.4 | mixture of achiral diastereomers |
| OZ66 | 408.4 | 27 | 87–90 | 198.5 | mixture of achiral diastereomers |
| OZ67 | 328.5 | 33 | 120–122 | 162.3 | single achiral diastereomer |
| OZ68 | 352.5 | 41 | 122–124 | 163.1 | achiral |
| OZ69 | 416.5 | 53 | 147–149 | 164.1 | single achiral diastereomer |
| OZ70 | 336.4 | 46,14[1] | 38–39 | 162.8 | single achiral diastereomer |
| OZ71 | 308.4 | 81 | 158–159 | 165.9 | single achiral diastereomer |
| OZ72 | 308.4 | 89 | 148–150 | 161.9 | single achiral diastereomer |
| OZ73 | 363.5 | 34,20[1] | 115–117 | 160.2 | single achiral diastereomer |
| OZ74 | 384.5 | 52 | 103–106 | 161.2 | mixture of achiral diastereomers |
| OZ75 | 434.4 | 30 | 143–145 | 159.1 | single achiral diastereomer |
| OZ76 | 374.5 | 87 | 122–124 | 149.6 | single achiral diastereomer |
| OZ77 | 388.5 | 25 | 121–123 | 161.3 | single achiral diastereomer |
| OZ78 | 322.4 | 76 | 146–148 | 157.5 | single achiral diastereomer |
| OZ79 | 357.5 | 39 | 110–112 | 153.6 | achiral |
| OZ80 | 301.8 | 34 | 138–140 | 129.8 | achiral |

TABLE 1-continued

| Compd | MW | Yield (%) | m.p. (° C.) | Tm dec. (° C.) | Stereochemistry |
|---|---|---|---|---|---|
| OZ81 | 350.4 | 44 | 135–136 | 150.7 | achiral |
| OZ82 | 365.4 | 50 | 112–114 | 153.7 | achiral |
| OZ83 | 323.4 | 68 | 152–154 | 163.6 | achiral |
| OZ84 | 312.4 | 23 | 90–92 | 164.5 | racemic mixture |
| OZ85 | 312.4 | 26 | 64–66 | 152.8 | racemic mixture |
| OZ86 | 423.5 | 21 | 122–124 | 153.0 | achiral |
| OZ87 | 341.8 | 42 | 112–114 | 149.7 | achiral |
| OZ88 | 457.5 | 48 | 124–126 | 158.9 | single achiral diastereomer |
| OZ89 | 308.4 | 49 | 88–90 | 154.7 | single achiral diastereomer |
| OZ90 | 294.4 | 37 | 91–94 | 153.2 | mixture of achiral diastereomers |

[1]yield of pure achiral diastereomer isolated from the mixture of achiral diastereomers formed in the reaction

EXAMPLE 3

Antimalarial Activity of OZ01–OZ90

Each trioxolane was screened against the chloroquine-resistant K1 and chloroquine-sensitive NF54 strains of *P. falciparum* in vitro. In the single dose STI in vivo screen, Moro SPF mice infected with the ANKA strain of *P. Berghei* (groups of three mice) were treated on day one post-infection with trioxolanes dissolved or suspended in 3% ethanol and 7% Tween 80. Trioxolanes were administered as single 10 or 100 mg/kg doses sc and po. Antimalarial activity was measured by percent redution in parasitemia on day three post-infection and survival times compared to an untreated control group. Survival to day 30 post-infection is considered to be a cure. For comparative analysis, in Table 2 below data is presented for trioxolanes OZ01–OZ54 along with the controls, fenozan, artemisinin, dihydroartemisinin, arteether, artemether, and artesunate:

TABLE 2

| Compd | IC$_{50}$ (ng/ml) K1/NF54 | Dose (mg/kg) | Activity (%) po/sc | Survival (days) po/sc |
|---|---|---|---|---|
| NONE | | | 0 | 5.6 ± 0.3 |
| OZ01 | >100/>100 | 100 | 0/0 | 5.3/5.3 |
| OZ02 | >100/94 | 100 | 0/0 | 5.0/5.0 |
| OZ03 | 1.2/1.6 | 100 | 100/100 | 14.3/28 |
|  |  | 10 | 94/100 | 7.2/11.9 |
| OZ04 | >100/>100 | 100 | 0/0 | 5.3/5.3 |
| OZ05 | 0.19/0.36 | 100 | 100/100 | 10.7/30 |
|  |  | 10 | 94/99.7 | 7.1/8.6 |
| OZ06 | 18/22 | 100 | T/T | 1.0/1.0 |
| OZ07 | 66/49 | 100 | 0/0 | 6.0/5.7 |
| OZ08 | 2.4/2.8 | 100 | 99.7/99.9 | 8.0/9.7 |
| OZ09 | 32/39 | 100 | 0/81 | 5.0/6.3 |
| OZ10 | 0.40/0.67 | 10 | 99.6/99.98 | 8.9/10.5 |
| OZ11 | 1.5/2.7 | 10 | 99.99/100 | 11.4/18 |
| OZ12 | 0.60/0.77 | 10 | 75/99.8 | 7.0/9.3 |
| OZ13 | 0.40/0.50 | 10 | 56/99.7 | 6.7/9.7 |
| OZ14 | 91/>100 | 10 | 23/96 | 6.0/7.7 |
| OZ15 | 0.60/1.0 | 10 | 99.8/99.9 | 7.4/8.2 |
| OZ16 | 0.45/0.67 | 10 | 79/99.2 | 6.7/7.3 |
| OZ17 | 85/>100 | 10 | 0/18 | 5.3/6.3 |
| OZ18 | 63/84 | 10 | 0/0 | 5.0/5.3 |
| OZ19 | 1.3/2.7 | 10 | 98.3/99.98 | 7.5/13.4 |
| OZ20 | 15/20 | 10 | 97/90 | 7.4/7.0 |
| OZ21 | 14/25 | 10 | 0/0 | 5.0/6.0 |
| OZ22 | 0.32/0.56 | 10 | 35/99.6 | 6.0/7.7 |
| OZ23 | 0.29/0.57 | 10 | 99.5/99.9 | 7.7/8.9 |
| OZ24 | 0.35/0.58 | 10 | 93/99.9 | 7.0/8.7 |
| OZ25 | 1.1/2.1 | 10 | 99.9/99.97 | 8.4/16.5 |
| OZ26 | 3.1/5.0 | 10 | 88/99.9 | 7.0/9.7 |
| OZ27 | 2.2/4.8 | 10 | 99.97/99.92 | 12.6/17.1 |
| OZ28 | 2.1/2.5 | 10 | 93/99.97 | 7.3/12.3 |
| OZ29 | 9.7/13 | 10 | 0/0 | 5.0/5.0 |
| OZ30 | 0.65/1.3 | 10 | 0/86 | 5.3/9.0 |
| OZ31 | 3.0/3.0 | 10 | 99.95/99.95 | 9.0/17.7 |
| OZ32 | 0.25/0.51 | 10 | 79/91 | 6.7/8.7 |
| OZ33 | 2.3/3.5 | 10 | 80/99.97 | 6.7/11.7 |
| OZ34 | 42/60 | 10 | 0/0 | 5.3/5.7 |
| OZ35 | 1.7/2.1 | 10 | 74/99.98 | 6.3/9.3 |
| OZ36 | 24/62 | 10 | 0/0 | 5.7/5.7 |
| OZ37 | 1.1/1.6 | 10 | 83/99.98 | 6.7/13 |
| OZ38 | 0.86/1.3 | 10 | 83/99.98 | 6.7/25.3 |
| OZ39 | 1.4/1.8 | 10 | 61/99.3 | 6.3/7.7 |
| OZ40 | 1.4/2 | 10 | 99/99.8 | 7.3/9.0 |
| OZ41 | 3.5/4.6 | 10 | 99.98/99.5 | 12.1/10.7 |
| OZ42 | 2.3/2.6 | 10 | 68/92 | 6.0/7.0 |
| OZ43 | 11/7.5 | 10 | 99.97/97 | 8.9/7.3 |
| OZ44 | 2.5/2.3 | 10 | 99.3/99.9 | 7.0/8.3 |
| OZ45 | 17/27 | 10 | 15/16 | 6.0/5.0 |
| OZ46 | 22/19 | 10 | 99/62 | 7.7/6.0 |
| OZ47 | 7.5/7.4 | 10 | 99.98/99 | 12.7/8.0 |
| OZ48 | 11/13 | 10 | 99.8/42 | 8.7/6.3 |
| OZ49 | 0.82/0.93 | 10 | 81/85 | 6.7/7.3 |
| OZ50 | 1.1/1.2 | 10 | 77/97 | 7.0/7.3 |
| OZ51 | 2.5/2.5 | 10 | 89/100 | 7.0/14 |
| OZ52 | 3.1/3.0 | 10 | 88/99.7 | 6.7/8.0 |
| OZ53 | 1.4/1.7 | 10 | 9/58 | 6.0/6.3 |
| OZ54 | 32/35 | 10 | 85/97 | 7.0/7.0 |
| OZ55 | 0.49/0.60 | 10 | 45/97 | 6.0/7.3 |
| OZ56 | 0.59/0.64 | 10 | 93/99.97 | 6.7/10.3 |
| OZ57 | 3.1/2.8 | 10 | 32/98.4 | 6.0/7.7 |
| OZ58 | 7.1/7.2 | 10 | 39/52 | 6.0/6.3 |
| OZ59 | 1.4/1.3 | 10 | 51/99.95 | 6.0/10.0 |
| OZ60 | 1.1/1.2 | 10 | 71/100 | 6.0/10.3 |
| OZ61 | 0.52/0.53 | 10 | 91/96 | 7.0/7.3 |
| OZ62 | 33/28 | 10 | 0/0 | 6/5 |
| OZ63 | 1.6/1.6 | 10 | 99.62/99.91 | 7.3/9.3 |
| OZ64 | 1.5/1.3 | 10 | 95/98 | 7.3/8.0 |
| OZ65 | 57/65 | 10 | 0/1 | 5.0/5.0 |
| OZ66 | 44/36 | 10 | 0/0 | 5.3/5.7 |
| OZ67 | >100/>100 | 10 | 0/0 | 5.0/5.0 |
| OZ68 | 41/49 | 10 | 1/6 | 5.0/5.3 |
| OZ69 | 1.6/1.4 | 10 | 56/40 | 6.3/6.3 |
| OZ70 | 1.2/1.1 | 10 | 98/94 | 7.7/7.7 |
| OZ71 | 4.5/3.7 | 10 | 98/97 | 7.3/8.3 |
| OZ72 | 15/13 | 10 | 97/95 | 7.7/6.7 |
| OZ73 | 6.5/8.2 | 10 | 27/36 | 6.0/6.7 |
| OZ74 | 2.3/3.5 | 10 | 63/99.97 | 6.3/10.0 |
| OZ75 | 2.4/4.3 | 10 | 77/5 | 7.3/5.0 |
| OZ76 | 1.7/3.0 | 10 | 49/94 | 6.3/8.0 |
| OZ77 | 1.4/2.2 | 10 | 99.9/98 | 9.0/8.3 |
| OZ78 | >10/>10 | 10 | 94/79 | 8.7/6.7 |

TABLE 2-continued

| Compd | IC$_{50}$ (ng/ml) K1/NF54 | Dose (mg/kg) | Activity (%) po/sc | Survival (days) po/sc |
|---|---|---|---|---|
| OZ79 | 0.38/0.81 | 10 | 85/99.94 | 7.0/9.3 |
| OZ80 | <0.16/0.34 | 10 | 59/84 | 6.3/7.7 |
| OZ81 | >10/>10 | 10 | 0/0 | 5.3/5.0 |
| OZ82 | /1.3 | 10 | 91/79 | 7.3/7.0 |
| OZ83 | /1.0 | 10 | 92/99.8 | 7.0/8.0 |
| OZ84 | /1.9 | 10 | 92/99.99 | 7.7/14.7 |
| OZ85 | /2.0 | 10 | 34/99.7 | 6.0/8.3 |
| OZ86 | /2.3 | 10 | 77/99.9 | 6.7/11.3 |
| OZ87 | /4.5 | 10 | 22/53 | 5.7/6.0 |
| OZ88 | /4.2 | 10 | 62/99.1 | 6.0/11.7 |
| OZ89 | /1.0 | 10 | 94/99.8 | 7.3/8.7 |
| OZ90 | /1.1 | 10 | 89/99 | 7.0/8.0 |
| Fenozan | 3.2/3.0 | 10 | 99.95/100 | 8.6/13.4 |
| Artemisinin | 1.2/1.9 | 100 | 98/100 | 7.3/14 |
|  |  | 10 | 65/87 | 6.5/7.0 |
| Dihydroart | 0.22/0.23 | 10 | 80/NA | 6.8/NA |
| Arteether | 0.41/0.54 | 100 | 99.98/100 | 12/26.3 |
|  |  | 10 | 98/100 | 8/9.7 |
| Artemether | 0.5/0.37 | 100 | 99.95/100 | 14.7/14.7 |
|  |  | 10 | 98.7/99.96 | 8.0/9.0 |
| Artesunate | 1.2/1.2 | 10 | 83.3/81.1 | 7.1/8.0 |

OZ01–OZ09. According to the results of this study, OZ01, OZ02, OZ06, OZ07, and OZ09 were found to be less active. OZ04 was found to be completely inactive. OZ03, OZ05, and OZ08 were found to be more active.

OZ10–OZ18. Trioxolane ketals OZ10 and OZ11, potential prodrugs off OZ05, displayed quite good in vitro and in vivo activities, with especially good oral data for OZ11. The oxime ether (OZ15) and oxime (OZ16) derivatives of OZ05 were only slightly less potent than the parent trioxolane ketone in vitro. However, relative to OZ05, in vivo activity improved for OZ15, but weakened for OZ16.

OZ19–OZ27. The highest in vitro potency was obtained for trioxolanes having ether (OZ22), carbamate (OZ23), and amide (OZ24) functional groups. Of these, OZ23 had the best in vivo activity. OZ19, the benzyl oxime ether analog of OZ15, was some 2-fold less potent than OZ15 in vitro, but maintained the good in vivo activity of the prototype. OZ25 and OZ27, analogs of OZ18, both had excellent activity. The oral survival for OZ27 was noteworthy. When the spirocyclohexane in OZ03 was replaced with spirododecane in OZ20, in vitro potency decreased by an order of magnitude, but in vivo activity decreased only slightly. When the spiroadamantane in OZ05 was replaced with a conformationally flexible spirododecane in OZ21, in vitro potency decreased 70-fold, and all in vivo activity was lost.

OZ28 to OZ36. Six members of the fourth trioxolane series, OZ28, OZ30, OZ31, OZ32, OZ33, and OZ35, had IC$_{50S}$<5 ng/ml. Of these, only oxime ether OZ28 and ketal OZ31 had any noteworthy oral efficacy (>7 days survival), although both were somewhat less active than their respective prototypes, OZ15 and OZ11. OZ33, the 4,4-dimethyl analog of OZ03, lost oral activity relative to the prototype. When the spiroadamantane in OZ11 was replaced with a 3,35,5-tetramethylcyclohexane in OZ36, in vitro activity decreased some 20-fold, and all in vivo activity was lost.

OZ37–OZ45. OZ37, OZ38, and OZ39, had IC50S <2 ng/ml, but none had high in vivo activity. OZ40, the 4-isopropyl analog of OZ25 was only slightly less active than OZ25, but its activity contrasts with OZ18, the completely inactive 4-tert-butyl analog. OZ41, the 4-fluoro analog of OZ27 was as active as the prototype. In trioxolanes OZ42 to OZ45, the benzophenone skeleton is incorporated into the spiroadamantane trioxolane pharmacophore. Of these, OZ43 and OZ44 possessed the best combination of in vitro and in vivo activities.

OZ46–OZ54. OZ47 and OZ48 were 2 to 3-fold less potent than OZ27 in vitro, although OZ47 maintained the very good oral survival seen with OZ27 and OZ41. Acetamide OZ49 was 2-fold less potent in vitro and was less active in vivo than its benzamide analog OZ24. OZ51, the toluenesulfonamide analog of OZ24 had reasonable in vitro potency. OZ50, a sulfone analog of OZ03, was as potent as the parent in vitro, but was somewhat less active in vivo.

OZ55–OZ63. Although the polar pyridinium trioxolane OZ55 was quite potent in vitro, its in vivo activity was minimal. OZ56, the sulfonamide analog of acetamide OZ49, was more active than the prototype, but the oral survival time for this compound was minimal. Although the intrinsic potency of ester OZ61 was high, its in vivo activity was modest. Nitrile OZ63 had a good combination of in vitro potency and in vivo activity.

OZ64–OZ72. Esters OZ64, OZ70, and their corresponding carboxylic acid isomers OZ71 and OZ72 possessed a good combination of in vitro and in vivo activities, although OZ72 was some 3-fold less potent in vitro than its isomer OZ71. Of these, ethyl ester OZ70 and acid OZ71 were the most active overall. OZ66 and OZ67, analogs of OZ27 in which the spiroadamantane was replaced with a diphenyl or a spirobicyclo[3.3.1]nonane, respectively, were completely inactive. OZ68, the spirobicyclo[3.3.1] nonane analog of OZ11, was similarly inactive.

OZ73 to OZ81. Amide OZ73 was only weakly active. Benzoate ester OZ74 was less active than its corresponding alcohol OZ32. OZ75 was less active than its unsubstituted phenyl analog OZ63. Tertiary carbinol OZ76 was as active as its acetate ester OZ69, whereas its methyl ether derivative OZ77 had excellent activity. Acid OZ78 was only weakly active in vitro, but it had promising vivo activity. Ethanesulfonamide OZ79, like its methanesulfonamide analog OZ56, was very potent in vitro and had good vivo activity. Although piperdine OZ80 was quite potent in vitro, its vivo activity was modest. The dipyridyl analog OZ81 was inactive.

OZ82 to OZ90. In contrast to the very active α-hydroxy acetamide OZ83 and its corresponding ester OZ82, the α-chloroacetamide OZ87 was much less active. The tetrahydronaphthalene analogs OZ84 and OZ85 were very active in vitro, but only OZ84 had good vivo activity. Sulfonamide OZ86 was no more active than the prototype sulfonamide OZ51. Alcohols OZ89 and OZ90 were quite active, and both had better in vivo efficacy than alcohol OZ32.

EXAMPLE 4

Activity of Trioxolanes Against *P. berghei*

As shown in Table 3 below, the trioxolane compounds possess impressive antimalarial activity against *P. berghei* in vivo as determined in the 1-day and 4-day Peters test. Based on po ED$_{50}$/ED$_{90}$ values, OZ11 was the most orally active compound of all of the trioxolanes and control compounds. However, chloroquine, fenozan, artemether, OZ23, OZ25, OZ27, OZ31, and OZ43 were only slightly less orally active than OZ11.

TABLE 3

| | P. berghei (1 day) $ED_{50}/ED_{90}$ (mg/kg) | | P. berghei (4 day) $ED_{50}/ED_{90}$ (mg/kg) | |
|---|---|---|---|---|
| Compound | po | sc | po | sc |
| OZ03[a] | 5.0/8.8 | 0.7/2.2 | 1.0/2.7 | 0.6/1.1 |
| OZ05[a] | 3.5/7.0 | 0.16/2.3 | 1.5/6.1 | 0.6/1.0 |
| OZ10 | 2.3/6.3 | 0.06/2.2 | 1.3/3.0 | 0.5/0.9 |
| OZ11 | 1.5/2.8 | NA/0.87 | 1.8/3.1 | 0.5/0.9 |
| OZ12 | NA | NA | 6.8/10.5 | 0.8/1.4 |
| OZ15 | 3.1/5.9 | 0.7/2.6 | 2.9/6.3 | 0.7/1.1 |
| OZ19 | 3.4/9.4 | 1.8/3.6 | <10/>10 | NA |
| OZ20 | 4.3/9.7 | 7.1/10 | NA | NA |
| OZ23 | 1.6/5.5 | NA/1.9 | 0.9/2.0 | 0.5/0.9 |
| OZ24 | 3.9/9.0 | NA/2.1 | <10/>10 | NA |
| OZ25 | 1.9/3.1 | 1.7/3.0 | 1.2/3.7 | 2.2/3.7 |
| OZ27 | 1.9/3.2 | 1.8/3.1 | 1.3/2.6 | 0.2/0.9 |
| OZ30 | NA | NA | <10/>10 | NA |
| OZ31 | 1.6/3.9 | 1.1/2.4 | NA | NA |
| OZ32 | 1.9/13 | >1/2.1 | 2.6/5.1 | 0.6/1.3 |
| OZ41 | 2.8/5.1 | NA | NA | NA |
| OZ43 | 2.1/4.0 | NA | NA | NA |
| Chloroquine[a] | 3.0/4.2 | 1.5/3.2 | 1.7/3.1 | 1.5/3.0 |
| Fenozan | 1.7/4.3 | 1.7/3.2 | 1.9/2.7 | 1.1/2.3 |
| Artemisinin | 9.1/14 | NA | NA | NA |
| Artemether[a] | 2.0/4.3 | 2.1/2.3 | NA | NA |
| Arteether | 2.4/6.8 | NA | NA | NA |
| Artesunate[a] | 5.0/13 | 0.86/16 | 2.4/13 | 1.5/6.3 |
| Dihydroart | 2.9/12 | NA | NA | NA |

[a]average values of at least two experiments

EXAMPLE 5

Neurotoxicity of Trioxolanes

Even though reported clinical neurotoxicity for the semi-synthetic artemisinins is very rare (Park et al., 1998), neurotoxicity is a potential drawback for antimalarial peroxides of any structural class. Against the NB2a cell line (Fishwick et al., 1995) trioxolanes OZ03, OZ04, OZ05, Z07, and OZ08 had relatively high $IC_{50S}$ of 13, 44, 31, 27, and 42 $\mu M$, respectively. In this same screen, dihydroartemisinin, the presumed metabolite of all the semisynthetic artemisinins (Titulaer et al., 1991; White, 1994), was quite neurotoxic with an $IC_{50}$ of 0.22 $\mu M$. There was no apparent relationship between trioxolane structure and neurotoxicity and these five trioxolanes.

EXAMPLE 6

Onset of Action and Recrudescence of OZ03, OZ05, OZ11, and OZ27

The onset of drug action of OZ03, OZ05, OZ11, OZ27 and control was determined after a single fixed dose of 100 mg/kg administered po to groups of five animals on day +3 post-infection (day 0). The reduction of parasitemia was monitored 12 h after treatment, and the time of recrudescence was assessed by daily blood smears for 14 days, followed by intermittent assessment for up to 30 days.

Artemether, artesunate, and each of the four trioxolanes caused a rapid decline in parasitemia, suggesting that all of the compounds are equally rapidly acting antimalarial agents. Recrudescence (>5% parasitemia) occurs on day 5 for artemether, on day 2 for artemether, on day 2 for artesunate, on day 7 for OZ03, on day 5 for OZ05, on day 10 for OZ11, and on day 11 for OZ27. For these five compounds, the recrudescence times correlated (r=0.88, p=0.02) with the po survival times (10 mg/kg dose), but not with the $ED_{50}/ED_{50}$ values. This data suggests that the trioxolanes tested thus far have a comparable (OZ03 and OZ05) or a longer (OZ11, OZ27) duration of action than does artemether.

EXAMPLE 7

Treatment of Schistosomiasis

Mice (MORO SPF female 18–20g) were infected with 90 (±10) cecaria of Schistosoma mansoni subcutaneously. Following infection, three of the animals were treated with OZ05 p.o., 100 mg/kg on days 7, 14, 21, 28, 35, and 42.

Compared to control mice, two of the treated mice had a reduction in parasitaemia of 100%, and the third mice a reduction in parasitaemia of 53%. In the same assay, mice treated with artemether showed similar activities, but at doses four times higher than that of the OZ05. Further, in the same assay, arteflene (6×600 mg/kg p.o.) and fenozan (6×100 mg/kg p.o.) were inactive.

In addition, the trioxolanes OZ05 200 mg/kg p.o. and OZ11 100 mg/kg p.o. treated once at day 49 of infection showed activity against adult S. mansoni. In contrast, artemether shows no activity against adult S. mansoni.

EXAMPLE 8

Effect of OZ Compounds on Schistosoma Mansoni
Effect of OZ Compounds on 21-Day-old Schistosomules Mice were infected with 100 Schistosoma mansoni cercariae on day 21 post-treatment. Each group was treated per os with OZ compounds at a single dose of 200 mg/kg. Untreated mice served as the control. All groups were killed 4 weeks after treatment and the liver and intestine were removed and separated. The liver and intestine were compressed and alive male and female worms could be seen and counted. The effect of the compounds was evaluated by mean total and female worm burden. The results are shown in Table 4.

TABLE 4

| | (mean ± standard deviation) | | |
|---|---|---|---|
| | Antischistosomule Effeet | | |
| OZ Compound | TWR (%) | Mean female worm burden | FWR (%) |
| 05 | 90 | 1.5 ± 1.0[b] | 88 |
| 11 | 85 | 2.0 ± 1.9[b] | 84 |
| 15 | 63 | 3.8 ± 2.4[b] | 70 |
| 23* | 90 | 2.0 ± 1.0[b] | 84 |
| 27 | 63 | 5.2 ± 1.6[b] | 58 |
| 14** | 7 | 12.4 ± 4.2 | 0 |
| 20 | 0 | 13.8 ± 5.5 | 0 |
| 22 | 75 | 3.0 ± 1.9[b] | 76 |
| 32 | 73 | 3.8 ± 1.9[b] | 70 |
| 04 | 7 | 11.6 ± 3.2[a] | 7 |
| 17 | 23 | 11.6 ± 3.3[a] | 7 |
| 18 | 12 | 11.4 ± 2.7[a] | 9 |
| 21 | 0 | 15.0 ± 9.7 | 0 |
| 29 | 28 | 10.0 ± 3.7[a] | 20 |
| 36 | 16 | 11.0 ± 4.0[a] | 12 |
| Control | — | 12.5 ± 3.9 | — |
| Artemether | 82.2 | | |

Number of animals n = 5 (10 in control; 4 in OZ 05 and 3 in OZ 23 group); TWR, total worm reduction rate; FWR, female worm reduction rate; *3/6 mice and **1/6 mice treated were dead within 1 h after administration; [a]$P > 0.05$, [b]$P < 0.01$ vs control.

Effect of OZ Compounds on Adult Schistosomes (49-Day-old)

Mice were infected with 100 Schistosoma mansoni cercariae on day 49 post-treatment. Each group was treated per os with OZ compounds at a single dose of 400 mg/kg. Untreated mice served as the control. All groups were killed 4 weeks after treatment and the liver and intestine were removed and separated. The liver and intestine were compressed and alive male and female worms could be seen and counted. The effect of the compounds was evaluated by mean total and female worm burden, and the results are set forth in Table 5.

TABLE 5

Anti-adult schistosome effect

| OZ Compound | Mean total worm burden | TWR (%) | Total dead worm | Percentage of dead worm |
|---|---|---|---|---|
| 05 | 40.2 ± 13.6 | 0 | 31 | 13.4 (31/232) |
| 11 | 30.0 ± 1.9[a] | 16.2 | 6 | 3.9 (6/156) |
| 15 | 37.8 ± 20.6 | 0 | 21 | 10 (21/210) |
| 23#* | 39.7 ± 19.6 | 0 | 5 | 4 (5/124) |
| 27 | 28.4 ± 9.5[a] | 19.6 | 15 | 9.6 (15/157) |
| 14#** | 44.5 ± 13.2 | 0 | 0 | 0 |
| 20 | 38.6 ± 3.6 | 0 | 0 | 0 |
| 32 | 26.2 ± 5.9[b] | 26.8 | 50 | 27.6 (50/181) |
| 43 | 35.4 ± 15.8[a] | 1.1 | 0 | 0 |
| 04 | 37.6 ± 13.4 | 0 | 0 | 0 |
| 17 | 36.2 ± 13.8 | 0 | 10 | 5.2 (10/191) |
| 18 | 35.6 ± 7.2[a] | 0.6 | 0 | 0 |
| 21 | 36.2 ± 9.0 | 0 | 0 | 0 |
| 29 | 31.0 ± 13.7[a] | 13.4 | 0 | 0 |
| 36 | 40.2 ± 12.2 | 0 | 0 | 0 |
| Control | 35.8 ± 9.4 | — | — | — |
| Artemether | | 31.0 | | |

Number of animals: n = 5 (10 in control; 4 in OZ 14 and 3 in OZ 23 group); TWR, total worm reduction rate; FWR, female worm reduction rate; x ± SD; [a]P > 0.05, [b]P < 0.05 vs control. # The dose used was 200 mg/kg. *2/5 mice and **1/5 mice treated were dead within 1 h after administration.

It should be appreciated that the spiro and dispiro 1,2,4-trioxolane compositions of this invention may contain trioxolanes within the scope of the formulas described above, or prodrugs or analogues of these compounds or a racemic mixture of either the D or the L form. Also, minor dosage and formulation modifications of the composition and the ranges expressed herein may be made and still come within the scope and spirit of the present invention.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

All articles cited herein and in the following list are hereby expressly incorporated in their entirety by reference.

CITATIONS

Augustine, R. L. Stereochemistry of the catalytic hydrogenation of some bicyclic α,β-unsaturated ketones. *J. Org. Chem.*, 1958, 23, 1853–1856.

Cammenga, H. K., and Epple, M. Basic principles of thermoanalytical techniques and their applications in preparative chemistry. *Angew. Chem. Int. Ed. Engl.* 1995, 34, 1171–1187.

Cormier, R. A., and McCauley, M. D. Catalytic hydrogenation of diketones. *Synth. Comm.* 1988, 18, 675–676.

Cumming, J. N., Polypradith, P., Posner, G. H. Antimalarial activity of artemisinin (qinghaosu) and related trioxanes: mechanism(s) of action. *Adv. Pharmacol.* 1997. 37, 254–297.

Fishwick, J., McLean, W. G.; Edwards, G.; Ward, S. A. The Toxicity of Artemisinin and Related Compounds on Neuronal and Glial Cells in Culture. *Chem.-Biol. Interact.* 1995, 96, 263–271.

Griesbaum, K., Liu, X., and Dong, Y. Diozonides from coozonolyses of suitable O-methyl oximes and ketones. *Tetrahedron* 1997a, 53, 5463–5470.

Griesbaum, K., Liu, X., Kassiaris, A., and Scherer, M. Ozonolyses of O-alkylated ketoximes in the presence of carbonyl groups: a facile access to ozonides. *Liebigs Ann./Recueil.* 1997b, 1381–1390.

Jefford, C. Peroxidic Antimalarials. *Adv. Drug Res.* 1997, 29, 271–325.

Meshnick, S. R., Taylor, T. E., Kamchonwongpaisan, S. Artemisinin and the antimalarial endoperoxides: from herbal remedy to targeted chemotherapy. *Microbiol. Rev.* 1996, 60, 301–315.

Park, B. K.; O'Neill, P. M.; Maggs, J. L.; Pirmohamed, M. Safety Assessment of Peroxide Antimalarials: Clinical and Chemical Perspectives. *Br. J. Clin. Pharmacol.* 1998, 46, 521–529.

Stork, G., Brizzolara, A., Landesman, H., Szmuskovicz, J., and Terrell, R. The enamine alkylation and acylation of carbonyl compounds. *J. Amer. Chem. Soc.* 1963, 85, 207–222.

Titulaer, H. A. C., Zuidema, J., and Lugt, C. B. Formulation and pharmacokinetics of artemisinin and its derivatives. *Int. J. Pharmaceut.* 1991, 69, 83–92.

Vennerstrom, J. L., and Eaton, J. W. Oxidants, oxidant drugs and malaria. *J. Med. Chem.* 1988, 31, 1269–1277.

Wesche, D. L., DeCoster, M. A., Tortella, F. C. and Brewer, T. G. Neurotoxicity of artemisinin analogs in vitro. *Antimicrob. Agents. Chemother.* 1994, 38, 1813–1819.

White, N. J. Clinical pharmacokinetics and pharmacodynamics of artemisinin and derivatives. *Trans. R. Soc. Trop. Med. Hyg.* 1994, 88, 41–43.

What is claimed is:

1. A spiro or dispiro 1,2,4-trioxolane wherein the 1,2,4-trioxolane is selected from the group consisting of: adamantane-2-spiro-3'-1',2',4'-trioxaspiro[4.5]decane; adamantane-2-spiro-3'-8'-oxo-1',2',4'-trioxaspiro[4.5]decane; adamantane-2-spiro-3'-1',2',4',9',12'-pentaoxadispiro[4.2.4.2]tetradecane; adamantane-2-spiro-3'-11',11'-dimethyl-1',2',4',9',13'-pentaoxadispiro[4.2.5.2]pentadecane; adamantane-2-spiro-3'-8'-ethoxycarbonyl-1',2',4'-trioxa-8'-azaspiro[4.5]decane; adamantane-2-spiro-3'-8'-propyl-1',2',4'-trioxaspiro[4.5]decane; and adamantane-2-spiro-3'-8'-phenyl-1',2',4'-trioxaspiro[4.5]decane.

2. A pharmaceutical composition for prophylaxis and treatment of malaria comprising: a malaria prophylaxis or malaria treatment-effective amount of a spiro or dispiro 1,2,4-trioxolane, its prodrugs and optical isomers thereof, and a pharmaceutically acceptable carrier, said trioxolane being sterically hindered on at least one side of the trioxolane heterocycle.

3. A composition according to claim 2, wherein the spiro or dispiro 1,2,4-trioxolane has the following structure:

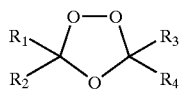

wherein R₁, R₂, R₃, and R₄ are the same or different, and are selected from the group consisting of substituted or unsubstituted linear or branched alkyl, aryl, and alkaryl groups, substituted or unsubstituted alicyclic groups that may be interrupted by one or more oxygen, sulfur or nitrogen atoms, and substituted or unsubstituted aromatic or heterocyclic groups, whereby none of R₁, R₂, R₃, or R₄ may be hydrogen; and further providing that R₁ and R₂ taken together and/or R₃ and R₄ taken together may form a substituted or unsubstituted alicyclic group which is optionally interrupted by one or more oxygen, sulfur or nitrogen atoms.

4. A composition according to claim 3, wherein R₁ and R₂ taken together and/or R₃ and R₄ taken together is a mono- or di-substituted C₅–C₁₂ spirocyclo group which is optionally interrupted by one or more oxygen, sulfur, or nitrogen atoms, said oxygen, sulfur, or nitrogen atoms being optionally substituted.

5. A composition according to claim 4 wherein R₁ and R₂ taken together and/or R₃ and R₄ taken together is adamantane.

6. A composition according to claim 5 wherein R₁ and R₂ taken together is adamantane and R₃ and R₄ taken together is a spirocyclohexyl ring that is substituted or functionalized or substituted at the 4-position.

7. A composition according to claim 5 wherein R₁ and R₂ taken together is adamantane and R₃ and R₄ are substituted or unsubstituted phenyl or heterocylic rings.

8. A composition according to claim 6 wherein the spirocyclohexyl ring is interrupted by one or more oxygen, sulfur, or nitrogen atoms.

9. A composition according to claim 8 wherein the spirocyclohexyl ring is N-substituted piperidyl.

10. A composition according to claim 6 wherein the spirocyclohexyl ring is functionalized with a substituent selected from the group consisting of a substituted or unsubstituted substituent selected from the group consisting of a linear or branched alkyl, ketone, acid, alcohol, amine, amide, sulfonamide, ether, ester, oxime, urea, oxime ether, sulfone, lactone, carbamate, semicarbazone, phenyl, heterocycle, and alicyclic group.

11. A composition according to claim 2 wherein the 1,2,4-trioxolane is selected from the group consisting of: adamantane-2-spiro-3'-1',2',4'-trioxaspiro[4.5]decane; adamantane-2-spiro-3'-8'-oxo-1',2',4'-trioxaspiro[4.5]decane; adamantane-2-spiro-3'-1',2',4',9',12'-pentaoxadispiro[4.2.4.2]tetradecane; adamantane-2-spiro-3'-11',11'-dimethyl-1',2',4',9',13'-pentaoxadispiro[4.2.5.2]pentadecane; adamantane-2-spiro-3'-8'-ethoxycarbonyl-1',2',4'-trioxa-8'-azaspiro[4.5]decane; adamantane-2-spiro-3'-8'-propyl-1',2',4'-trioxaspiro[4.5]decane; and adamantane-2-spiro-3'-8'-phenyl-1',2',4'-trioxaspiro[4.5]decane.

12. A composition according to claim 2 that is suitable for administration by a method selected from the group consisting of oral, subcutaneous, intravenous, intranasal, rectal, sublingual, and buccal.

13. Adamantane-2-spiro-3'-1',2',4', 9',12'-pentaoxadispiro[4.2.4.2]tetradecane.

14. Adamantane-2-spiro-3'-11',11'-dimethyl-1',2',4', 9', 13'-pentaoxadispiro[4.2.5.2]pentadecane.

15. Adamantane-2-spiro-3'-8'-ethoxycarbonyl-1',2',4'-trioxa-8'-azaspiro[4.5]decane.

16. Adamantane-2-spiro-3'-8'-propyl-1',2',4'-trioxaspiro[4.5]decane.

17. Adamantane-2-spiro-3'-8'-phenyl-1',2',4'-trioxaspiro[4.5]decane.

18. Adamantane-2-spiro-3'-5',5'-diphenyl-1',2',4'-trioxolane.

19. Adamantane-2-spiro-3'-8'-(4'-fluorophenyl)-8'-methoxy-1',2',4'-trioxaspiro[4.5]decane.

20. Adamantane-2-spiro-3'-8'-carboxymethyl-1',2',4'-trioxaspiro[4.5]decane.

21. Adamantane-2-spiro-3'-1',2',4'-trioxa-8'-azaspiro[4.5]decane hydrochloride.

22. Adamantane-2-spiro-3'-8'-(2'-hydroxyethyl)-1',2',4'-trioxaspiro[4.5]decane.

23. A method of preventing or treating malaria comprising: administrating a malaria prevention or malaria treatment effective amount of a Spiro or dispiro 1,2,4-trioxolane in a pharmaceutically acceptable carrier, said trioxolane being sterically hindered on at least one side of the trioxolane heterocycle.

24. A method according to claim 23, wherein the spiro or dispiro 1,2,4-trioxolane has the following structure:

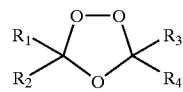

wherein R₁, R₂, R₃, and R₄ are the same or different, and are selected from the group consisting of substituted or unsubstituted linear or branched alkyl, aryl, and alkaryl groups, substituted or unsubstituted alicyclic groups that may be interrupted by one or more oxygen, sulfur or nitrogen atoms, and substituted or unsubstituted aromatic or heterocyclic groups, whereby none of R₁, R₂, R₃, or R₄ may be hydrogen; and further providing that R₁ and R₂ taken together and/or R₃ and R₄ taken together may form a substituted or unsubstituted alicyclic group which is optionally interrupted by one or more oxygen, sulfur or nitrogen atoms.

25. A method according to claim 23 wherein the trioxolane is administered in a dose of between about 0.1–1000 mg/kg/day.

26. A method according to claim 25 wherein the trioxolane is administered in a dose of between about 1–100 mg/kg/day.

27. A method according to claim 23 wherein the trioxolane is administered in a single dose.

28. A method according to claim 23 wherein the trioxolane is administered in divided doses.

29. A method according to claim 23 wherein the trioxolane is administered in a malaria-preventive dose beginning 1–2 weeks prior to malaria exposure and ending 1–2 weeks post exposure.

30. A method according to claim 23 wherein the trioxolane is administered in a malaria-curative dose over 1–10 days.

31. A method of manufacturing a composition for prophylaxis and treatment of malaria comprising: mixing a malaria prophylaxis or malaria treatment-effective amount of a spiro or dispiro 1,2,4-trioxolane, its prodrugs and optical isomers thereof, with a pharmaceutically acceptable carrier, said trioxolane being sterically hindered on at least one side of the trioxolane heterocycle.

32. A method according to claim 31, wherein the spiro or dispiro 1,2,4-trioxolane has the following structure:

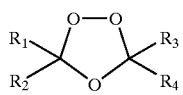

wherein $R_1$, $R_2$, $R_3$, and $R_4$ are the same or different, and are selected from the group consisting of substituted or unsubstituted linear or branched alkyl, aryl, and alkaryl groups, substituted or unsubstituted alicyclic groups that may be interrupted by one or more oxygen, sulfur or nitrogen atoms, and substituted or unsubstituted aromatic or heterocyclic groups, whereby none of $R_1$, $R_2$, $R_3$, or $R_4$ may be hydrogen; and further providing that $R_1$ and $R_2$ taken together and/or $R_3$ and $R_4$ taken together may form a substituted or unsubstituted alicyclic group which is optionally interrupted by one or more oxygen, sulfur or nitrogen atoms.

33. A method of treating cancer comprising: administrating a cancer treatment effective amount of a spiro or dispiro 1,2,4-trioxolane in a pharmaceutically acceptable carrier, said trioxolane being sterically hindered on at least one side of the trioxolane heterocycle.

34. A method of prophylaxis or treatment of schistosomiasis comprising: administrating a schistosomiasis prophylaxis or treatment effective amount of a spiro or dispiro 1,2,4-trioxolane in a pharmaceutically acceptable carrier, said trioxolane being sterically hindered on at least one side of the trioxolane heterocycle.

\* \* \* \* \*